(12) United States Patent
Gharib et al.

(10) Patent No.: US 11,890,233 B2
(45) Date of Patent: Feb. 6, 2024

(54) SYSTEMS AND METHODS FOR DRUG DELIVERY

(71) Applicant: CALIFORNIA INSTITUTE OF TECHNOLOGY, Pasadena, CA (US)

(72) Inventors: Morteza Gharib, Altadena, CA (US); Jinglin Huang, Tianjin (CN)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 354 days.

(21) Appl. No.: 16/839,333

(22) Filed: Apr. 3, 2020

(65) Prior Publication Data
US 2020/0315851 A1    Oct. 8, 2020

Related U.S. Application Data

(60) Provisional application No. 62/939,393, filed on Nov. 22, 2019, provisional application No. 62/860,448, filed on Jun. 12, 2019, provisional application No. 62/829,847, filed on Apr. 5, 2019, provisional application No. 62/829,459, filed on Apr. 4, 2019.

(51) Int. Cl.
*A61F 9/04* (2006.01)
*A61F 9/00* (2006.01)
*A61M 31/00* (2006.01)

(52) U.S. Cl.
CPC .............. *A61F 9/04* (2013.01); *A61F 9/0017* (2013.01); *A61M 31/00* (2013.01); *A61M 2205/3368* (2013.01); *A61M 2205/3626* (2013.01); *A61M 2210/0612* (2013.01)

(58) Field of Classification Search
CPC ... A61F 9/04; A61F 2007/0004; A61F 9/0017
See application file for complete search history.

(56) References Cited

U.S. PATENT DOCUMENTS

| 10,278,920 B1* | 5/2019 | Peyman .............. A61K 9/0051 |
| 2003/0195438 A1 | 10/2003 | Petillo |
| 2017/0087009 A1* | 3/2017 | Badawi .............. A61K 8/0208 |
| 2017/0087017 A1* | 3/2017 | Iseli ...................... A61F 9/008 |
| 2019/0216639 A1* | 7/2019 | Bruder ..................... A61F 7/02 |
| 2020/0000638 A1* | 1/2020 | Herekar ................ A61N 5/062 |
| 2020/0078212 A1* | 3/2020 | Seo ........................ A61F 7/02 |

(Continued)

FOREIGN PATENT DOCUMENTS

WO    WO 2013/114127 A1    8/2013

OTHER PUBLICATIONS

Akinkunmi, F. O., et al., "Effects of Temperature on the Thermodynamic and Dynamical Properties of Glycerol-Water Mixtures: A Computer Simulation Study of Three Different Force Fields", The Journal of Physical Chemistry B, 2015, vol. 119, pp. 6250-6261.

(Continued)

*Primary Examiner* — Adam Marcetich
*Assistant Examiner* — Meagan Ngo
(74) *Attorney, Agent, or Firm* — ONE LLP

(57) ABSTRACT

Disclosed are example embodiments of methods and systems for inducing drug to thoroughly mix in a patient's vitreous humor. One of the systems includes: a heat transfer pad that transfer heat to or from the eyeball; and a control module electronically coupled to the heat transfer pad for controlling one or more heat transfer elements disposed thereon.

12 Claims, 58 Drawing Sheets

(56) References Cited

U.S. PATENT DOCUMENTS

| | | | |
|---|---|---|---|
| 2020/0129327 A1* | 4/2020 | Grant | A61F 9/04 |
| 2020/0170833 A1* | 6/2020 | Duan | A61F 9/04 |

OTHER PUBLICATIONS

Avastin, retrieved from https://www.edinburghclinic.com/files/2021/07/TEC-Avastin-Patient-Information-Data-sheet.pdf, 2022, pp. 1-3.

Balazs, E. A., "Aging Changes in the Vitreous", Aging and Human Visual Function, 1982, vol. 1, pp. 45-57.

Balazs, E. A., "Functional Anatomy of the Vitreous", Foundations of Clinical Ophthalmology, Chapter 17, 1992, vol. 1, pp. 1-16.

Bos, K.J., et al., "Collagen fibril organisation in mammalian vitreous by freeze etch/rotary shadowing electron microscopy", Micron, vol. 32, pp. 301-306.

Cristancho, D. M., et al., "Volumetric properties of glycerol + water mixtures at several temperatures and correlation with the Jouyban-Acree model", Rev. Colomb. Cienc. Quim. Farm., 2011, vol. 40, No. 1, pp. 92-115.

Del Amo, E. M., et al., "Pharmacokinetic aspects of retinal drug delivery", Progress in Retinal and Eye Research, 2017, vol. 57, pp. 134-185.

Ganji, D. D., et al., "Physical Relationships Between Nanoparticle and Nanofluid Flow", Application of Nonlinear Systems in Nanomechanics and Nanofluids, Chapter 3, 2015, pp. 71-107.

Gaudana, R., et al., "Ocular Drug Delivery", The AAPS Journal, 2010, vol. 12, No. 3, pp. 348-360.

Geroski, D. H., et al., "Drug Delivery for Posterior Segment Eye Disease", Investigative Ophthalmology & Visual Science, 2000, vol. 41, No. 5, pp. 961-964.

Holz, F. G., et al., "Recent developments in the treatment of age-related macular degeneration", The Journal of Clinical Investigation, 2014, vol. 124, No. 4, pp. 1430-1438.

Kim, H., et al., "FcRn receptor-mediated pharmacokinetics of therapeutic IgG in the eye", Molecular Vision, 2009, vol. 15, pp. 2803-2812.

Kummer, M. P., et al., "Artificial Vitreous Humor for In Vitro Experiments", Proceedings of the 29th Annual International Conference of the IEEE EMBS, Lyon, France, Aug. 23-26, 2007, pp. 6406-6409.

Locke, J. C., et al., "Further Studies of the Viscosity of Aspirated Human Vitreous Fluid: With Special Reference to Its Use in Retinal Detachment Surgery", Tr. Am. Opth. Soc., 1965, vol. 63, pp. 129-145.

Macula, retrieved from https://www.aao.org/eye-health/anatomy/macula-6, 2016, pp. 1-2.

Maurice, D. M., et al., "Ocular Pharmacokinetics", Pharmacology of the Eye, Chapter 2, 1984, pp. 19-116.

Miller, C. C., "The Stokes-Einstein Law for Diffusion in Solution", Proceedings of the Royal Society of London, Series A, 1924, vol. 106, No. 740, pp. 724-749.

Murthy, K. R., et al., "Proteomic analysis of human vitreous humor", Clinical Proteomics, 2014, vol. 11, No. 29, pp. 1-11.

Purves, D., et al., editors, "Eye Movements and Sensory Motor Integration", Neuroscience, $2^{nd}$ edition, Chapter 20, 2001, pp. 427-441.

Scott, K. S., et al., "The Use of Vitreous Humor as an Alternative to Whole Blood for the Analysis of Benzodiazepines", Journal of Forensic Science, 2001, vol. 46, No. 3, pp. 694-697.

Shu, J.-J., et al., "Inclined wall plumes in porous media", Fluid Dynamics Research, 1997, vol. 21, pp. 303-317.

Stewart, M. W., et al., "Extended Duration Vascular Endothelial Growth Factor Inhibition in the Eye: Failures, Successes, and Future Possibilities", Pharmaceutics, 2018, vol. 10, No. 21, pp. 1-12.

Wilson, M. E., et al., "How to Give Intravitreal Injections", EyeNet Magazine, 2013, pp. 45-47.

Yorston, D., "Anti-VEGF drugs in the prevention of blindness", Community Eye Health Journal, 2014, vol. 27, No. 87, pp. 44-46.

Yorston, D., "Intravitreal injection technique", Community Eye Health Journal, 2014, vol. 27, No. 87, p. 47.

* cited by examiner

Figure 2.5. Various injection sites (The orange arrow represents needle tip; the front of the eye is labeled in (a) and will be the same for (b) and (c))

| Velocity Field | $\bar{v}$ $\bar{x}$ | $\bar{v}$ $\bar{x}$ | $\bar{v}$ $\bar{x}$ | $\bar{v}$ $\bar{x}$ | $\bar{v}$ $\bar{x}$ | ... |
|---|---|---|---|---|---|---|
|  | $T_0$ | $T_1$ | $T_2$ | $T_3$ | $T_4$ | ... |
| Time | $T_0$ | $T_1$ | $T_2$ | $T_3$ | $T_4$ | ... |

*FIG. 14*

SYSTEMS AND METHODS FOR DRUG DELIVERY

CROSS-REFERENCE TO RELATED APPLICATIONS

The present application claims the benefit of U.S. Provisional Application No. 62/939,393, filed Nov. 22, 2019, U.S. Provisional Application No. 62/860,448, filed Jun. 12, 2019, U.S. Provisional Application No. 62/829,847, filed Apr. 5, 2019, and U.S. Provisional Application No. 62/829,459, filed Apr. 4, 2019, all of which are incorporated herein by reference in their entirety for all purposes.

BACKGROUND

Human eye is a very delicate structure, with 80% of its space between the lens and retina filled with a fluid-like gel, vitreous humor. Vitreous humor is composed of approximately 98-99% water with trace amounts of hyaluronic acid, glucose, anions, cations, ions, and collagen. It is a very important space for eye disease treatments as well because a lot of the treatment processes occur in this space. In the center of the retina, there is a small but important area called the macula. It is a very critical structure as it allows us to see details of objects in front of us. The macula encounters diverse issues as people get older. When it happens, patients usually experience severe vision loss if they don't receive proper treatment. To name a few macula-related diseases: branch retinal vein occlusion, macular degeneration (dry or wet), retinal detachment, retinitis pigmentosa, etc. In this study, we focus on investigating how drugs travel/mix in the vitreous chamber to reach the macula and treat macula-related eye diseases.

Many eye diseases are macula-related. Since age-related macular degeneration (AMD) is the leading cause of central vision loss in the developed world, it is a desire to improve its treatment efficacy. Patients with AMD see a dark spot in the center of their vision. There are two forms of the disease. The "dry" form of the disease is characterized by yellow deposits or choroidal neovascularization that develops underneath the retinal pigment epithelium. Fluid and blood leak through these abnormal vessels, creating scar tissues. In the "wet" form, normal macular tissues are lost which also cause severe vision loss.

Wet AMD can be managed through serial intravitreal injections of anti-vascular endothelial growth factor (anti-VEGF) agents. During such an injection, an ophthalmologist injects the drug into the vitreous chamber of a patient every four weeks. These anti-VEGF injections are effective at stabilizing, often improving visual acuity in patients with wet AMD. A similar treatment method can also be used to treat diseases such as diabetic macular edema, retinal vein occlusion, and other vascular disorders.

Although effective, intravitreal injection is not a perfect solution for every patient, and it potentially causes many complications such as intraocular inflammation, retinal detachment, traumatic lens damage, and sustained ocular hypertension.

SUMMARY

Provided herein are embodiments of systems and methods for inducing drug to mix within a vitreous humor. One of the systems can include: a flexible contact pad configured to be placed onto an eye of a patient; a plurality of heat transfer elements disposed on the flexible contact pad configured to transfer heat out of or into the flexible pad; and a control module electronically coupled to each of the plurality of the heat transfer elements for controlling the temperature of each heat transfer element. The plurality of heat transfer elements can include four heat transfer elements, which can be disposed at four different quadrants of the flexible contact pad.

The flexible contact pad can include a silicone pad with head conducting property (embedded heat conducting metal). Additionally, the flexible contact pad can include one or more flaps extending outward, which can be disposed on opposite sides of the flexible pad. The one or more flaps can include an adhesive layer on a surface opposite of the plurality of heat transfer elements.

The control module can independently control a heat transfer characteristic of each heat transfer element. The control module can also create a temperature difference between one or more of the heat transfer elements and the respective area adjacent to each of the heat transfer element. The temperature difference can have a range between 2.5 to 12.5 degrees Celsius. In some embodiments, temperature difference is between 5 and 10 degrees Celsius. For example, the temperature difference can be 10 degrees Celsius. The control module can activate only the heat transfer element at a lower quadrant of the flexible pad. In other words, only the lower portion of the eyeball is heated.

One of the methods for inducing drug mixing in a patient's vitreous humor can include: injecting drug into the vitreous humor; and generating a temperature difference between one or more heat transfer elements and adjacent area of each of the one or more heat transfer elements. The temperature difference generated can have a range between 2.5-12.5 degrees Celsius. In some embodiments, the temperature difference can be 10 degrees Celsius. The region being heated and/or cooled can be the medial region, the inferior region, the superior region, or a combination thereof.

In yet another embodiment, an eye patch for inducing drug to mix in a patient's vitreous humor is disclosed. The eye patch can include: a heat transfer pad configured to transfer heat to or from the eyeball; and a control module electronically coupled to the heat transfer pad for controlling one or more heat transfer elements disposed on the heat transfer pad.

Other features and advantages of the present invention will be or will become apparent to one with skill in the art upon examination of the following figures and detailed description, which illustrate, by way of examples, the principles of the present invention.

BRIEF DESCRIPTION OF THE DRAWINGS

The foregoing summary, as well as the following detailed description, is better understood when read in conjunction with the accompanying drawings. The accompanying drawings, which are incorporated herein and form part of the specification, illustrate a plurality of embodiments and, together with the description, further serve to explain the principles involved and to enable a person skilled in the relevant art(s) to make and use the disclosed technologies.

FIG. 14 illustrates a chart showing flow property information in a sequential manner in accordance with some embodiments of the presentation disclosure.

The figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

DETAILED DESCRIPTION

Overview

As previously mentioned, Wet AMD can be managed through serial intravitreal injections. However, this procedure is not a perfect solution for every patient and can cause complications. As such, new and improved methods and systems for intravitreal injection are disclosed. To assist the understanding of the new and improved methods and systems for intravitreal injection, it is helpful to start with an overview.

Figure 1A:
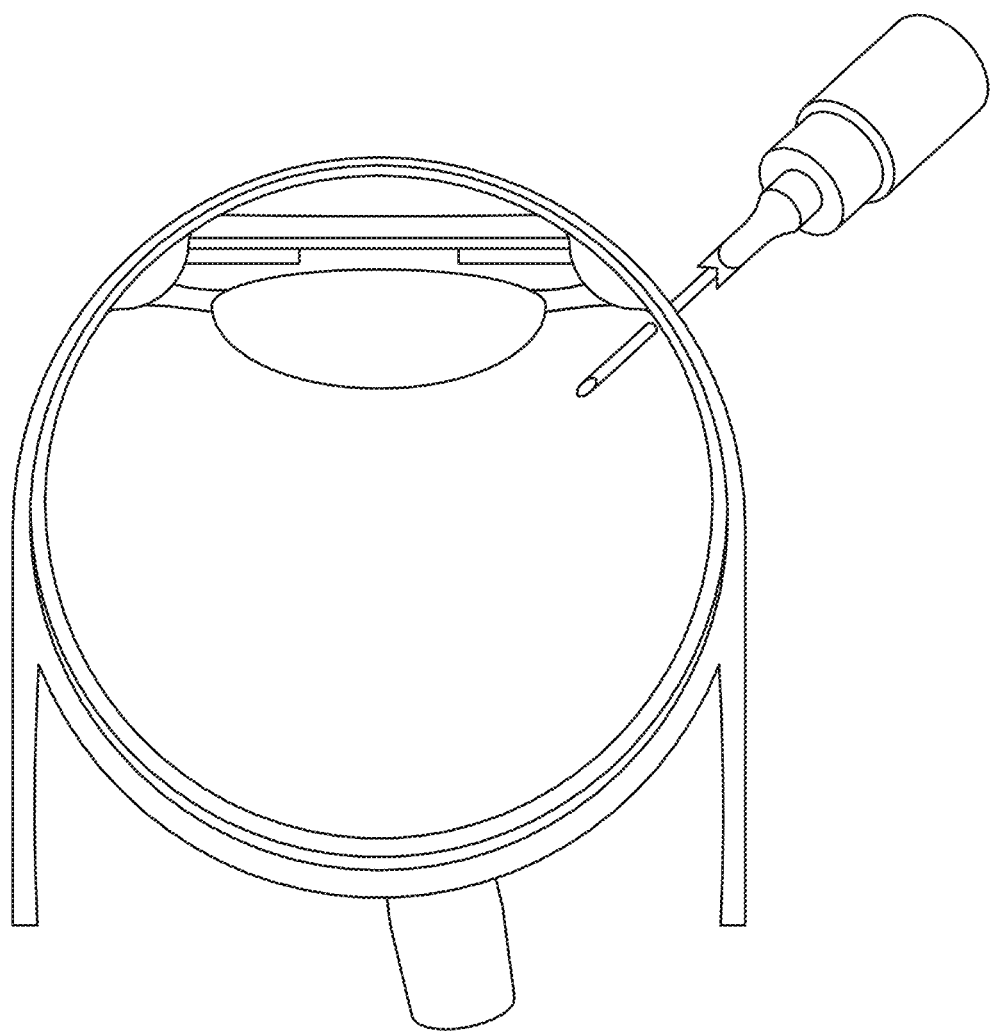
FIGS. 1A-C are illustrations of the eye to demonstrate the drug injection process.
Figure 1C:
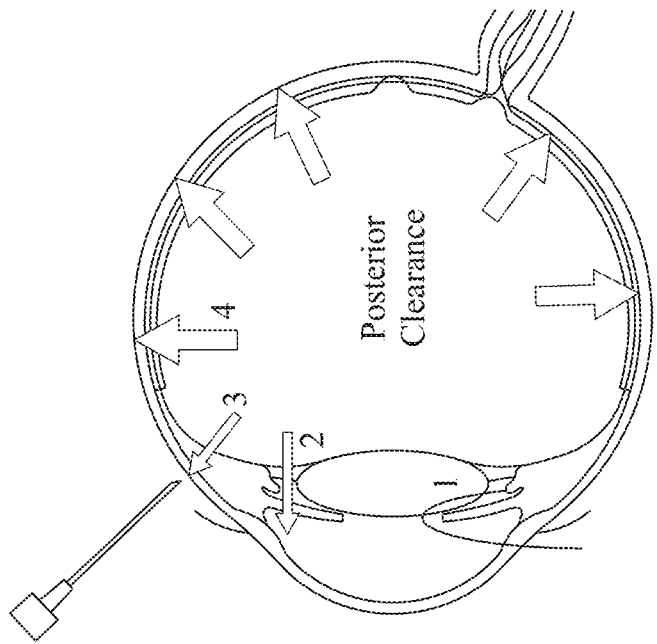
Figure 1B:
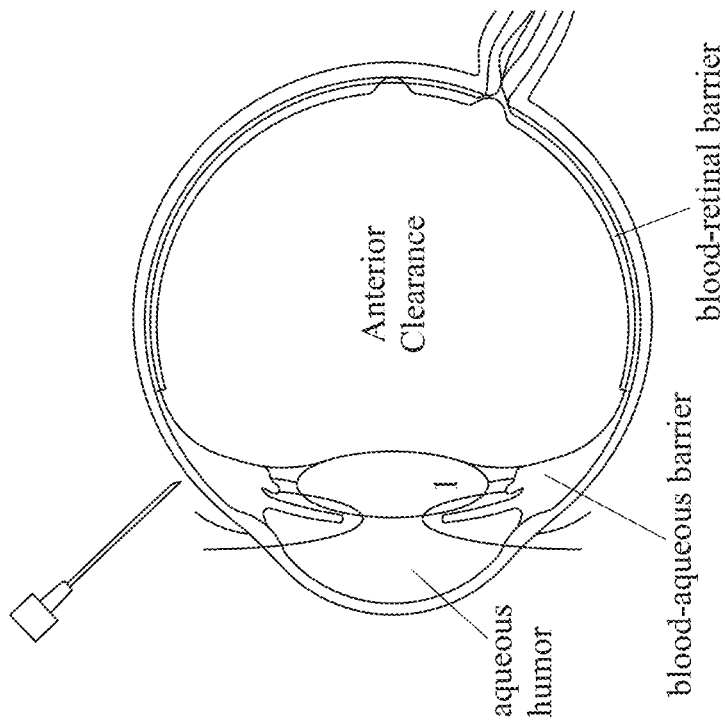

During an injection procedure, a needle tip is positioned at 3 to 4 mm posterior to limbus. This usually enables the drug to exit the syringe tip at a position that is closer to the front of the eye. FIG. 1A illustrates a typical intravitreal injection procedure. Once the drug enters the vitreous chamber, there are two elimination routes anterior and posterior, see FIGS. 1B and 1C. For anterior elimination, the drug must diffuse in the vitreous to gain further access to the aqueous humor. This would then allow the drug to enter the blood stream. The posterior route requires that the drug must diffuse in the vitreous and then cross the endothelia and epithelia of blood-ocular barriers. These barriers are quite selective in determining the type of molecules that can pass. The exact sites of action for VEGF binding activity of the drug are still not known. However, it is anticipated that both diffusion routes (anterior and posterior) can be involved in the drug transport activities. The diffusion speed depends largely on the individual's physiological condition as well as drug molecule weight. As a result, drugs usually have very different delivery speeds in the vitreous humor: small molecule drugs can diffuse much faster, whereas the mobility is restricted for large molecule drugs.

To understand the challenge of the drug mixing process via diffusion, it is helpful to understand the meaning of anti-VEGF agents first. There are a few different anti-VEGF agents that are used for treating eye diseases. Taking bevacizumab as an example, bevacizumab is a recombinant humanized monoclonal IgG1 antibody that contains human framework regions and murine complementarity-determining regions. Bevacizumab has an approximate molecular weight of 149 kDa (RxList, Avastin). Avastin is the brand name for bevacizumab. Avastin (bevacizumab) is a colorless to pale brown solution and is usually supplied in 100 mg and 400 mg preservative-free single-dose vials. For a 100 mg product, it is formulated in 240 mg α,α-trehalose dihydrate, 23.2 mg sodium phosphate (monobasic, monohydrate), 4.8 mg sodium phosphate (dibasic, anhydrous), 1.6 mg polysorbate 20, and Water for Injection, USP. Therefore, water is the main carrier of the drug in the delivery process. Since the majority of the AMD patients are among the older population, their vitreous are usually more fluid-like than gel-like. More details regarding the change in vitreous properties with aging process will be explained below. Overall, the time it takes for drugs to deliver to target tissue via pure diffusion can be approximately estimated by calculating the time it takes for water to diffuse in water. Table 1 below shows a list of empirical diffusion constants.

TABLE 1

Empirical diffusion constants showing the dependence on size and cellular context

| molecule | measured context | diffusion coefficient ($\mu m^2/s$) | BNID |
|---|---|---|---|
| water | water | 2000 | 104087, 106703 |
| oxygen | water | 2000 | 104440 |
| tRNA (≈ 20k Da) | water | 100 | 107933, 107935 |
| protein (≈ 30k Da GFP) | water | 100 | 100301 |
| protein (≈ 30k Da GFP) | eukaryotic cell (CHO) cytoplasm | 30 | 101997 |
| protein (≈ 30k Da GFP) | rat liver mitochondria | 30 | 100300 |

As illustrated in Table 1, the diffusion coefficient of water molecule in water is approximately 2000 $\mu m^2/s$, and the diffusion coefficient for protein of 30 kDa in water is approximately 100 $\mu m^2/s$ (see highlighted boxes).

To estimate the time scale τ for a particle to travel distance x, we can use $\tau \sim x^2/D$. Since the average size of a human eye is 24.5 mm in diameter, $\tau \sim (24.5 \text{ mm})^2/(2000 \ \mu m^2/s)=83$ hrs, which is approximately 4 days. This theoretical calculation is consistent with our experimental observations. In our experiment, we injected water-dissolved dye into water and observed how long it took for the dye/water mixture (1:50 ratio) to travel 10 mm vertical distance. It took about 20 hrs in total, which was as expected.

Figure 2:
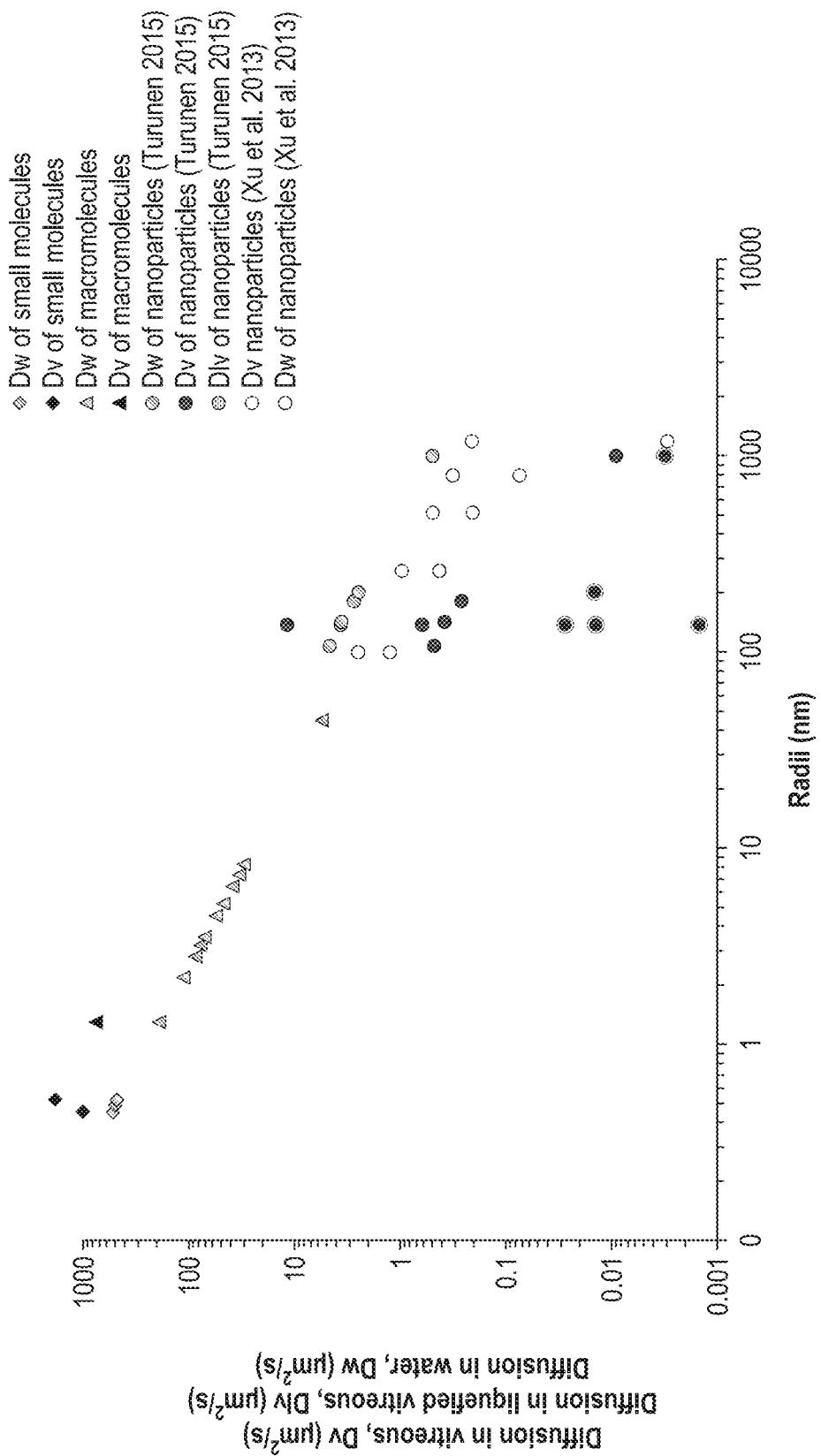
FIG. 2 illustrates diffusion coefficients of molecules and particles in the vitreous humor.

Based on this calculation result, it raises a concern that drug delivery by pure diffusion might be taking too long, given that the vitreous half-life of anti-VEGF is quite limited and can range from a few hours to a few days. In addition, the diffusion coefficient of protein of molecular weight 30 kDa is 100 $\mu m^2/s$ in water, which is much slower than water diffusion in water. Anti-VEGF agents are usually large molecules (>150 kDa). The diffusion rate can be much slower since the mobility of large molecules is usually restricted. FIG. 2 illustrates the diffusion coefficients of molecules and particles in vitreous, liquefied vitreous, and water.

Therefore, to effectively increase injection efficiency, drugs cannot solely rely on diffusion via anterior or posterior diffusion routes, and convection needs to be introduced into the scenario. Additionally, one of the goals of the present application is to promote fluid mixing in the eye in a minimally invasive manner. To summarize the two objectives, they are: 1) to effectively induce convection in the drug delivery process in the eye to accelerate drug transport efficiency; and 2) promote flow circulation in the eye to facilitate better drug mixing for improved treatment efficacy.

There are several different ways to increase drug delivery efficacy in the eye. Clinically, there are four delivery alternatives, which are topical, systemic, implants, and trans-scleral (see FIG. 3). These various methods are either designed in an attempt to bypass the two diffusion routes in the eye or to alleviate the potential side effects.

Figure 3:
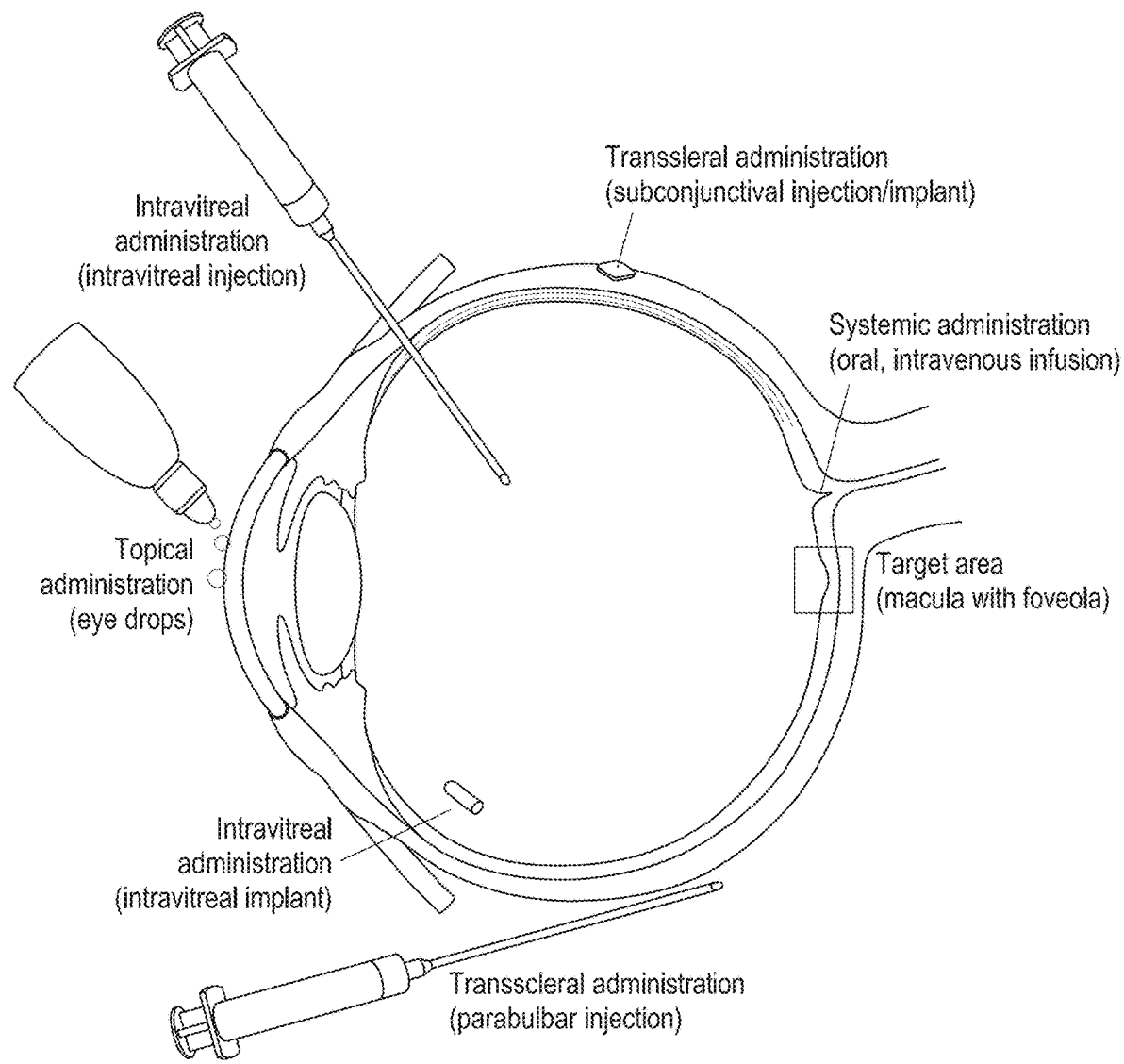
FIG. 3 illustrates various drug delivery methods for treatment of age-related macular degeneration (AMD).

As shown in FIG. 3, the target macula area can be reached via various routes: topical delivery to the surface of the eye, trans-scleral delivery underneath the conjunctiva, direct injection (injection or implant), and systematical delivery via oral tablets. Topical drops must diffuse across a few layers to reach the target tissue, these layers include tear film, cornea, iris, ciliary body, and vitreous. This can severely dilute the fraction of drug reaching the target issue. Systemic delivery such as tablets can result in a poor dose-response profile. Ocular implant takes the same idea as intravitreal injections and thus may also benefit. Trans-scleral administration injects drugs via a region surrounding the eye and experiences the same issue that exist in topical administration: the overall retinal bioavailability is very low (in the range of 0.1%) after such an administration, which is not an ideal choice for retinal drug delivery. Overall, intravitreal injection is so far the mostly practiced as well as the most effective treatment for retinal drug delivery.

Drug Delivery & Experimental Design

There are four basic types of eye movements: saccades movements, smooth pursuit movements, vergence movements, and vestibule-ocular movements. Saccades movements are rapid movements and the eyes abruptly change the point of fixation during such movements. In daily life, saccades movements of the eye happen in many scenarios, ranging from small movements made during reading and large movements made when a person is simply looking around. It can also occur during sleep.

Smooth pursuit movement is much slower compared with saccades movement. It facilitates voluntarily tracking a moving stimulus. Vergence movement is quite different than the other two in the sense that it is disconjugated, which means eyes can move in different directions.

Vestibule-ocular movements compensate for head movements so the eyes are stabilized relative to the external world, which can help with stabilizing visual images on the surface of the retina when the head moves. These four movements can essentially be broken down into three fundamental motions: rapid lateral motion, rotating motion, and slow lateral motion. The human eye has a complicated structure. Instead of trying to reproduce every single detail in the eye, it is important to grasp the most important features to acquire critical insights experimentally. The content below explains the main structural challenges that people see in human eyes as well as selection criteria when the eye model was built for this writing.

Figure 4:
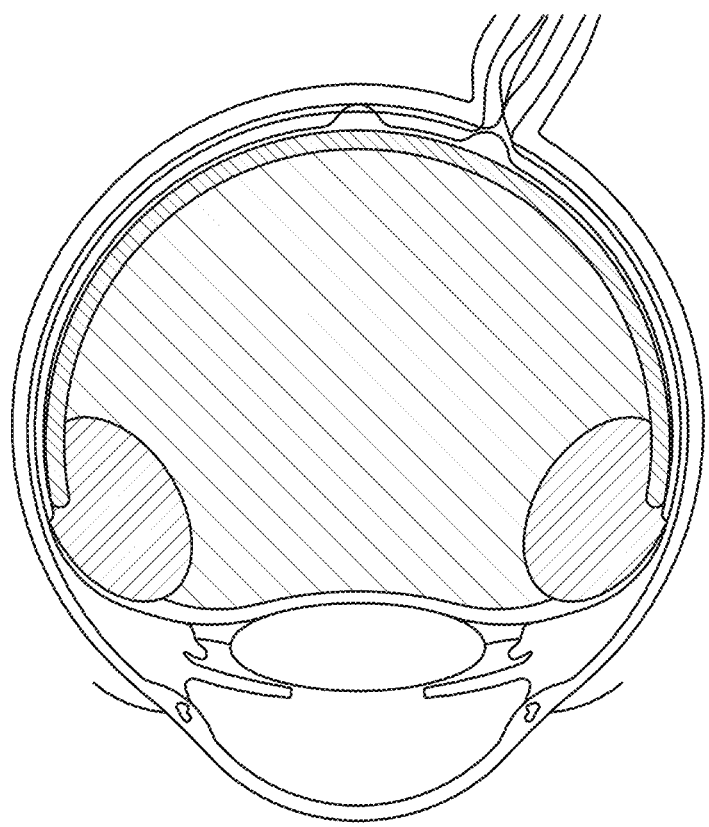
FIG. 4 illustrates variations in concentrations in the vitreous.

FIG. 4 illustrates variations of vitreous concentration. As shown, hyaluronic acid and collagen are not uniformly distributed within the vitreous. The highest concentration is in vitreous cortex, which is the region that is the closest to retina. The central area (central vitreous) is more liquid like, followed by basal vitreous. Vitreous humor is composed of 98% to 99% water and 1% other ingredients. This 1% other ingredients, the majority of which are collagen and hyaluronan, has various distribution in different regions of the eye. For the drug to reach the retina via the posterior route, it must first travel across the central vitreous chamber and then pass the vitreous cortex to reach the back of the eye. Further, even by considering the anterior route, the drug still needs to diffuse through the vitreous to join the aqueous flow. Therefore, effectively promoting drug mixing in the eye can potentially facilitate drug eliminations via both routes.

Components of human vitreous change consistently as people age. As shown in Table 2 below, vitreous is a 100% gel solution at birth and liquefaction gradually happens with age. This is one factor that explains the discrepancy in treatment efficacy among various individuals. Many other factors include ethnicity, genetics, and special procedures performed (for example, vitrectomy).

TABLE 2

Change in gel and liquid volume of the human vitreous with age

| Age (years) | Gel volume (cm$^3$) | Liquid volume (cm$^3$) |
| --- | --- | --- |
| Birth | 1.6 | 0 |
| 5 | 3.3 | 0 |
| 10 | 3.5 | 0.7 |
| 20 | 3.9 | 0.9 |
| 30 | 3.9 | 0.9 |
| 40 | 3.9 | 0.9 |
| 50 | 3.5 | 1.3 |
| 60 | 3.2 | 1.6 |
| 70 | 2.8 | 2.0 |
| 80 | 2.5 | 2.3 |
| 90 | 2.2 | 2.6 |

Based on the two above-mentioned structural challenges, one parameter to look at is the effect of density/viscosity difference between the injected drug and the vitreous to understand how drug flow proceeds in various environments. Since regional distributions of liquid and gel components are unclear and it obviously differs case by case, we start with a vitreous model of uniform density/viscosity distribution to get a generalized understanding. Generally, the viscosity of human vitreous is two to four times greater than water.

During a vitrectomy procedure, vitreous humor of the patient being treated can be entirely replaced with 0.9% saline solution. This automatically gives the patient being treated "liquid-like vitreous humor. Generally, the vitreous humor is more liquid-like than gel-like for people of 50 years and older. Accordingly, in some embodiments, a 0.9% saline and glycerol/water mixtures at various weight ratios were used to make "vitreous humor" for experimentations. A summary of these material properties can be found in Table 3 below.

TABLE 3

Material properties of vitreous and materials used in the current study

| Material | Viscosity (mPa s) | Density (kg m$^{-3}$) | Thermal expansion coefficient (at 20° C.) | Refractive index | Coefficient of thermal conductivity (W mK$^{-1}$) |
|---|---|---|---|---|---|
| Water | 0.9 | 1000.0 | 0.000210 | 1.000 | 0.6 |
| Saline | 1 | 1063.3 | — | 1.335 | 0.6 |
| Human vitreous | 1-3.6 | 1005.3-1008.9 | — | 1.337 | 0.594 |
| Glycerol 20.2 wt % | 1.7 | 1046.8 | 0.000315 | 1.357 | 0.556 |
| Glycerol 33.6 wt % | 2.7 | 1081.5 | 0.000385 | 1.375 | 0.515 |
| Glycerol 11.2 wt % | 1.3 | 1024.5 | 0.000255 | 1.346 | 0.591 |

During an intravitreal injection session, an ophthalmologist may use a 27 gauge or 30 gauge needle to inject approximately 50 microliters of drugs into the vitreous chamber of a patient's eye. The injection position is usually 3 to 4 mm posterior to limbus and target at the central region. Given that the average diameter of the eye is around 24-mm, the injection spot is quite close to the front of the eye. Therefore, it might not be an ideal entry spot for effective drug delivery in the eye. Furthermore, human eye size varies case by case, so if the same protocol is performed for every individual, the treatment efficacy could certainly vary.

Additionally, besides lateral movements, the effects of varying injection sites on drug mixing profiles was also explored. Three injection sites were studied: side injection (which is similar to the actual intravitreal injection process), center injection (which is more towards the center and more in depth), and bottom injection (which is the deepest among the three).

Many physiological challenges are associated with human eyes including variations in concentrations across different parts of the eye, changes to eye composition with aging, multiple clearance routes, etc. Accordingly, it is important to keep those challenges in mind when selecting features of interest to be included in the eye model design.

Figure 5:
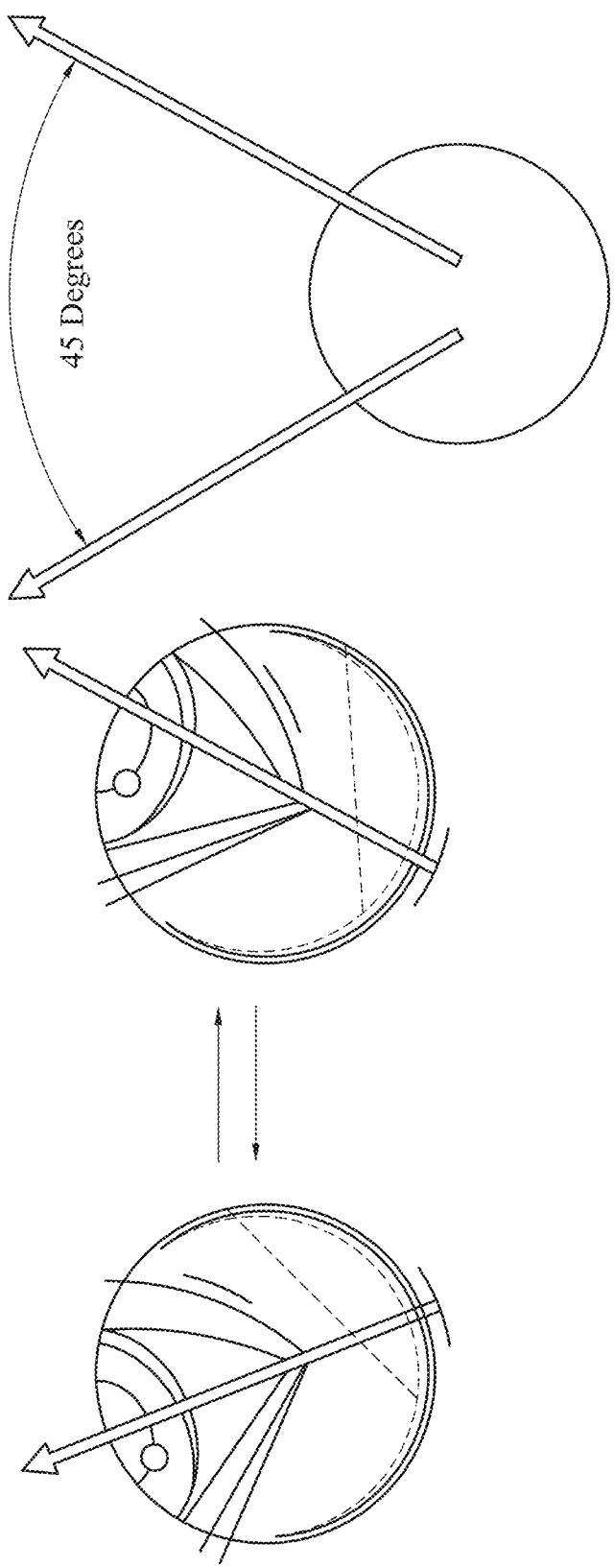
FIG. 5 illustrates an eye lateral movement method for inducing drug flow in accordance with some embodiments of the presentation disclosure.

There are four types of basic eye movements: saccades movements, smooth pursuit movements, vergence movements, and vestibule-ocular movements. Essentially, there are three major types of motions involved in all the movements: rapid lateral motion, rotating motion, and slow lateral motion. Thus, the lateral eye movement at a low frequency is the target eye motion in accordance with the improved methods for intravitreal injection. Lateral movement is essentially moving eyes horizontally back and forth between left and right. Movement magnitude and frequency are usually based on voluntary decisions. In some embodiments, the lateral movement can be 45 degree in its sweep angle and 1 cycle per second (1 Hz) for the movement frequency. FIG. 5 illustrates this motion, which is slow enough for a post-surgery patient to perform in a comfortable manner. FIG. 5A demonstrates an eye looking to the left and the red arrow indicates the center of the eye globe. FIG. 5B demonstrates the eye looking to the right and the orange arrow indicates the center of the eye globe in. During this voluntary lateral movement, the eye moves back and forth between FIGS. 5A and 5B at 1 Hz. The sweep angle is 45 degree, which is demonstrated in FIG. 5C.

Figure 6A:
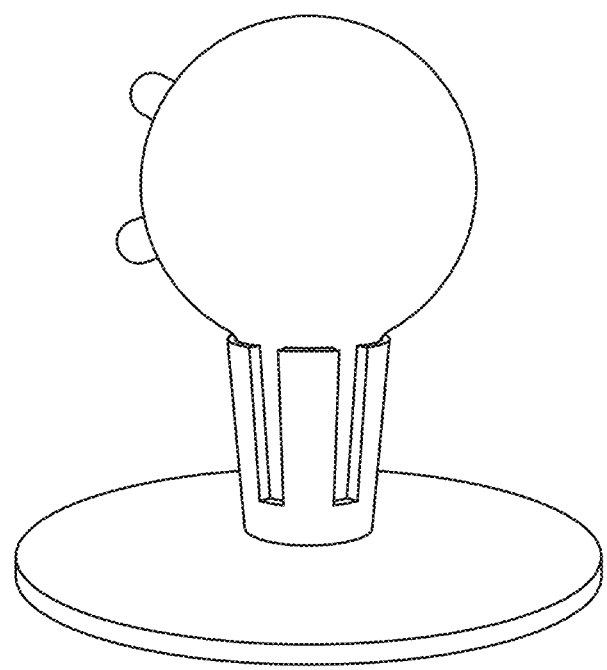
FIGS. 6A-6B illustrate an eye model in accordance with some embodiments of the presentation disclosure.
Figure 6B:
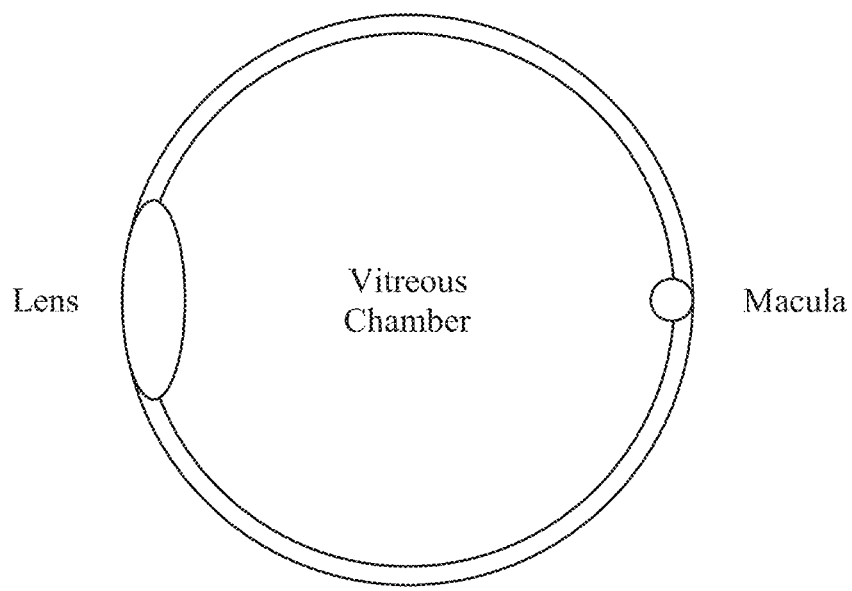

In some embodiments, the eye model can be a glass sphere with approximately a diameter of 1-inch (24.5 mm) (FIGS. 6A-B). Its size is the same as the average size of a human eye. For a liquid-like vitreous medium, the DI water and salt mixture (0.9% saline) was chosen. This mixture resembles general eye properties among older populations whose vitreous are more fluidic than gel-like. This is especially true for a patient undergoing vitrectomy, whose vitreous is replaced with 0.9% saline solution.

To prepare for the 0.9% saline solution that is used throughout the experiments to represent liquid-like vitreous humors, the solution is prepared in bulk (1 L) and stored at room temperature overnight. The bottle was shaken well before each use to ensure an even distribution of salt in the solution. This enables the assumption that the solution property is consistent across all the experiments.

In some embodiments, the second choice for vitreous humor is a glycerol and water mixture with a 1 to 5 ratio (20.2 wt %), which was used to examine the viscosity effect on the fluid mixing pattern. Table 4 is revisited below to remind the audience of material properties. Glycerol 33.6 wt % and Glycerol 11.2 wt % are used to represent drugs that are either heavier/more viscous or lighter/less viscous than the vitreous humor.

TABLE 4

Material properties of vitreous and materials used in the current study

| Material | Viscosity (mPa s) | Density (kg m$^{-3}$) | Thermal expansion coefficient (at 20° C.) | Refractive index | Coefficient of thermal conductivity (W mK$^{-1}$) |
|---|---|---|---|---|---|
| Human vitreous | 1-3.6 | 1005.3-1008.9 | — | 1.337 | 0.594 |
| Glycerol 20.2 wt % | 1.7 | 1046.8 | 0.000315 | 1.357 | 0.556 |
| Glycerol 33.6 wt % | 2.7 | 1081.5 | 0.000385 | 1.375 | 0.515 |
| Glycerol 11.2 wt % | 1.3 | 1024.5 | 0.000255 | 1.346 | 0.591 |

Figure 7:
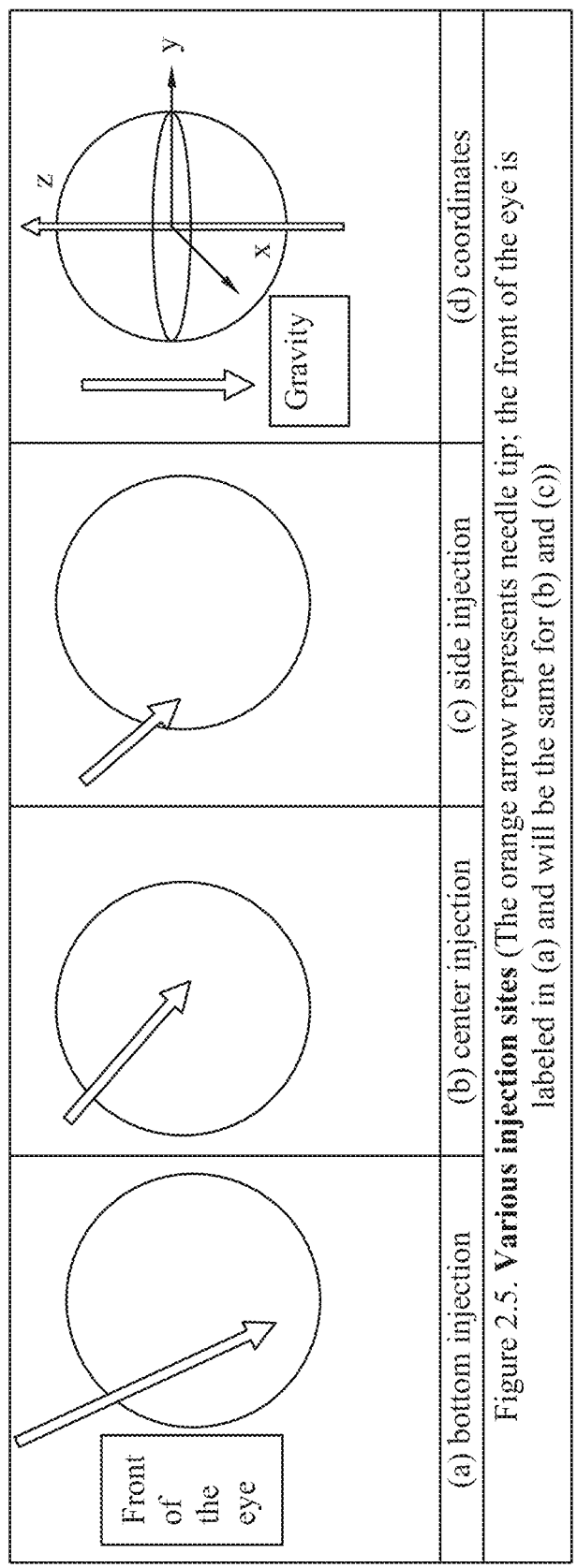
FIG. 7 illustrates various injection sites for treating AMD.

In some embodiments, intravitreal injection procedure performed by ophthalmologists in the clinic as well as the modified protocol in this study is summarized in Table 5 below. The detailed position of each injection site is demonstrated in FIG. 7. As mentioned before, the side injection is the closest to an ophthalmologist's injection behavior, whereas the center and bottom injection positions are more in-depth.

TABLE 5

Intravitreal Injection Protocol Performed In The Clinic vs. Modified Protocol In This Study

Figure 10:
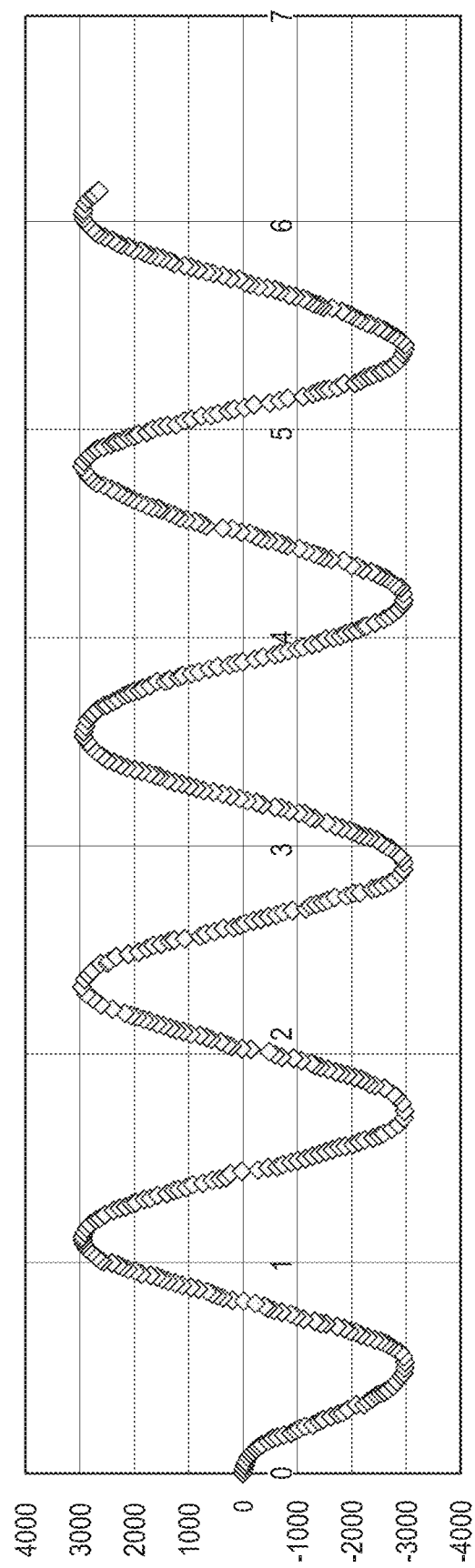
FIG. 10 illustrates a plot of the actual motor trajectory.

| | Our Protocol | Ophthalmologist's Protocol |
|---|---|---|
| Needle | 21 Gauge needle | 27 Gauge or 30 Gauge needle |
| Injection duration/frequency | 100 microliter injection over the course of one minute | 50 microliter injection every four weeks |
| Injection site | bottom, center, and side (FIG. 10) | 3 to 4 mm posterior to limbus, avoid meridian horizon, target the central region |

In some embodiments, digital particle imaging velocimetry (DPIV) technique was used to quantitatively map the fluid field. Fluorescence materials were mixed with the solution of interests to assist with flow visualization. A series of flow images were taken during a visualization session and the resulting images were cross correlated using commercial software such as, but not limited to, PIV3CView (PIVTEC). Quantitative results such as velocity field could thus be obtained.

In some embodiments, the DPIV system can include a convex lens to spread the laser beam in a vertical direction so that the camera can visualize a thin sheet of the entire globe. The laser beam can be calibrated to pass through the center of the eye model. This enables flow profiles on a 2D plane of a 3D object to be observed. In our study, a 445-nm blue laser was used to illuminate the particle laden flow field (laser model: Skye 100-mW handheld 445-nm focusable blue laser pointer with dual lock). The flow images were captured by a camera with a resolution of 640 by 480 pixel (IPX-VGA210-L; 90 mm Tamron Lens, Saitama, Japan; Sony Alpha-7) at 10 frame per second (fps). The camera setting was adjusted using the free software, LYNX GigE Application. A majority of the parameters were set at their default values, with a few modifications summarized in Table 7 below.

There were two types of fluorescence materials used in this experiment: fluorescence particle and laser-induced fluorescence (LIF, which is a dye). Both materials can be excited by a laser of a given wavelength. Mixing fluorescence particles (manufactured by Kodak Company) with the solution of interests can mark the fluid flow motion. Fluid flow images were then captured and PIV analysis was performed on the resulting images to obtain velocity profiles. These velocity profiles were later analyzed for making particle pathline visualizations. Using LIF (fluorescein) for visualization allowed us to observe the dynamic mixing process in the eye model. Solution that carries fluorescein (drug) was injected into the solution without fluorescein (vitreous humor). By quantitatively analyzing fluorescein light intensities, the drug trajectory as well as the amount of drugs that reached the target issue at different time stamps was quantified.

Before a visualization, the two fluorescence materials were mixed with either 0.9% saline or glycerol/water mixture (Glycerol 20.2 wt %). Fluorescence particles were carefully selected to have the same density and diffusivity as the solution so the particle movements were representative of flow motion. In some embodiments, fluorescence particles were selected to have a density close to 0.9% saline. Fluorescein was added to 0.9% saline or glycerol/water mixture at the ratio of 1:50 (fluorescein to solution ratio). This assumes that any possible changes to physical properties of the solution due to addition of fluorescein were negligible.

PIV Visualization System

Figure 8:
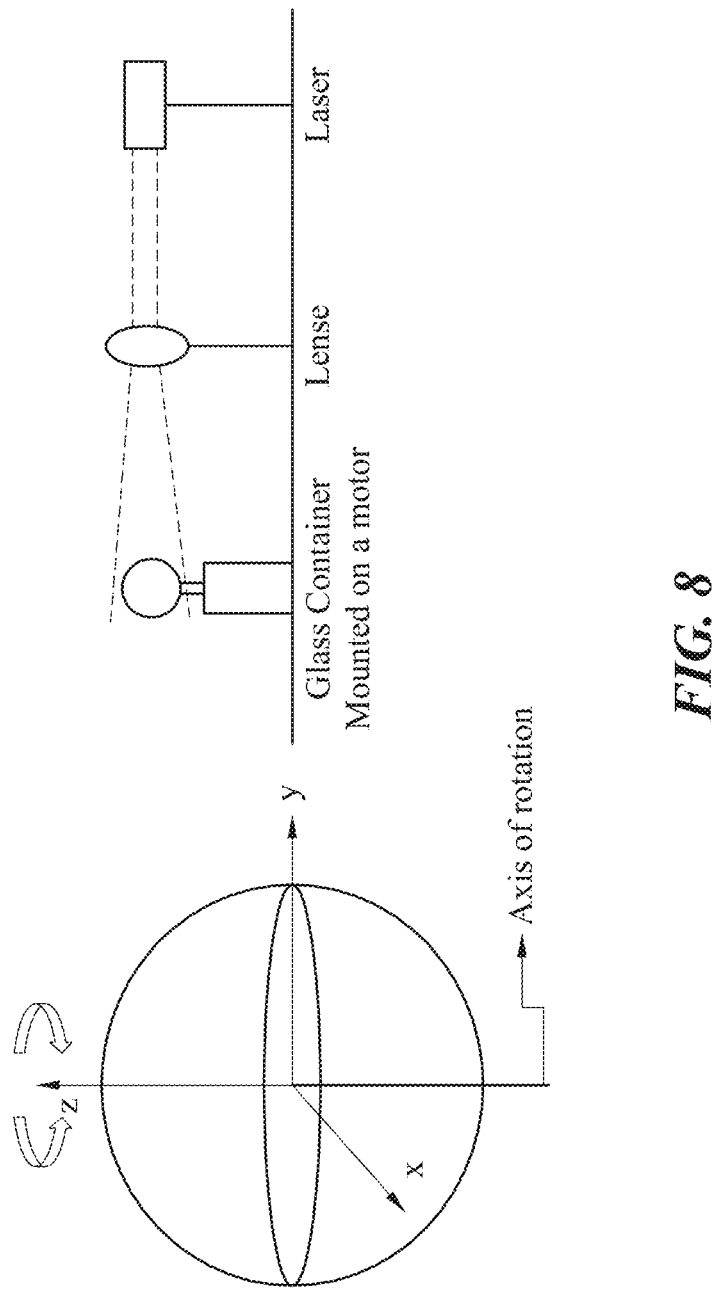
FIG. 8 illustrates a system for PIV visualization in accordance with some embodiments of the presentation disclosure.

FIG. 8 illustrates a PIV visualization system 800 in accordance with some embodiments of the present disclosure. System 800 can include a blue-violet laser for exciting fluorescence materials, a convex lens to spread the laser beam into a laser sheet, a camera for capturing flow images, an eye model, and a motor-magnet coupler to induce lateral movements at a fixed pattern. The blue-violet laser can have a wavelength of 445 nm, ±50 nm. Once the flow images are generated using system 800, they can be analyzed using software such as, but not limited to, PIVview with the following parameters as summarized in Table 6 below. The camera settings can be to values summarized in Table 7. The flow measurement was valid up to approximately 1 mm/s, which was the velocity at which an object moved one pixel during the exposure time.

TABLE 6

Parameters used in PIVview software for Particle Image Velocimetry (PIV) analysis

| | |
|---|---|
| Image Pair Offset | 3 |
| Pixel Windows Size | 32 by 32 |
| Overlap | 16 pixel |
| Fast Fourier Transform Correlation | Standard |
| Maximum Displacement Limit | 16 pixel |
| Multi-pass Interrogation | |
| Median Filter with 3 by 3 Kernel Size | |

TABLE 7

Specified camera settings in LYNX GigE A3plication

| | |
|---|---|
| Exposure Time | 10 fps |
| Shutter Time | 5000 |

Figure 9:
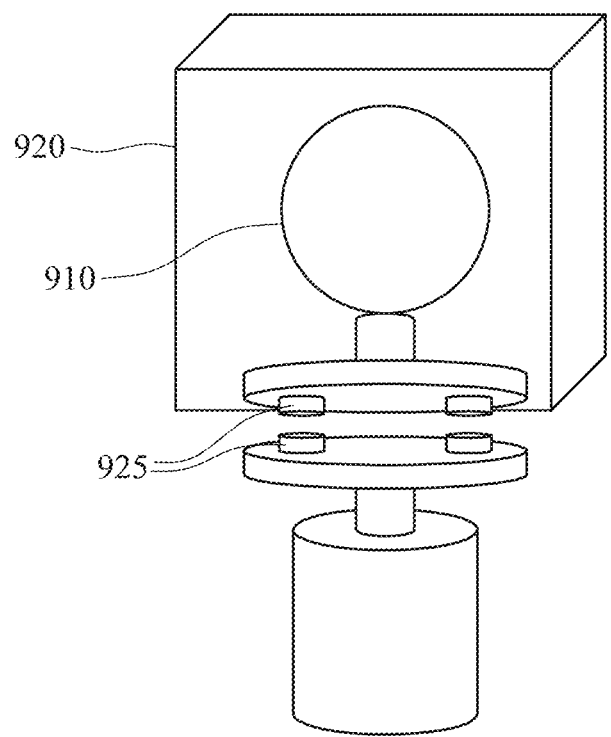
FIG. 9 illustrates the motor-magnet assembly in accordance with some embodiments of the presentation disclosure.

FIG. 9 illustrates a motor magnet coupler 900 in accordance with some embodiments of the present disclosure. Coupler 900 can have three major components: a DC motor, holder set for holding eye model 910, and four magnets 925. The top part of the holder set is designed to hold the eye model and was entirely immersed in a small fluid tank. Fluid that was added into the tank was the same as the fluid that filled the eye model. This ensured that both fluids had the same refractive index and thus no distortions when laser beam passed through the curvature of the eye model. The holder set can be 3D printed. The motor can be a Maxon DC Motor EC 90 Flat Series.

The bottom part of the holder set sat on top of the motor, which was controlled by EPOS motor controller and LabVIEW. LabVIEW program sent out signals to control the movement of the motor, which also drove the motion of the bottom part of the holder set. (Again, for lateral movements in our study: 45 degree sweep angle at 1 Hz.) The two magnets that were fixed on the bottom holder drove the motions of the two magnets that were fixed on the top holder, and thus the movement of the eye model. The actual motor movement was recorded throughout the experiment. This allowed for tracking and checking the actual motor trajectory during and after each experiment (see FIG. 10).

As previously mentioned, laser-induced fluorescence could assist with the observations of drug mixing profile in the eye model. In some embodiments, fluorescence in a 0.9% saline mixture of 100 microliters were slowly injected into the eye model that was filled with 0.9% saline at the desired injection spot using a syringe pump. The entire injection process can take about 1 min in total, which was very slow and did not cause the drug to splash inside the eye model. This injection process reproduced the intravitreal injection procedure of injecting microliter-scale of drugs (fluorescein/saline mixture in our study) into the vitreous humor (0.9% saline in our study).

Experimental Results

Figure 11:
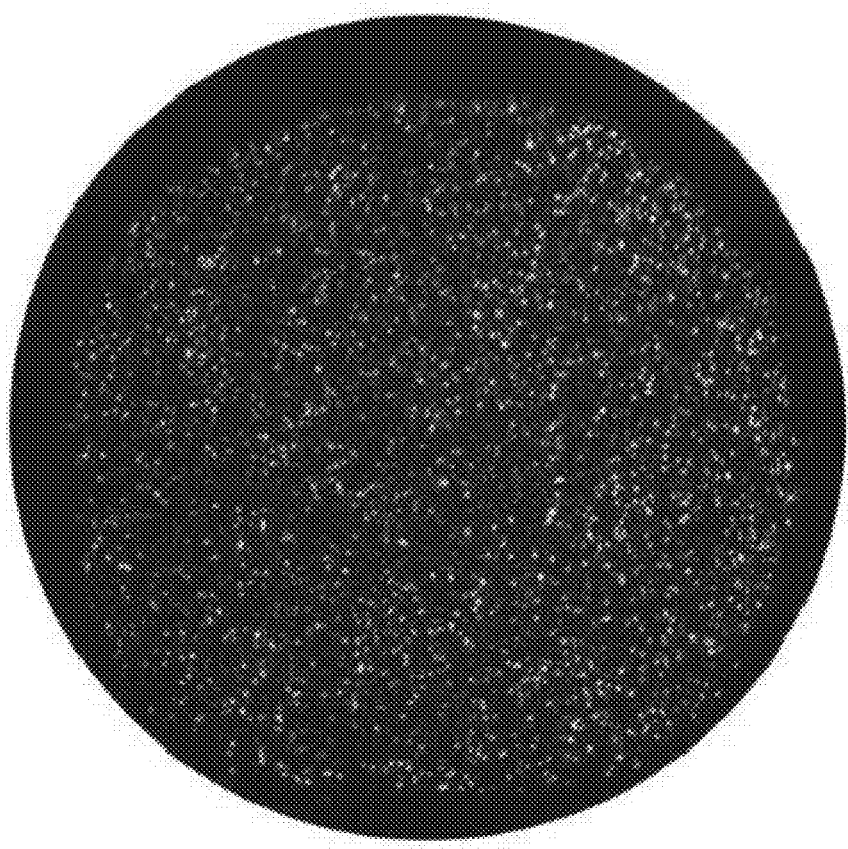
FIG. 11 illustrates an example image captured during a PIV visualization session in accordance with some embodiments of the presentation disclosure.

FIG. 11 illustrates an image captured during a PIV visualization session in accordance with some embodiments of the present disclosure. The white dots are fluorescence particles excited by the 445-nm blue laser light. Note that we wanted to observe fluid motions after the lateral movement stopped. This could help with understanding the duration of mixing after each set of movements. Therefore, during a PIV visualization session, image capturing began before the eye model started to rotate and stopped after the fluid motion completely decayed. However, during a PIV analysis session, only images taken after the eye rotation stopped were analyzed. This also ensured that PIV analysis was performed on the same 2D plane because the visualization plane kept switching when the eye model was moving. In our study, we made comparisons between 5 cycle rotations (rotating a full cycle for five times) versus 10 cycle rotations (rotating a full cycle for ten times).

Figure 12:
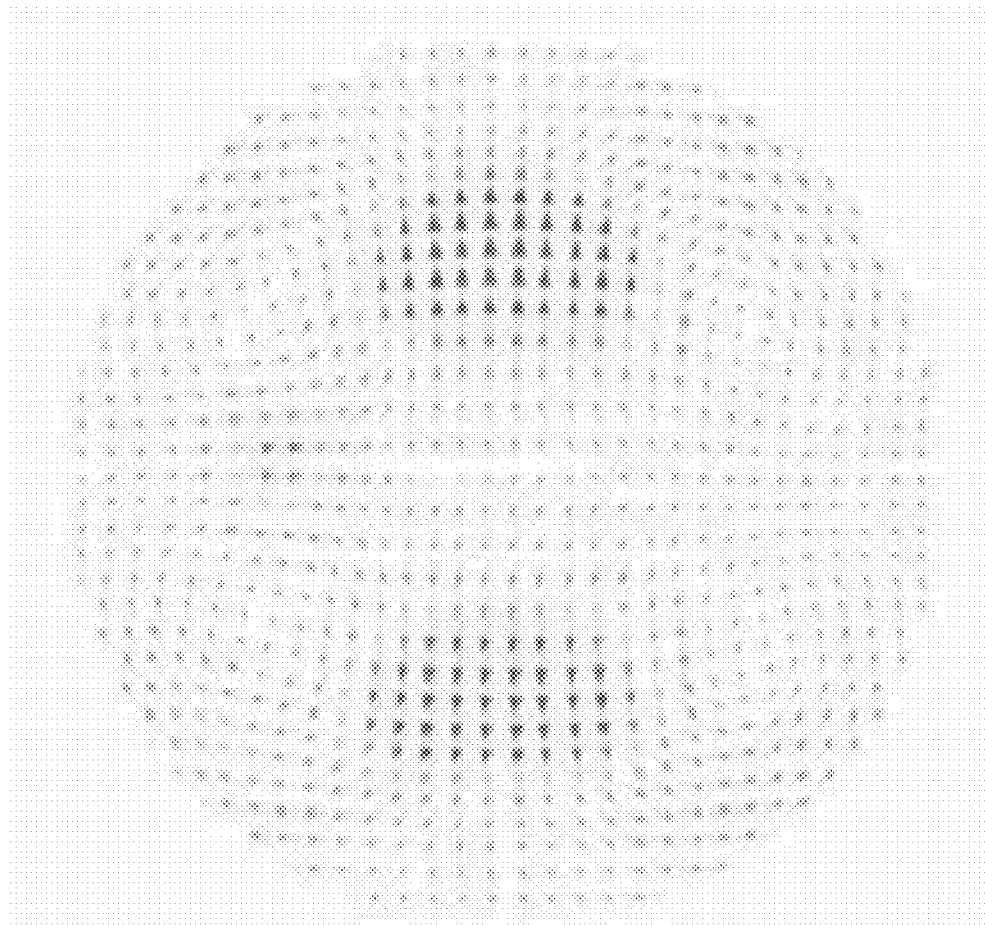
FIG. 12 illustrates the average velocity field of the PIV visualization session done in FIG. 11 in accordance with some embodiments of the presentation disclosure.
Figures 13A, 13B:
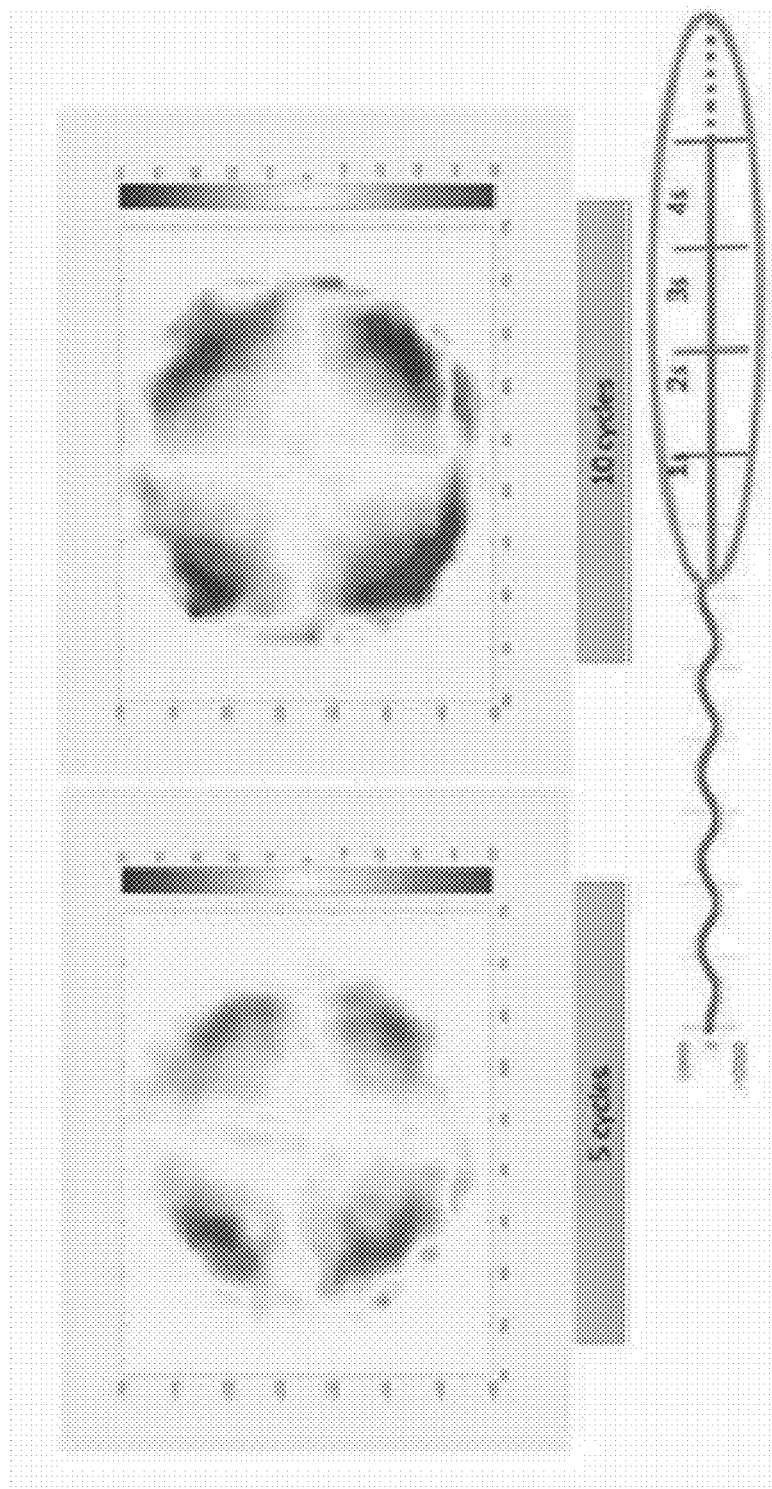
FIGS. 13A and 13B illustrate vorticity plots generated in accordance with some embodiments of the presentation disclosure.

FIG. 12 illustrates the average velocity vector field 1200 (obtained from a PIV analysis) after five cycles. Based on velocity vector field 1200, four circulations were formed during the rotation of the eye model. These circulations were sustained for a period of time after the rotation of the eye model stopped. FIGS. 13A and 13B illustrate vorticity plots for 5 and 10 cycles, respectively, in accordance with some embodiments of the present disclosure. The 5 and 10-cycle vorticity plots can help understand whether the duration that circulations sustained was different between less movements (5 cycles) and more movements (10 cycles). As shown in FIGS. 13A-B, the vorticity appeared to be stronger after 10 cycles movements as compared with 5 cycles movements. The circulations also sustained for a bit longer after 10 cycles movements. It also worth noting that circulations sustained for quite a short duration in both cases: approximately 5 seconds after 5 cycles movements and 10 seconds after 10 cycles movements.

FIG. 14 illustrates a particle pathline visualization chart for understanding the actual particle trajectory. After performing PIV analysis on raw images using the software (e.g., PIV3CView), files containing flow field information were obtained. Because the flow images were taken at a programmed rate of 10 frames per second, these files were also ordered in a sequential manner. Important flow information contained in these files includes physical coordinate (x,y), velocity components (x,y), velocity gradient (du/dx, du/dy, dv/dx, dv/dy), and vorticity component.

Using the velocity field information, the Lagrangian path of fluid flow can be tracked to create a pathway visualization using a simulation software (e.g., MATLAB). At first, locations of particles of interests were defined to obtain and plot the initial position. Then the files containing velocity field were referred at each instance of time to plot the following positions. This same process was repeated over a certain period of time. This is essentially the same as overlaying a sequence of actual particle images onto a single image.

Figure 15:
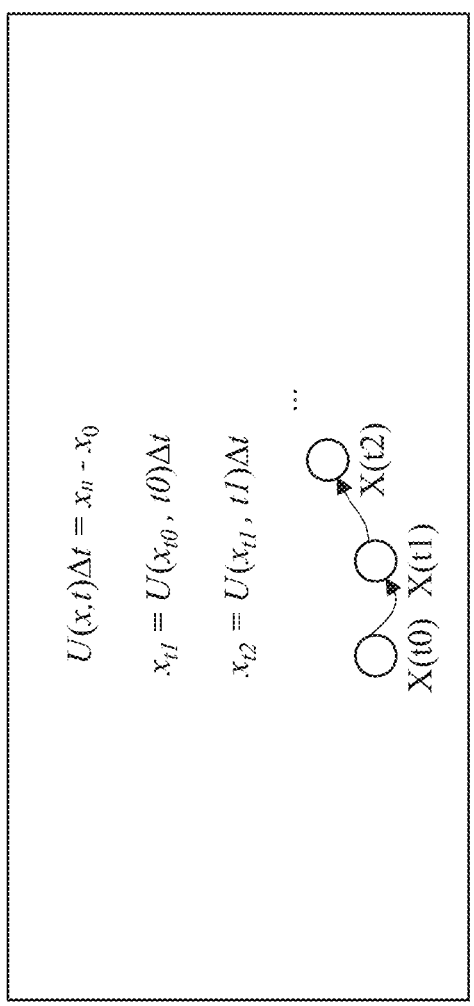
FIG. 15 illustrates pathline visualization algorithms used to generate PIV visualizations in accordance with some embodiments of the presentation disclosure.

FIG. 15 illustrates the mathematical formulas used to determine the velocity field in accordance with some embodiments of the present disclosure. Those formulas are also reproduced below.

$$U(x,t)\Delta t = x_n - x_o \tag{1}$$

$$x_{t1} = U(x_{t0}, t_0)\Delta t \tag{2}$$

$$x_{t2} = U(x_{t1}, t_1)\Delta t \tag{3}$$

In the above formulas, U is the velocity, which is a function of position (x) and time (t). $\Delta t$ is the time interval between two adjacent images captured. $T_0$ is the initial time, $T_1 = T_0 + \Delta t$, and so on. After determining the initial position, the next position at $T_1$ is calculated based on the velocity field of the previous position (which is $U(x_0, t_0)$ in this case). This gives the particle position at $T_1$. The same procedure is used at successive time steps to generate the pathway field of the following positions. In this way, pathways of particles are obtained.

Figure 16:
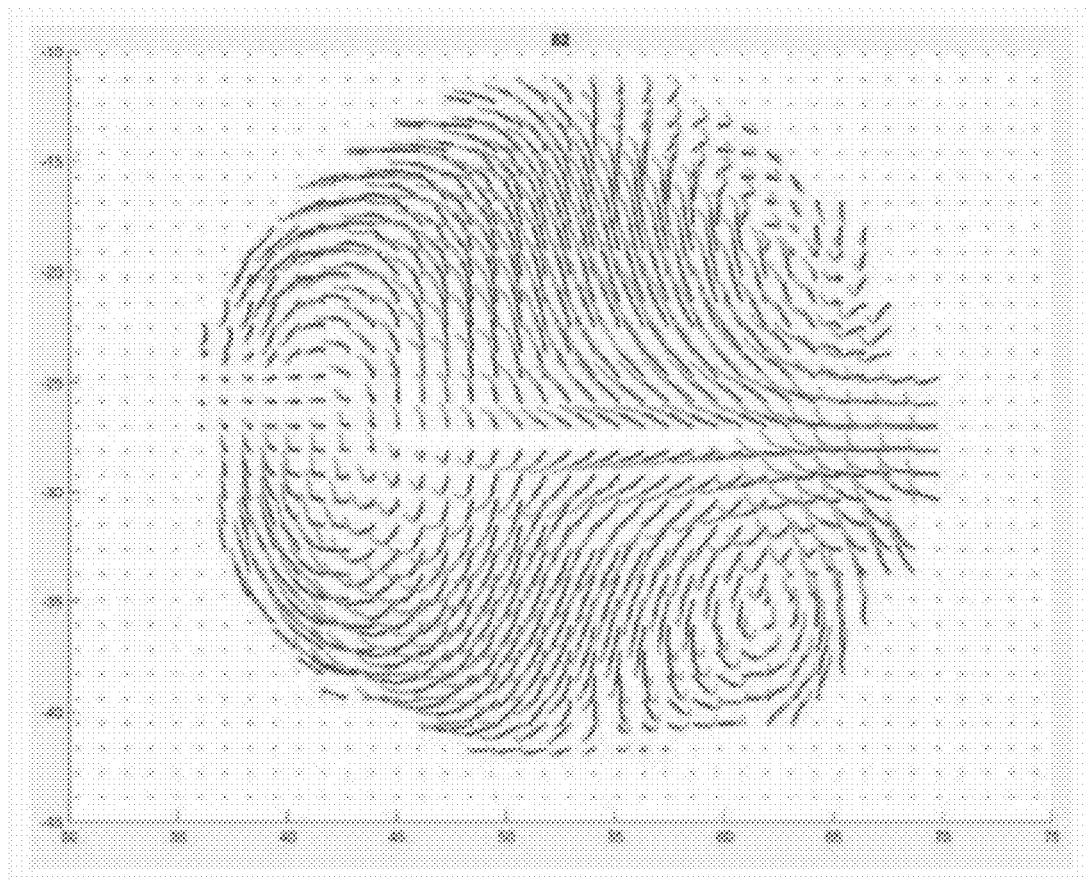
FIG. 16 illustrates a pathline visualization generated using at least the algorithms shown in FIG. 15 in accordance with some embodiments of the presentation disclosure.

FIG. 16 illustrates a pathline visualization chart 1600 generated using the formulas in FIG. 15 in accordance with some embodiments of the present disclosure. Chart 1600 demonstrates the particle trajectories in a total of 8 seconds after 10 cycles lateral movements. Again, the particle pathway tracking begins after the rotation stops and ends when circulations completely decay. In FIG. 16, the beginning of the time is color-coded in dark blue, then green, and finally light blue.

Figure 17:
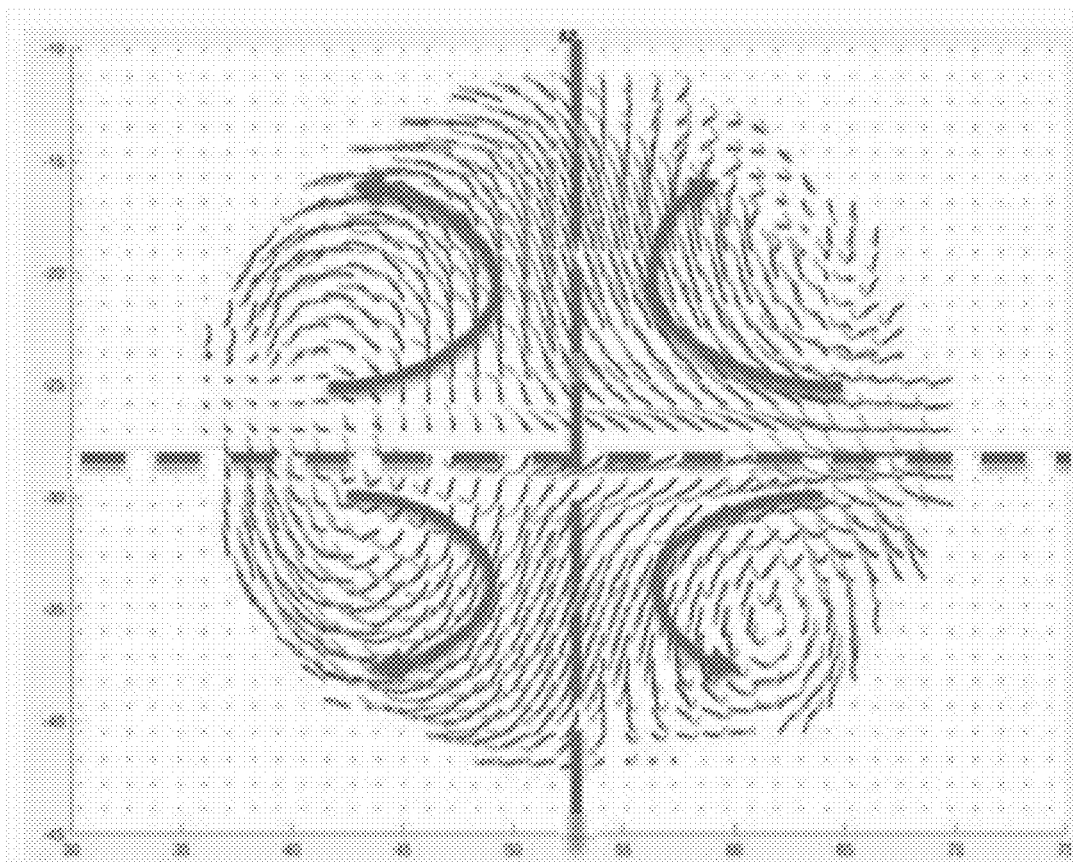
FIG. 17 illustrates a pathline visualization, generated in accordance with some embodiments of the presentation disclosure, showing circulations in each quadrant of the eyeball.

FIG. 17 illustrates a pathline visualization chart 1700 showing the main circulation pathways of a simulated vitreous humor in accordance with some embodiments of the present disclosure. Chart 1700 shows flows in each of the four quadrants, which is consistent with the observations from the vorticity plots in FIGS. 13A-B. One important observation derived from the pathline visualization charts and vorticity plots is that the initial position of the particle is very likely to affect the final position of the particle.

Figure 18:
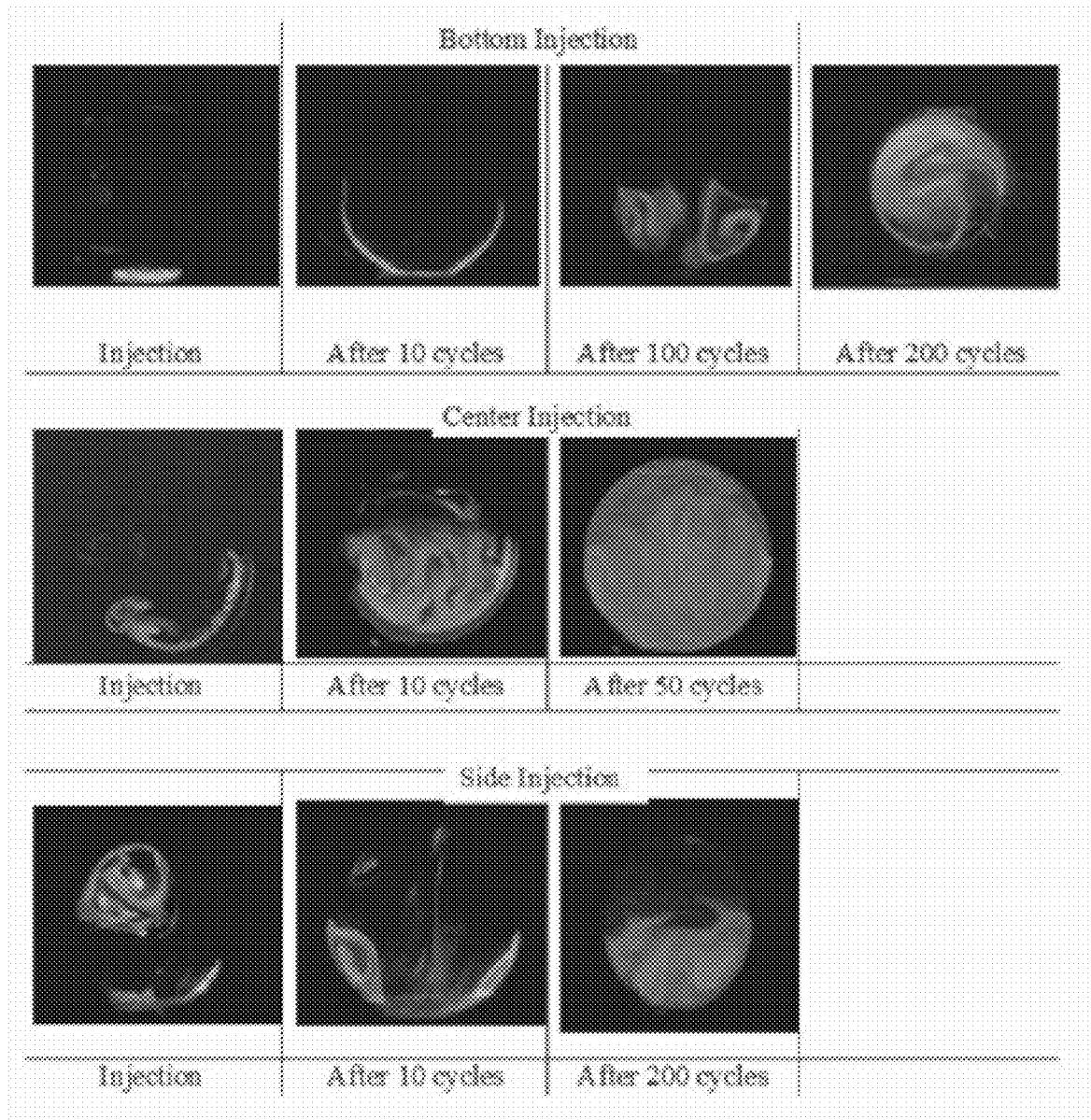
FIG. 18 illustrates dye visualization images from varying injection sites.

To understand whether injecting drugs at different sites can make a difference to the final drug mixing profile, a LIF visualization experiment was performed. Drugs (mixture of 0.9% saline and fluorescein) were injected at the bottom, center, and side locations of the eye model. In this set of experiments, the eye model went through a series of 10 cycles lateral movements intermittently. Intermittent can include, for example after the initial injection, the eye model was rotated for 10 cycles. Next, the magnitude of drug mixing was then observed and recorded by the camera before another 10 cycles of rotations was performed. This process was repeated until drugs were well mixed in the entire chamber. The resulting images were summarized in FIG. 18, which illustrates variations in dye (drug) distribution by injection site. By examining the images carefully, it was obvious to see that center injection took the shortest amount of time as well as the least amount of movements for the drug to mix well in the eye. Bottom injection and side injection took a longer duration and more movements to achieve complete drug mixing in the eye.

As previously mentioned, human eye's vitreous humor property varies among different individual and changes as a person ages. To study the effect of solution property on the mixing process in the eye, glycerol and water are mixed together to generate a series of solutions with various viscosity and density. Accordingly, in some embodiments, the glycerol/water mixture can be used in place of 0.9% saline to help understand whether lateral movements can also promote drugs mixing in a vitreous humor that is more gel-like. After injecting drugs (glycerol/water/fluorescein mixture) into the eye model (filled with glycerol/water mixture), 10 cycles of lateral movements were introduced to the eye model in the "lateral rotation" experiment. A flow image was taken at every 10 mins for 30 mins in total. Overall, observations were made at the following five instances of time: the moment right after injection, the moment right after lateral movements stop, 10 mins after injection, 20 mins after injection, and 30 mins after injection. The same process was repeated in the "no rotation" experiment, although no rotation was involved in this process.

Figure 19:
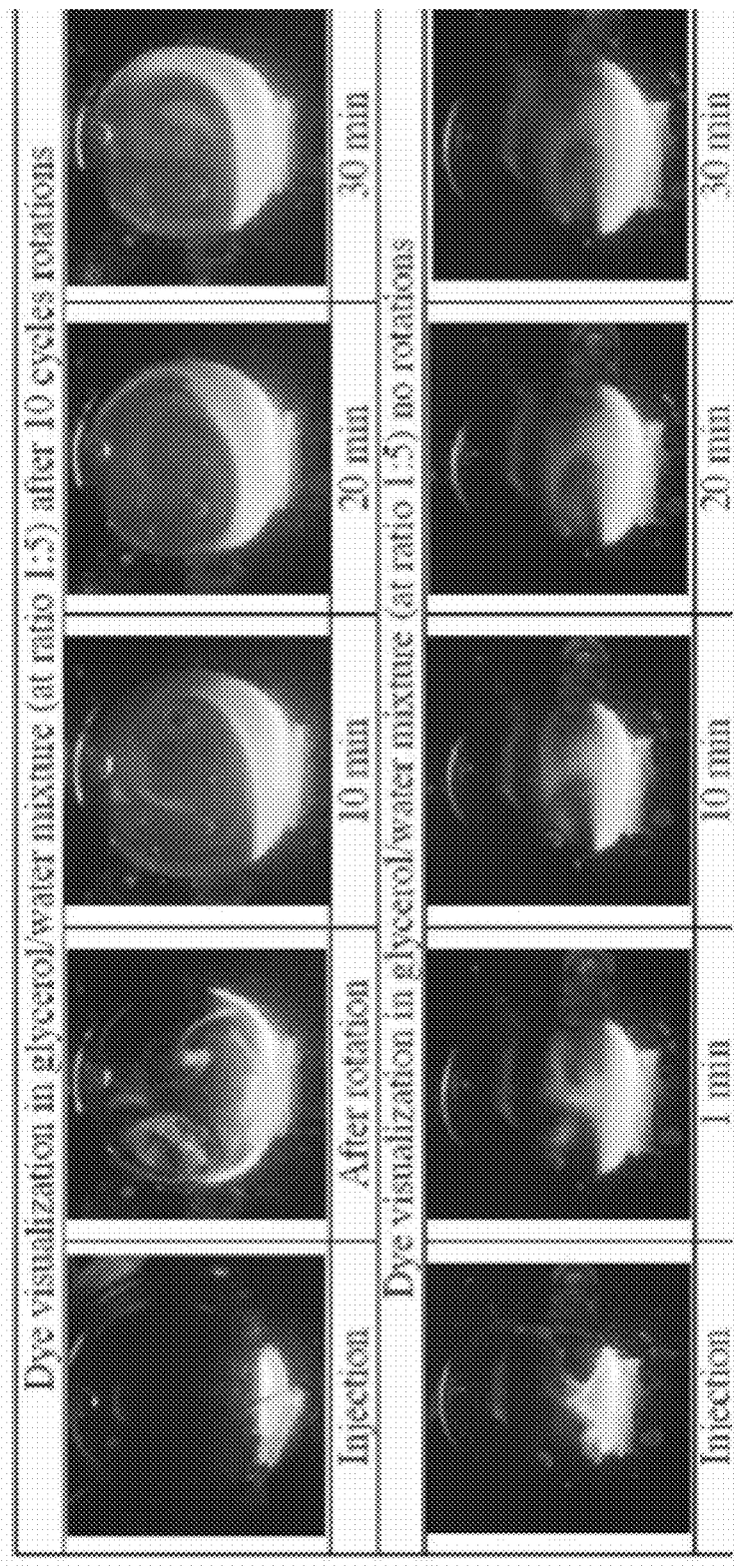
FIG. 19 illustrates dye visualization images generated in accordance with some embodiments of the presentation disclosure.

FIG. 19 illustrates a sequence of images taken after a 10-cycle and zero-cycle rotations in accordance with some embodiments of the present disclosure. In the 10-cycle image sequence, an image is taken immediately after the rotation has stopped. In the zero-cycle (no rotation) sequence, an image is taken 1 minute after the simulated drug (e.g., dye) was injected. Here, particle concentration is a good indicator for the mixing process, which can be reflected by the pixel intensity. In geohydrology, fluorescence is used in situations where there is insufficient lighting, but precise quantitative data is required. The intensity of visible spectrum fluorescence after excitation by a certain spectrum light is measured by a fluorimeter to identify the presence and the number of specific molecules in a medium. Taking the same idea, in our quantification process, the pixel intensity (grayscale value) was used to indicate the concentration of drug (glycerol/water/fluorescein mixture).

Figure 20:
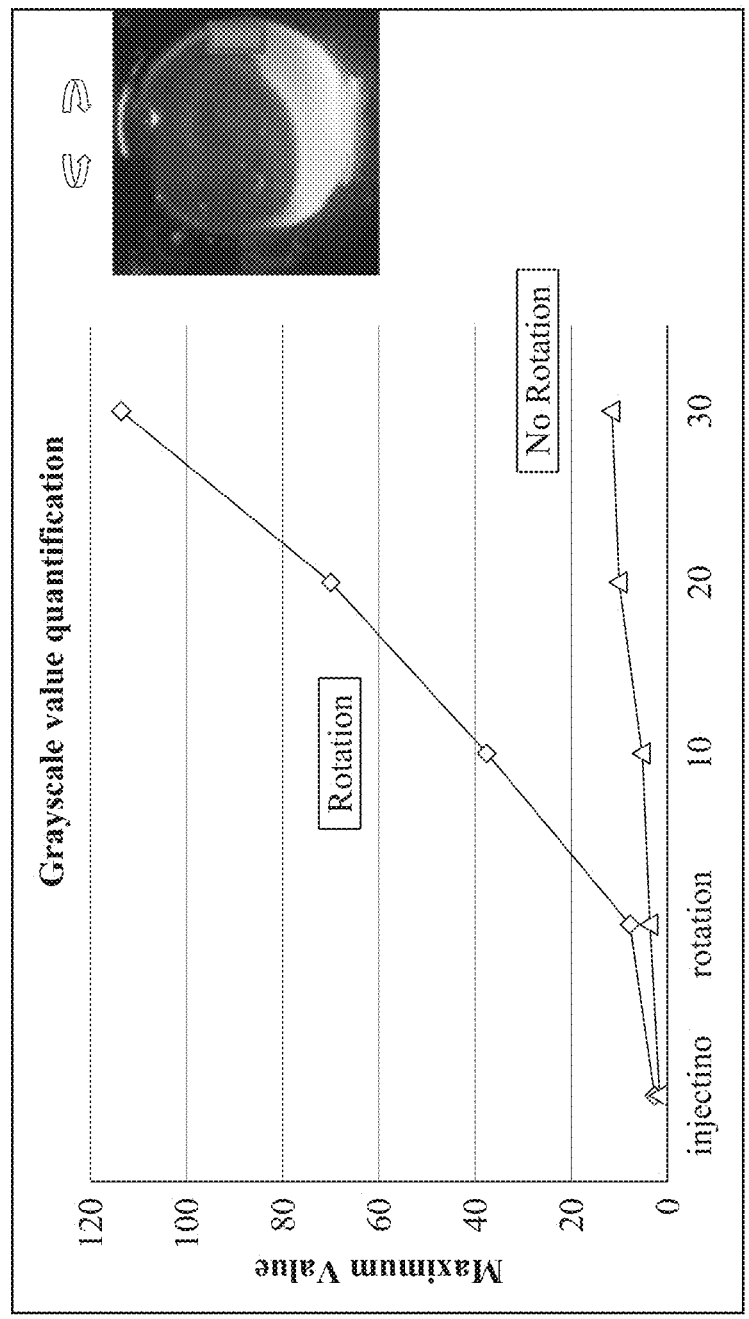
FIG. 20 is a graph illustrating the fluorescent particle concentration reaching the target tissue in accordance with some embodiments of the presentation disclosure.

Pixel intensity can be measured using the open source pixel intensity determination software such as, but not limited to, image J. The grayscale reading function can quantify the maximum grayscale value in a defined region. As demonstrated in FIG. 20, the area of interest was defined first so the program only calculated pixel intensity within the defined region. The location of this defined region corresponds to the location of macula in a human eye. As shown in the 10-cycle image sequence, lateral movements can promote drug mixing in the eye and facilitate drug delivery to macula.

Based on experimentations, it is determined that lateral rotations can facilitate a faster drug mixing in the eye. Additionally, lateral movements also help with the distribution of the drug even with vitreous humor of higher viscosity/density. However, in the glycerol/water mixture LIF visualization images, the four circulations weren't observed. Therefore, this inspired us to repeat the flow visualization (with fluorescent particles) that has been done with 0.9% saline, although with glycerol/water mixture at various ratios this time.

Figure 21:
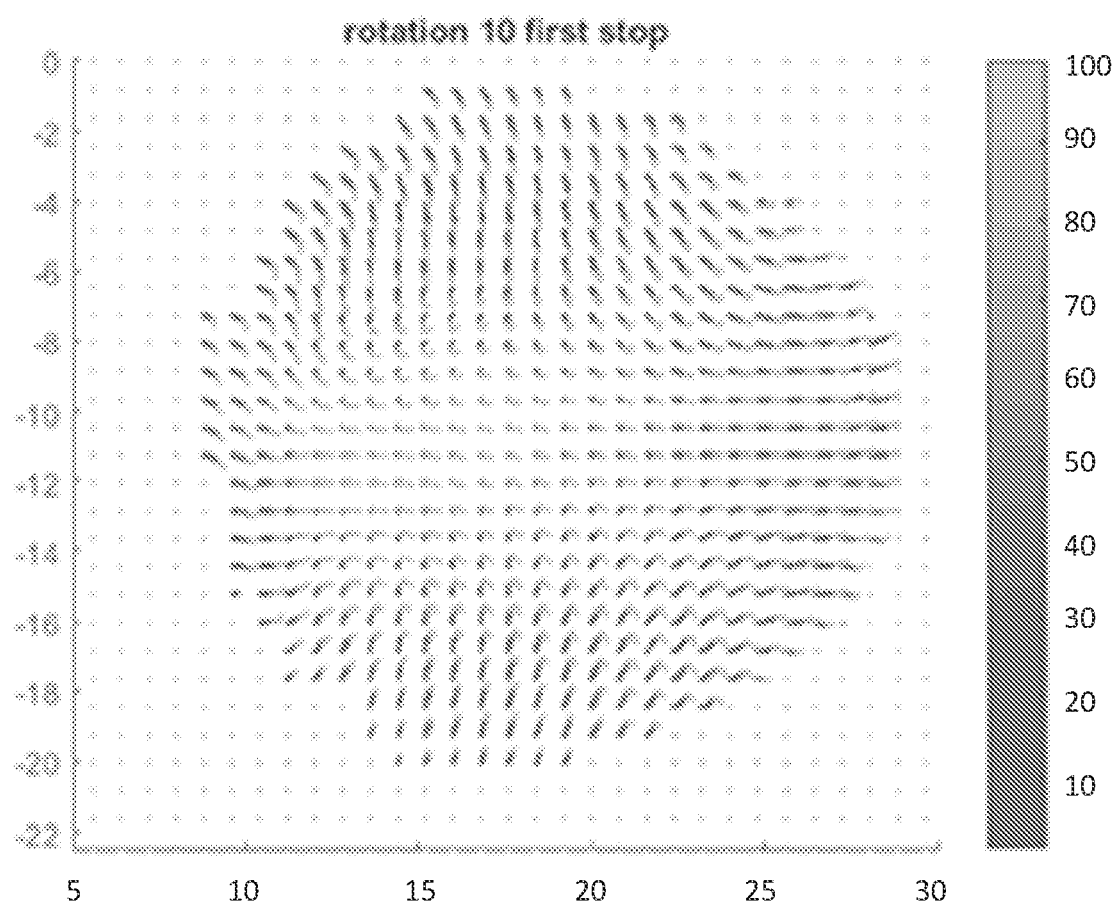
FIGS. 21-23 illustrate particle pathline visualization after various cycles of rotations for vitreous humor of higher density/viscosity in accordance with some embodiments of the presentation disclosure.
Figure 22:
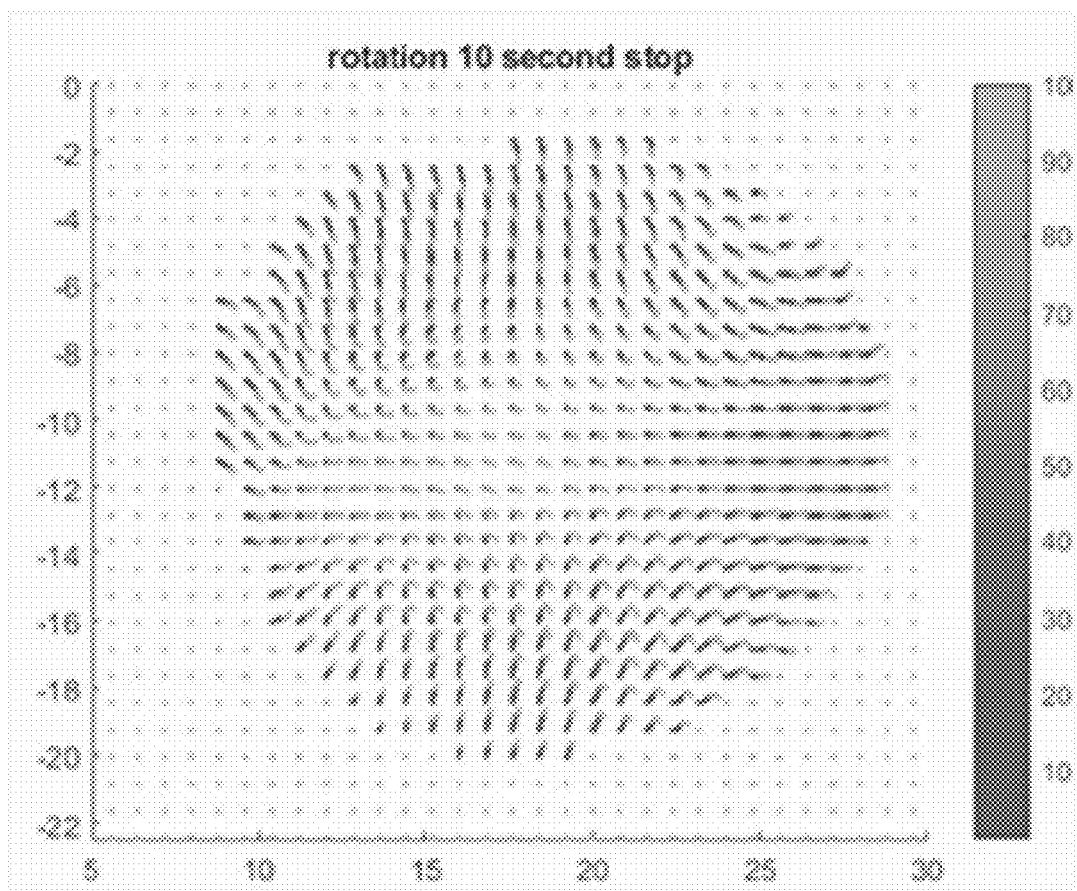
Figure 23:
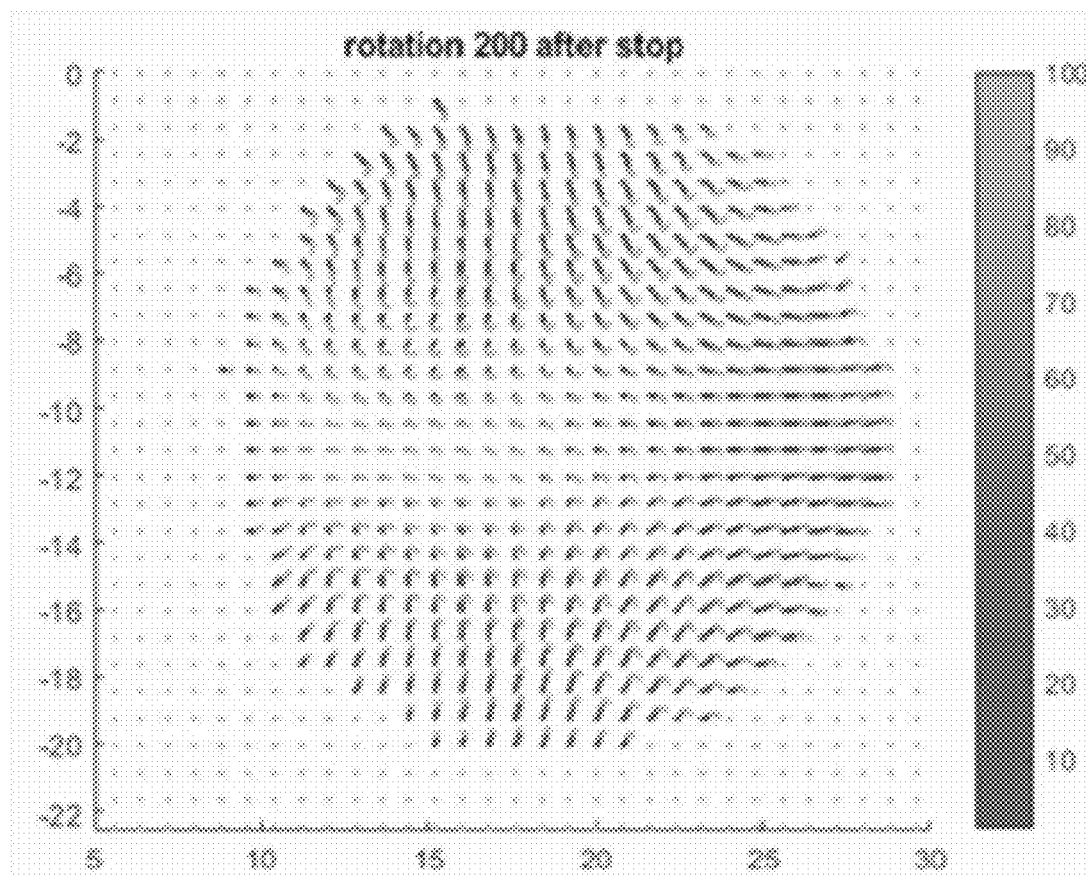

PIV visualization and PIV analysis were performed for the following three time intervals: after 10 cycles of lateral movements, after 20 cycles of lateral movements, and finally after 200 cycles of lateral movements. The resulting raw images were then analyzed following the same PIV analysis procedures and particle pathline were visualized. FIGS. 21, 22, and 23 illustrate the resulting particle pathline visualizations for after 10 cycles, 20 cycles, and 200 cycles respectively. For this experiment, glycerol/water mixture was used: glycerol 20.2 wt % to serve as the vitreous humor. The initial positions of particles were color coded in dark blue, then green, and finally light blue. The entire duration of particle tracking was 10 seconds, which was consistent with the analysis with 0.9% saline. During the actual experiments, no obvious circulation was observed visually. Not surprisingly, these particles did not move as much as indicated in the pathline visualization results in FIGS. 21-23. Additionally, it can be hard to tell a difference between the particle pathline fields after 10 cycles of movements and after 200 of cycles movements.

The dye visualization results summarized in section 4.4 show that center injection takes the shortest amount of time as well as the least amount of movement to mix the drug well in the eye. The bottom injection and side injection take a similar but longer amount of movement and duration to achieve complete drug mixing in the eye. This observation could be explained further by comparing it with the results from particle pathline visualization.

Figure 24:
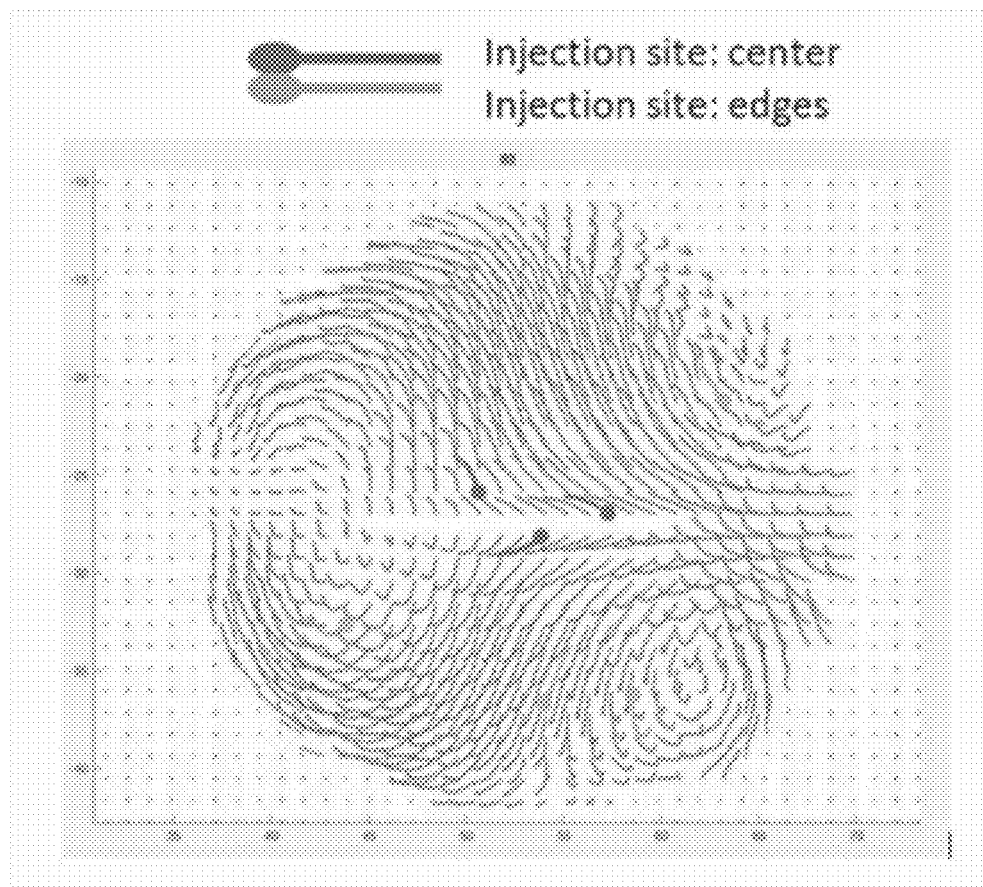
FIG. 24 illustrates particle pathline visualization after various cycles of rotations for vitreous humor of lower density/viscosity (0.9% saline) in accordance with some embodiments of the presentation disclosure.

As shown above, lateral movements can induce four circulations. To make direct comparison, particles in the three regions of interests are highlighted in FIG. 24, which illustrates dye (drug) movements based on injection location. As shown by the pathlines, particles in the side and bottom regions are "trapped" around their initial locations. Particles that are initially in the center region have more flexibility to move towards other regions. This result contradicts conventional injection technique used by ophthalmologists, which tend to inject drugs at a location that is very close to the front of the eye. Based on the pathlines of FIG. 24, injection at the front of the eye is not an optimal spot because it directly puts drug at a "side" location, which might not be so helpful in facilitating drug deliveries to the back of the eye.

Figure 25:
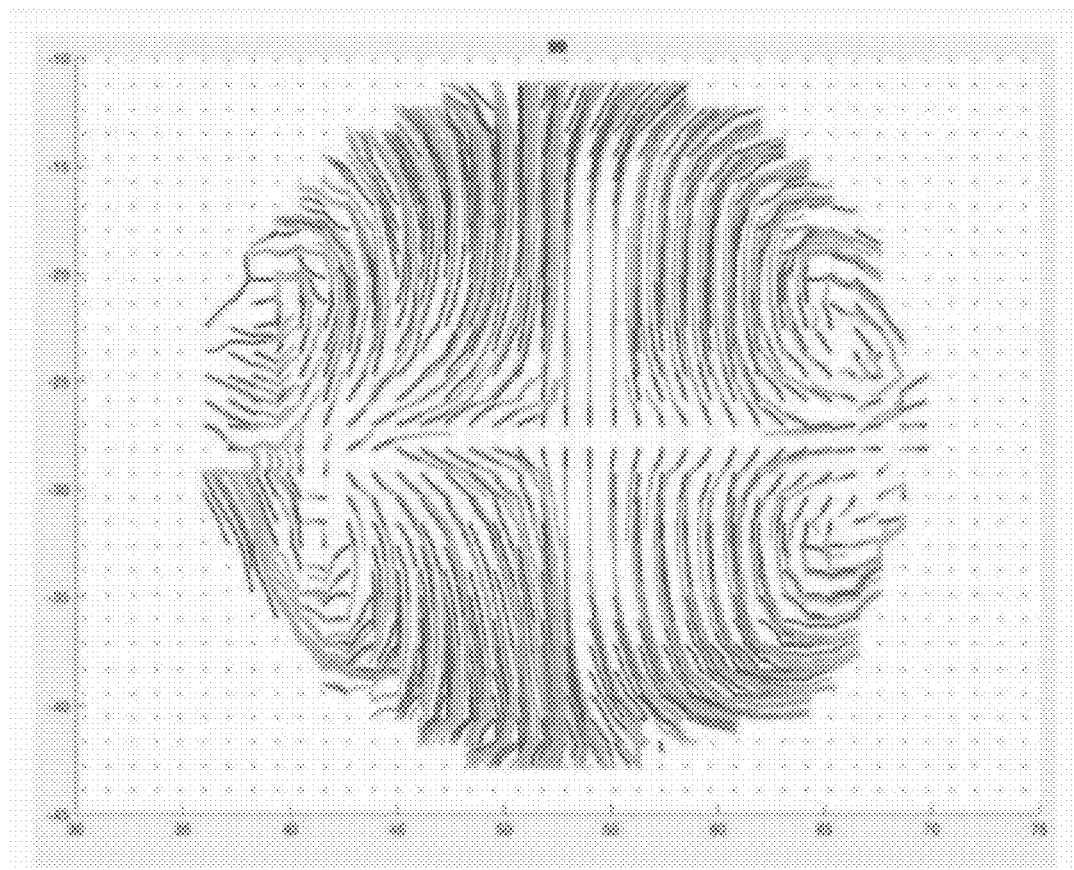
FIG. 25 illustrates simulated particle pathline visualization for vitreous humor of lower density/viscosity (0.9% saline) in accordance with some embodiments of the presentation disclosure.

Previous pathline visualizations have been made after the fluid rotation has stopped, which leads to circulation decay of the fluid. To learn more about the movements of drug injected in the vitreous humor, pathline visualizations for non-decaying circulation are simulated. In some embodiments, this can be done by taking the first fluid velocity field from the moment right after lateral movement is stopped and projecting it forward in time. In this way, it was assumed that the velocity field with the strongest circulation was sustained. FIG. 25 illustrates a simulated pathline visualization chart in which the circulation does not decay. As shown in FIG. 25, particles that start from the center regions have more freedom to move towards other regions, whereas particles in the side/bottom regions tend to stay in the same region. FIG. 25 also shows what happens after the lateral movements and the circulation sustains longer than what has been observed in the experiment. In other words, if the vorticity does not decay quickly, the particle movement is sustained for a longer duration.

Based on the above experimental results, four circulations were observed after introducing lateral movements to 0.9% saline. However, the same mixing pattern was not observed in the glycerol/water mixture. This discrepancy is possibly an effect of Reynolds number. Reynolds number describes the convection process over diffusion process in the flow motion. If Reynolds number is large, the convection process dominates over the diffusion process. Reynolds number can be calculated as $$Re = \frac{\rho U D}{\mu} \qquad (4)$$

where $\rho$ is the density of fluid, U is the velocity of flow, D is the characteristic length, and $\mu$ is the dynamic viscosity.

In some embodiments, Reynolds number is around 400 for the 0.9% saline solution. For the glycerol/water mixture, Reynolds number is around 200 or smaller. There is likely a transition point in the range 200<Re<400, which determines whether the circulations can be turned on. Since $\rho$, $\mu$, and D varies among different individuals and these parameters also changes over time to the same person with aging process. It is not certain that lateral movements of the eye can facilitate drug mixing for everyone, although with higher rotation speed (U), Reynolds number is higher and a possibly better mixing effect may be achievable.

Although applying lateral movements can introduce convective flow into the vitreous chamber and facilitate improved drug mixing, it might not be an optimal solution for two reasons. First, the overall circulation effects induced by lateral movements are not sufficiently long in duration to ensure a continuous mixing. Secondly, whether the circulations can be turned on depends largely on each individual's eye properties. Since our goal is to achieve good drug mixings with minimal efforts received from the patients, a thermal-driven method for inducing drug movements can be employed.

Thermal Effects on Fluid Mixing in the Eye

This part of the disclosure explores thermal effects on promoting drug mixing in the eye. Specifically, the following three factors are investigated to understand their effects on thermally inducing drug mixing in the eye: 1) varying temperature difference, 2) varying heating position, and 3)

varying density difference between the drug and vitreous humor. As previously mentioned, there has not been much study on drug mixing in the eye in the past. Limitations are primarily due to lack of full understanding of the anatomy and physical properties of living animal vitreous structure and having many unknown parameters—making numerical simulation difficult.

In some embodiments, the same eye model from the eye movements study is used for the thermal effects experiments. To determine what temperature differences to study, it is necessary to understand the heat tolerance. Eyes are sensitive and thus cannot endure high temperatures for a long time. Given that the temperature limit for a human being to feel pain is 10 Celsius above body temperature. Accordingly, the temperature difference to be experimented is ±10° C. of 37° C., which is the body temperature. In some embodiments, a 5 Celsius and 10 Celsius temperature difference are selected to apply between the eye model and the heat source. The temperature difference can range from 2.5-12.5 degrees Celsius.

Additionally, placement of heating elements on the eye is another important variable. Different fluid motions are stimulated by placing the heat element at different positions around the eye. Precise placements of heating elements and temperature control can achieve optimal fluid mixing results without having to introduce too much temperature change to the eye.

Figure 26:
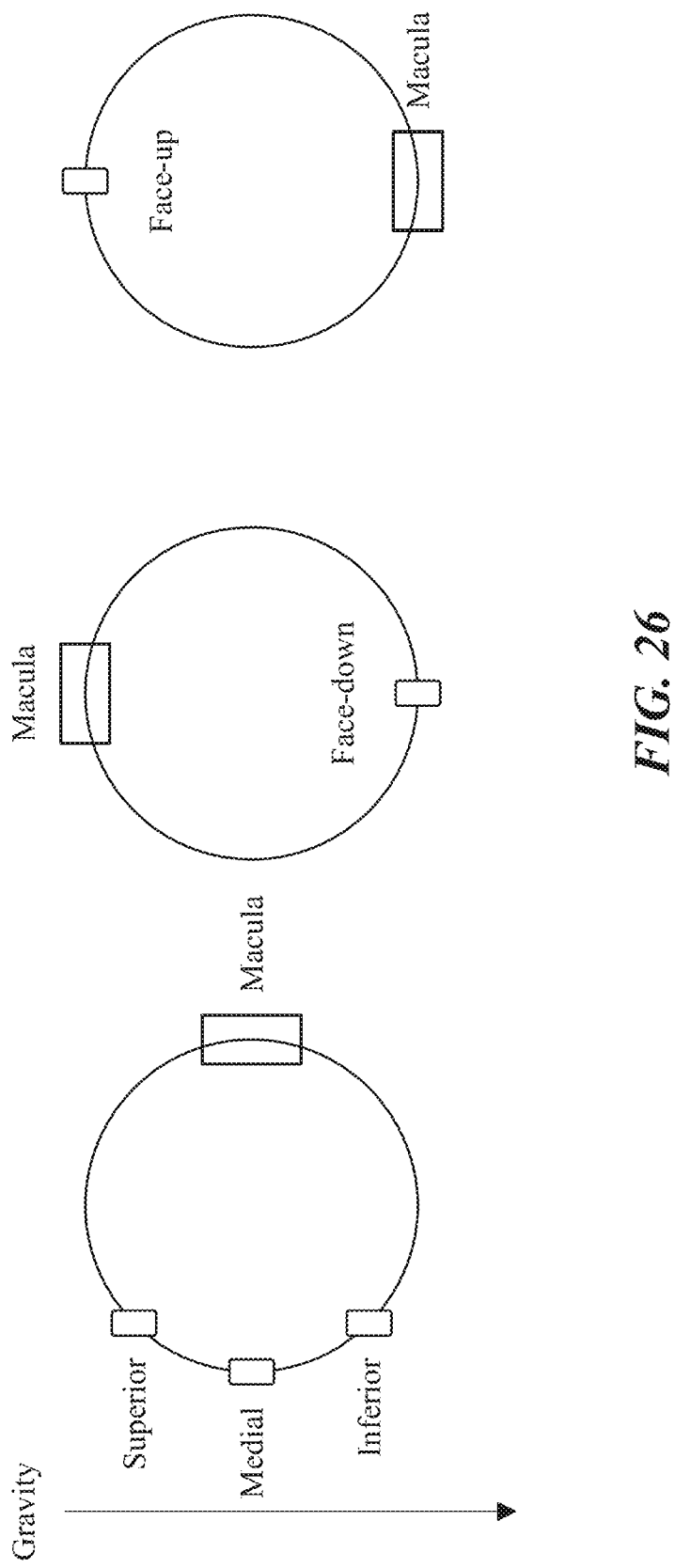
FIG. 26 illustrates heating positions around the eye for upright and heads-up/heads-down positions in accordance with some embodiments of the presentation disclosure.

FIGS. 26A-C illustrate various heating locations and head position in accordance with some embodiments of the present disclosure. In FIG. 26A, the head is in the upright position. In this position, the heating elements can be placed in three different locations, although more locations are possible and contemplated. As shown, a first position is the medial or center position. A second position is the superior or upper position, and the third position is the inferior or lower position. In FIG. 26B, the head is in a face-down position where the patient is lying with the face down. In the face-down position, the heating elements can be located in the medial portion of the eye. Other locations such as superior, inferior, left, and right are also possible. In FIG. 26C, the head position in the face-up position where the person is lying with the face in the face-up position. Here, the heating element can be also located in the medial or center position.

In the fluid movement study, drug (fluorescein/solution of interests mixture) is added to a solution having approximately the same density/viscosity of a human vitreous humor. In the thermal effect experiment, the effects of introducing density/viscosity difference between the injected drug and the vitreous are studied. This can help understand how drugs behave in various density/viscosity environments and/or method of deliveries.

Vitreous Humor Preparation

To prepare for liquid that goes into the container, glycerol and water at various water-to-glycerol ratios (glycerol 20.2 wt %, glycerol 33.6 wt %, and glycerol 11.2% respectively) were prepared. Each set of mixtures was placed in the room temperature for more than 48 hours to ensure a consistent initial temperature. It is worth noting that glycerol 20.2 wt % mixture has physical properties (density and viscosity) that are most similar to vitreous humor in the eye. Table 8 shows the properties of various water/glycerol mixtures used in the thermal effect study.

TABLE 8

Material properties of vitreous and materials used in the current study

| Material | Viscosity (mPa s) | Density (kg m$^{-3}$) | Thermal expansion coefficient (at 20° C.) | Refractive index | Coefficient of thermal conductivity (W mK$^{-1}$) |
| --- | --- | --- | --- | --- | --- |
| Human vitreous | 1-3.6 | 1005.3-1008.9 | — | 1.337 | 0.594 |
| Glycerol 20.2 wt % | 1.7 | 1046.8 | 0.000315 | 1.357 | 0.556 |
| Glycerol 33.6 wt % | 2.7 | 1081.5 | 0.000385 | 1.375 | 0.515 |
| Glycerol 11.2 wt % | 1.3 | 1024.5 | 0.000255 | 1.346 | 0.591 |

Table 8—Comparison of Material Properties

Figure 27:
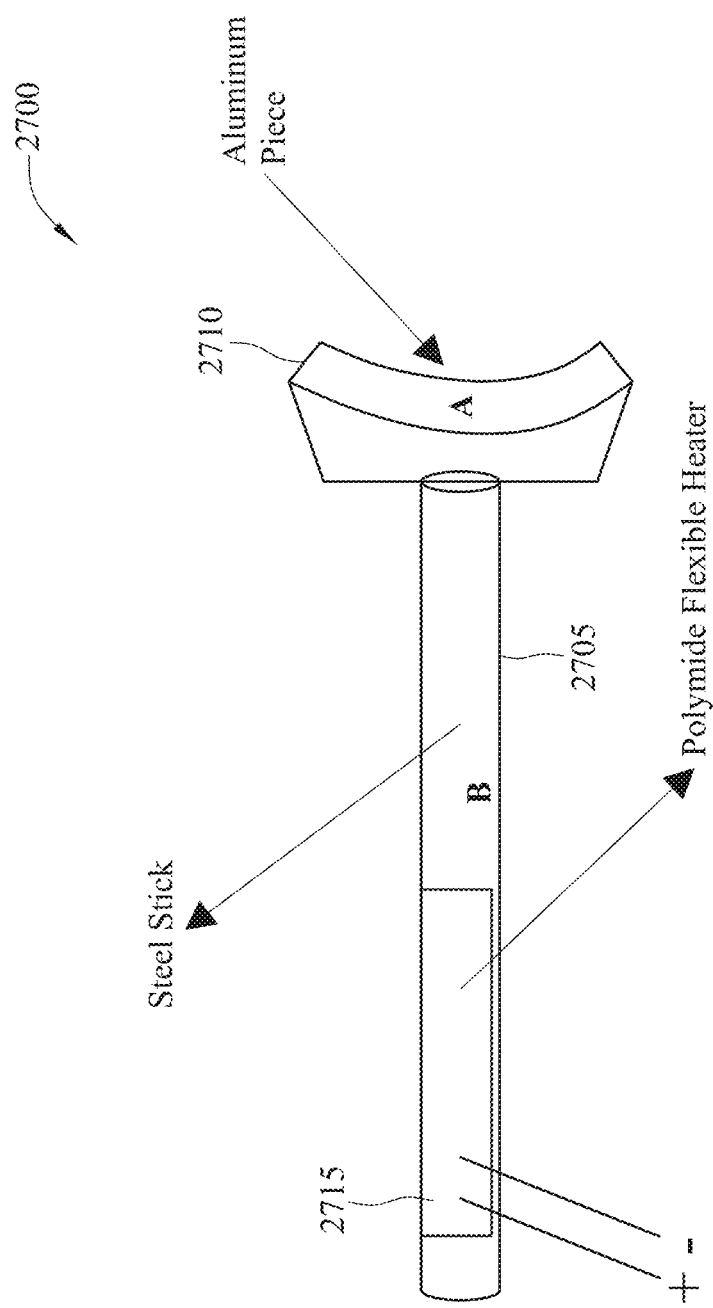
FIG. 27 illustrates a heat transfer device in accordance with some embodiments of the presentation disclosure.

FIG. 27 illustrates a heater 2700 in accordance with some embodiments of the present disclosure. When applied to the eye, heater 2700 can induce a temperature gradient in the vitreous humor. Heater 2700 includes a steel rod 2705, a flexible pad 2710 and a voltage regulator 2715, Flexible pad 2710 can be a polyimide film, which can include metal components such as aluminum, stainless steel, or other biocompatible metals. Flexible pad 2710 can have an effective contact area of approximately 5 mm by 5 mm. Other shapes and dimensions are possible and are contemplated. For example, flexible pad 2710 can have a circular or polygonal shape.

A calibration experiment was designed to obtain a voltage-temperature relationship. This facilitated an indirect but accurate temperature control via voltage reading. During the calibration process, voltage input was increased incrementally by 2 Volts at a time. Although different voltage increments can be used such as a range between 0.5-5 volts. Temperature readings were obtained using a digital thermometer. After each voltage adjustment was made, a temperature reading was recorded after it became stabilized for at least 10 mins. Temperatures at two locations were measured, denoted as A and B in FIG. 27. The calibration process was repeated a few times to ensure its accuracy. This voltage-temperature curved was referenced for temperature control throughout this study.

Figure 28:
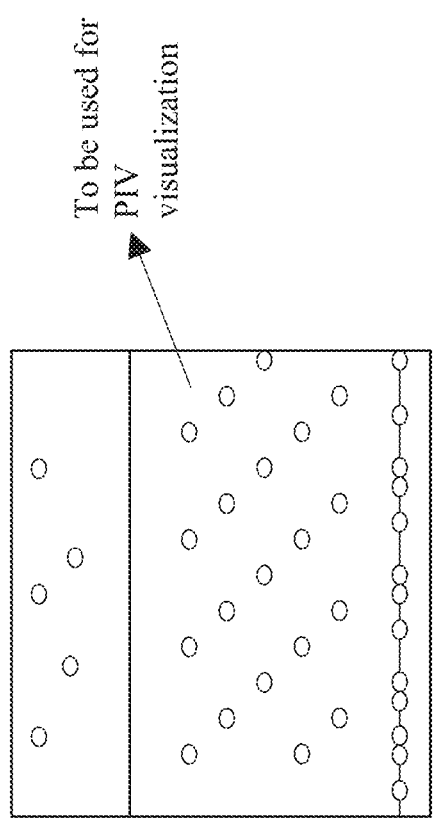
FIG. 28 illustrates a process for stratifying silver-coated particles in a glycerol/water mixture in accordance with some embodiments of the presentation disclosure.

Silver coated fluorescence particles can be used in the artificial vitreous humor solution. To prepare for solutions for PIV visualization, a spoonful of silver coated fluorescence particles was mixed with a solution of glycerol/water mixture. In some embodiments, after these particles were settled and stratified in the solution, only the middle layer was captured for use in PIV visualization. FIG. 28 illustrates the separation process 2800 used to extract optimum fluorescence particles for use in the PIV procedure in accordance with some embodiments of the present disclosure. In the PIV visualization process, the flow profile was observed and captured at 10 frames per second (fps) for a duration of 10 minutes after the heat source was applied.

For laser induced fluorescence visualization (FIL), fluorescein was first dissolved in water and then mixed with solution of interests at 1:50 ratio (fluorescein to solution of interests=1:50). Since the density and viscosity of glycerol 20.2 wt % mixture is the most similar to those of human's vitreous humor, glycerol 20.2 wt % mixture can be used to replicate the vitreous humor. In some embodiments, glycerol 11.2 wt % mixture and glycerol 33.6 wt % mixture were mixed with fluorescein at 1:50 (fluorescein: solution) ratio.

Adding a glycerol 33.6 wt %/fluorescein mixture to the eye model simulates the process of adding a drug that is heavier and more viscous than the vitreous humor to the eye. Adding a glycerol 11.2 wt %/fluorescein mixture to the eye model simulates the process of adding a lighter and less viscous drug to the eye.

Figure 29B:
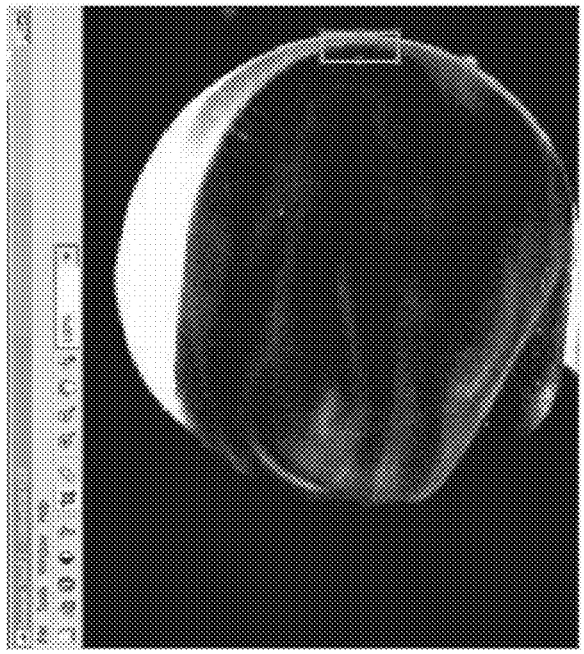
FIGS. 29A and 29B illustrate a pixel intensity quantification process in accordance with some embodiments of the presentation disclosure.
Figure 29A:
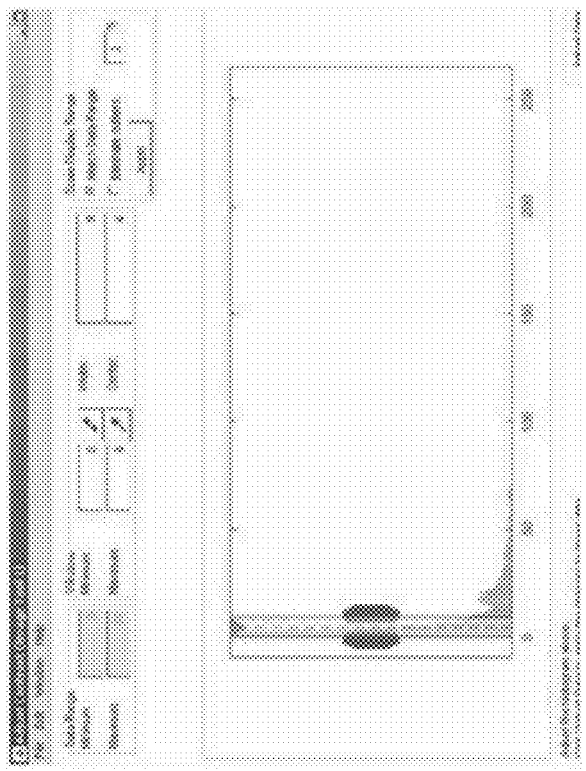

Pixel intensity is correlated with drug (glycerol/water/fluorescein mixture) concentration. Therefore, to quantify the amount of drug (glycerol/water/fluorescein mixture) that have entered target treatment region, image tool in MATLAB was used to quantify pixel intensity (see FIG. 29A). FIG. 29B illustrates the area of interest having a size of 5×20 pixels located near the center of the eye model on the right side. The location of this region corresponds to the actual position of the macula, which is the desired AMD treatment spot in the eye. The size and location of this region were kept the same throughout all image quantifications. When fluorescein is excited by the laser, it becomes bright/white (see FIG. 29B).

A computation study was conducted with the aid of FEATool Multiphysics/MATLAB. The fluid has thermal diffusivity $\alpha$ and viscosity $\nu$. Rayleigh number for this flow is defined as:

$$R_a = g\beta\Delta T x^3 / \alpha\nu$$

Based on this formula, a Rayleigh of 8300 is obtained for a glycerol 20.2 wt % mixture at $\Delta T=10$ Celsius, and Prandtl number is defined as $Pr=C_p\mu/k=13.48$ for glycerol 20.2 wt % mixture, and $\Delta T$ is the temperature difference between the heat source and the eye model. All lengths are non-dimensionalized with respect to D, the diameter of eye model; all velocities with respect to $\alpha/D$; time with respect to $D^2/\alpha$; vorticity with respect to $\alpha/D^2$, temperature with respect to $\Delta T$. The study object was modeled as a two-dimensional viscous Boussinesq fluid in a circular domain, and the equations for numerical modeling are listed below:

$$\frac{\partial U}{\partial X} + \frac{\partial V}{\partial Y} = 0 \quad (5)$$

$$\frac{\partial U}{\partial \tau} + U\frac{\partial U}{\partial X} + V\frac{\partial U}{\partial Y} = -\frac{\partial P}{\partial X} + Pr\left(\frac{\partial^2 U}{\partial X^2} + \frac{\partial^2 U}{\partial Y^2}\right) \quad (6)$$

$$\frac{\partial V}{\partial \tau} + U\frac{\partial V}{\partial X} + V\frac{\partial V}{\partial Y} = -\frac{\partial P}{\partial Y} + Pr\left(\frac{\partial^2 V}{\partial X^2} + \frac{\partial^2 V}{\partial Y^2}\right) + Ra \cdot Pr * T \quad (7)$$

$$\frac{\partial T}{\partial \tau} + U\frac{\partial T}{\partial X} + V\frac{\partial T}{\partial Y} = \frac{\partial^2 T}{\partial X^2} + \frac{\partial^2 T}{\partial Y^2} \quad (8)$$

Figure 30:
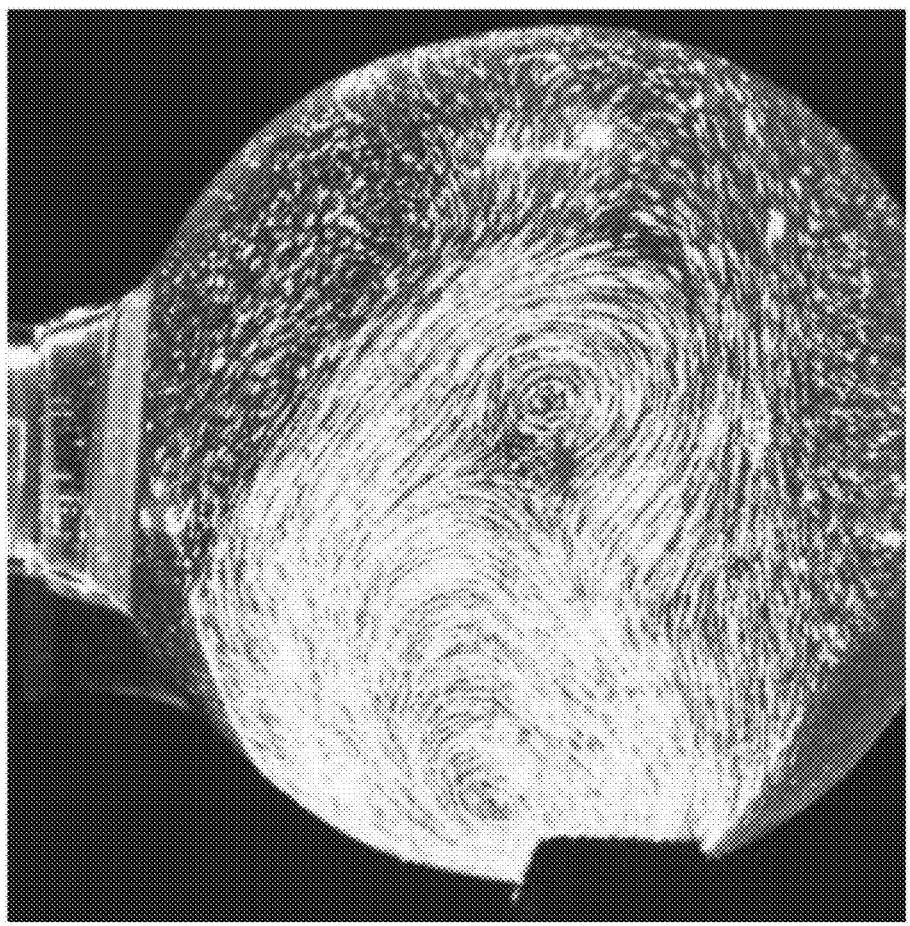
FIG. 30 illustrates a pathline visualization of a process that uses a 5-Celsius temperature difference and medial heating in accordance with some embodiments of the presentation disclosure.

FIG. 30 illustrates pathline visualization images of process 3000 that uses an eye model being subjected to center heating at 5 Celsius temperature difference. In the $\Delta T=5°$ C. case, most of the flow is happening on the left side of the eye model. In process 3000, heat is being applied at the center of the eye (center heating) using heater 2700.

Figure 31:
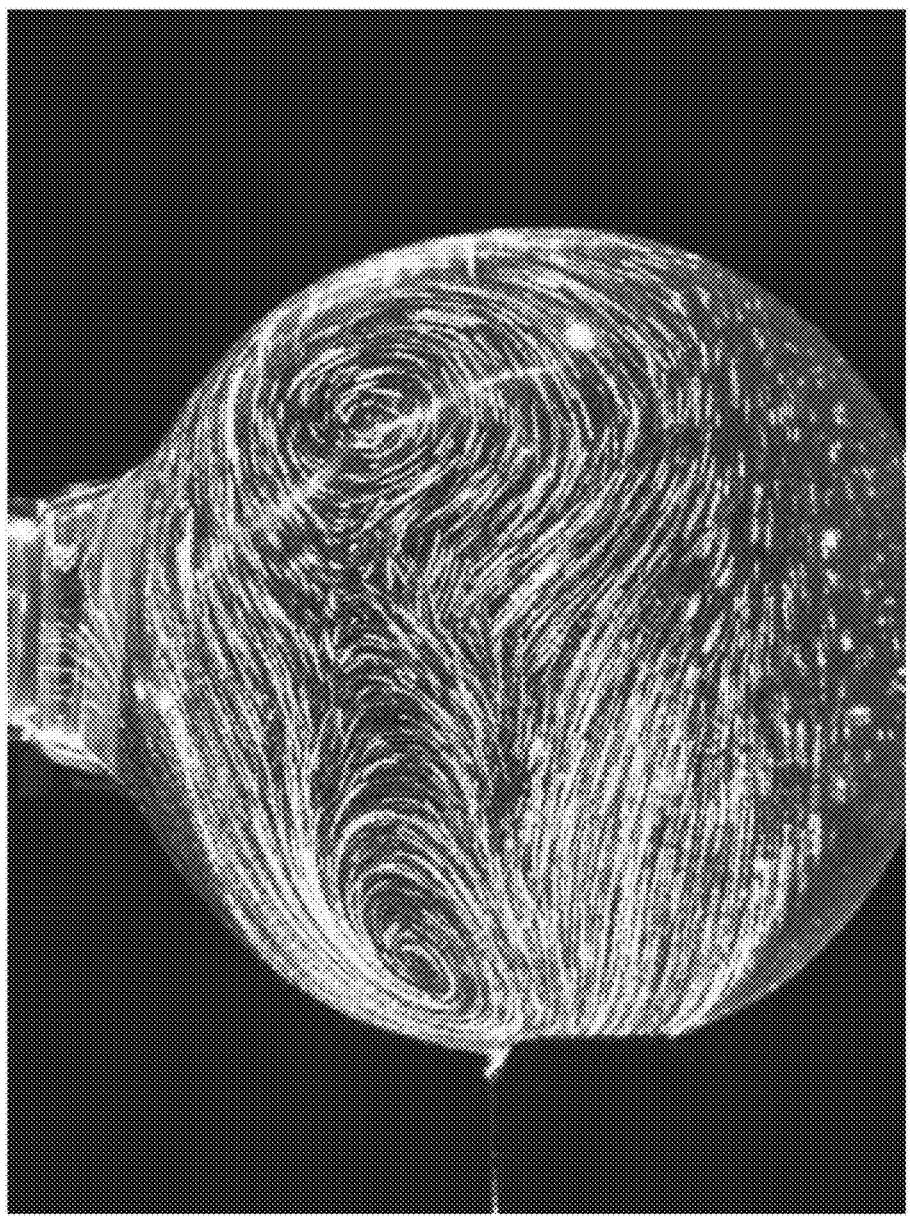
FIG. 31 illustrates a pathline visualization of a process that uses a 10-Celsius temperature difference and medial heating in accordance with some embodiments of the presentation disclosure.

FIG. 31 illustrates a pathline visualization of process 3100 that uses an eye model being subjected to center heating at $\Delta T=10°$ C. in accordance with some embodiments of the present disclosure. As shown in FIG. 31, the flow here is stronger than the flow in FIG. 30 as mixing is happening in regions near macula. However, there appears to be little mixing at the bottom of the eye model. Process 3100 also uses center heating.

Figure 32:
FIG. 32 illustrates a pathline visualization of a process that uses a 10-Celsius temperature difference and inferior heating in accordance with some embodiments of the presentation disclosure.

FIG. 32 illustrates a pathline visualization of process 3200 that uses an eye model being subjected to lower heating at a $\Delta T=10°$ C. Process 3200 uses lower heating, which means the location of heater 2700 is at lower position (see FIG. 26). As shown, process 3200 yields good circulation between all regions in the eye model.

Figure 33:
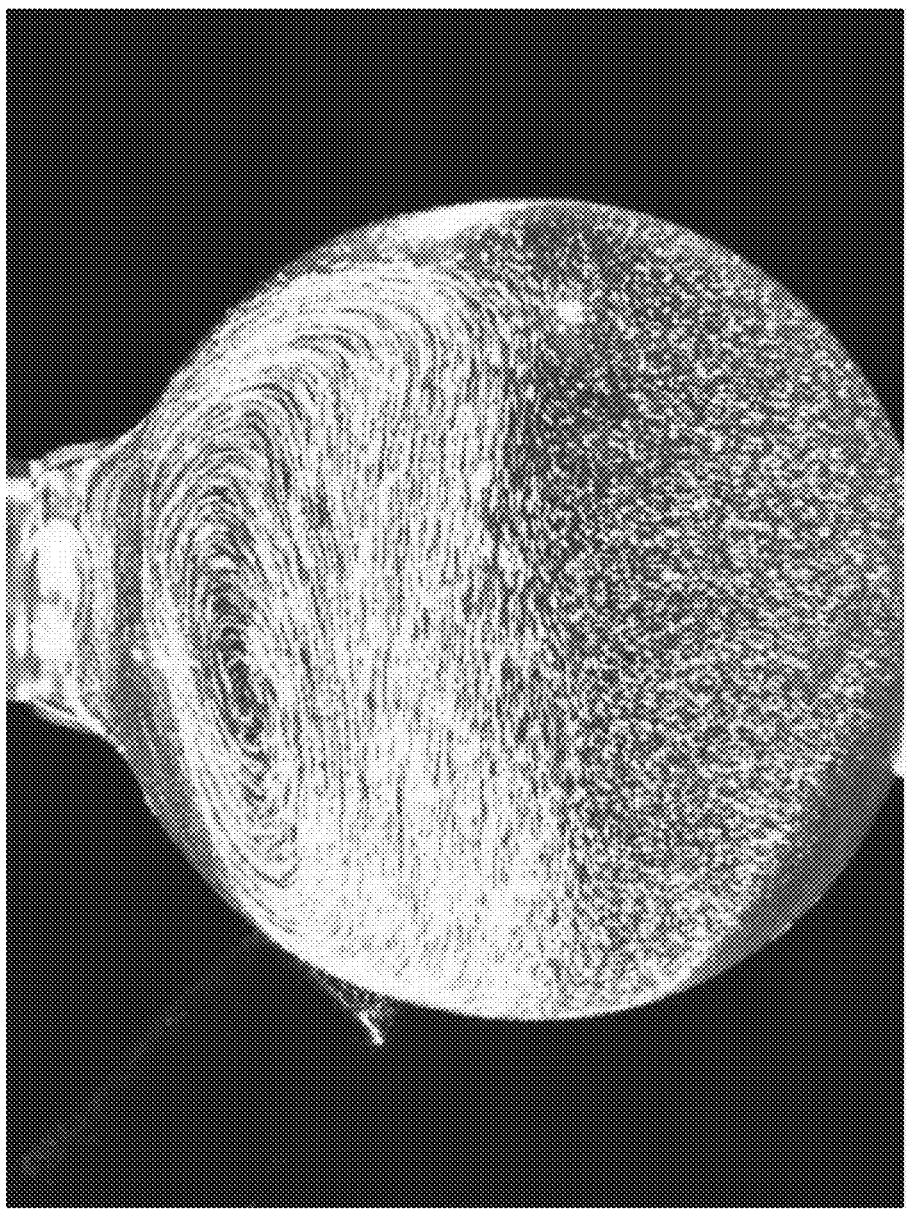
FIG. 33 illustrates a pathline visualization of a process that uses a 10-Celsius temperature difference and superior heating in accordance with some embodiments of the presentation disclosure.

FIG. 33 illustrates a pathline visualization of process 3300 that uses an eye model being subjected to upper heating at $\Delta T=10°$ C. in accordance with some embodiments of the present disclosure. Here, there is good mixture at the very top but not at the rest of the eye model.

Figure 34:
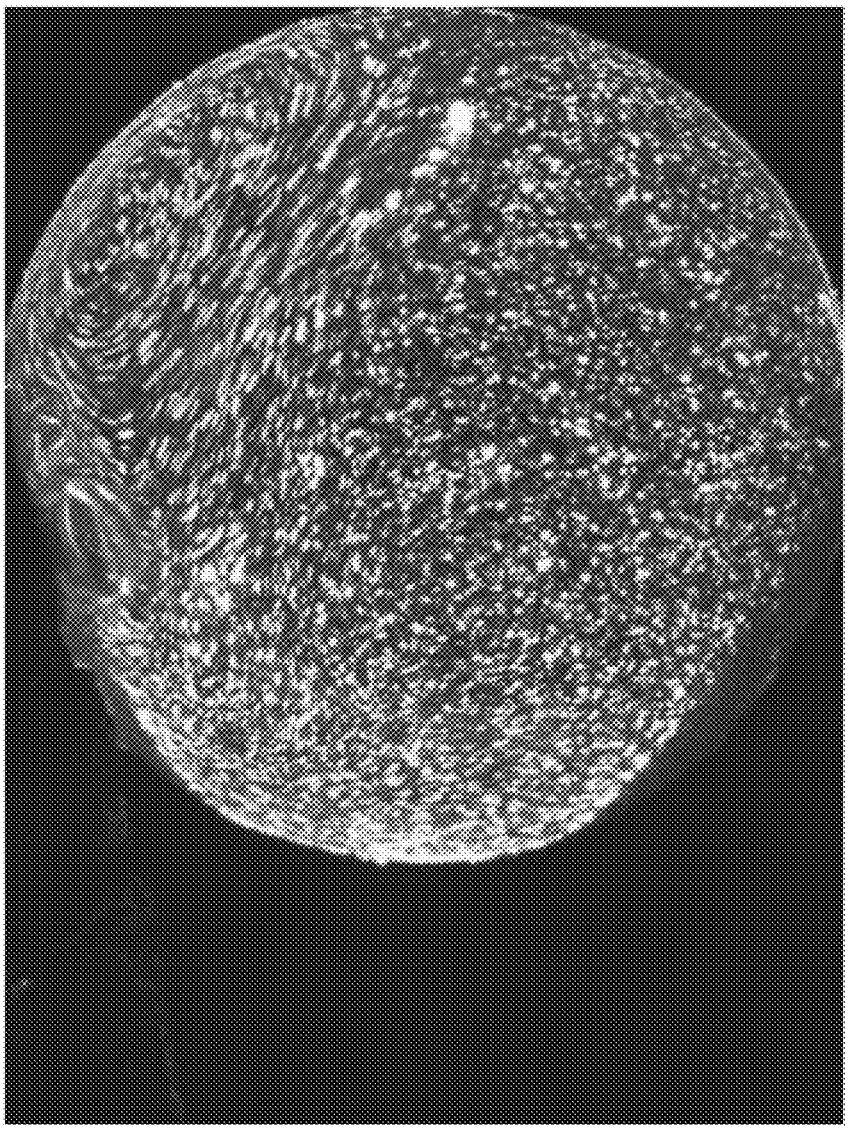
FIG. 34 illustrates a pathline visualization of a process that uses a 10-Celsius temperature difference and face-up heating in accordance with some embodiments of the presentation disclosure.

FIG. 34 illustrates a pathline visualization of process 3400 that uses an eye model being subjected to heads up heating at $\Delta T=10°$ C. in accordance with some embodiments of the present disclosure. Here, the overall flow behavior is weak.

Figure 35:
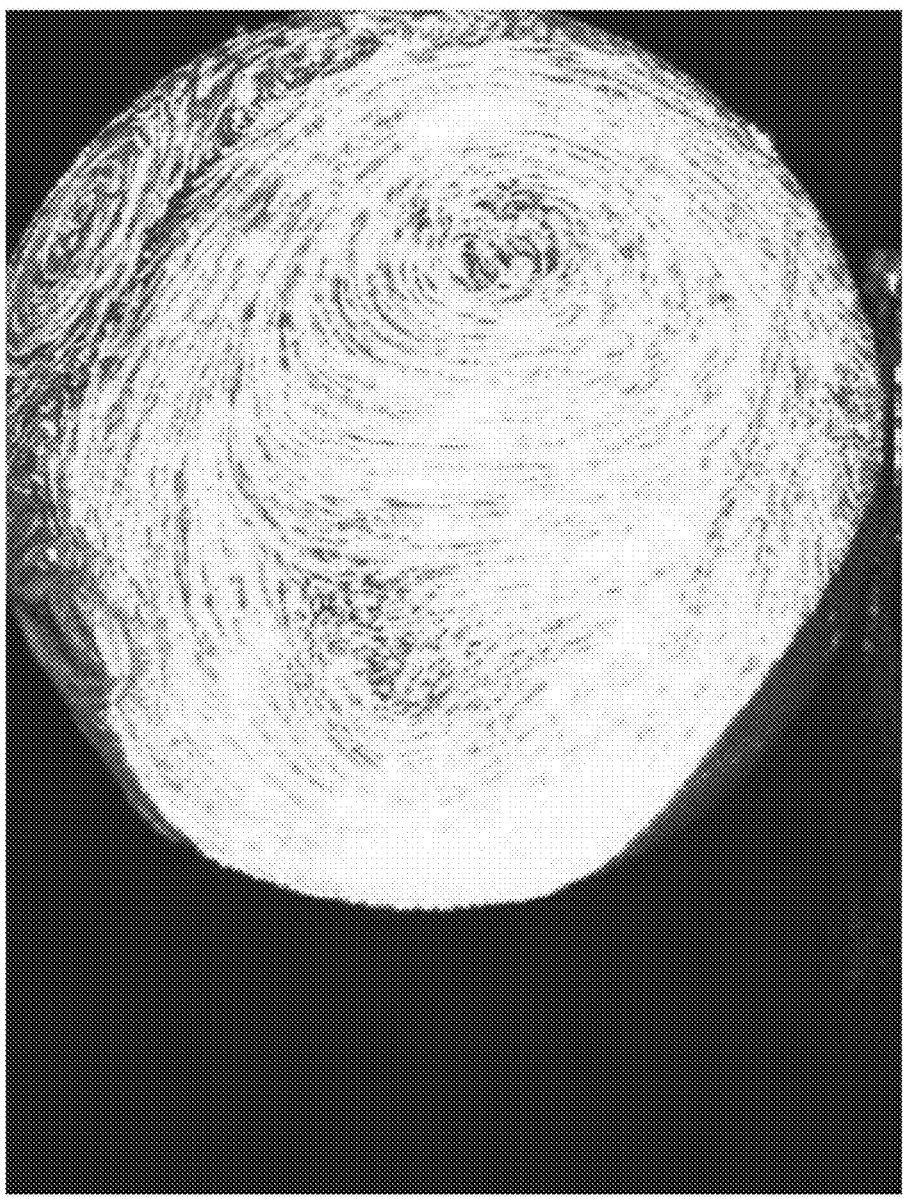
FIG. 35 illustrates a pathline visualization of a process that uses a 10-Celsius temperature difference and face-down heating in accordance with some embodiments of the presentation disclosure.

FIG. 35 illustrates a pathline visualization of process 3500 that uses an eye model being subjected to heads down heating at $\Delta T=10°$ C. in accordance with some embodiments of the present disclosure. As shown, process 3500 yields a very strong flow and mixture appears to be in all regions of the eye.

In some embodiments, the heating location can be selected based at least on the density difference between the drug and the vitreous body. For example, drug that has less density tends to stay at the top and, therefore, heating from an upper or center location is sufficient for inducing adequate drug mixing. However, lower heating is can be more helpful when the drug is heavier because heavier drugs tends to stay at the bottom.

Figure 36:
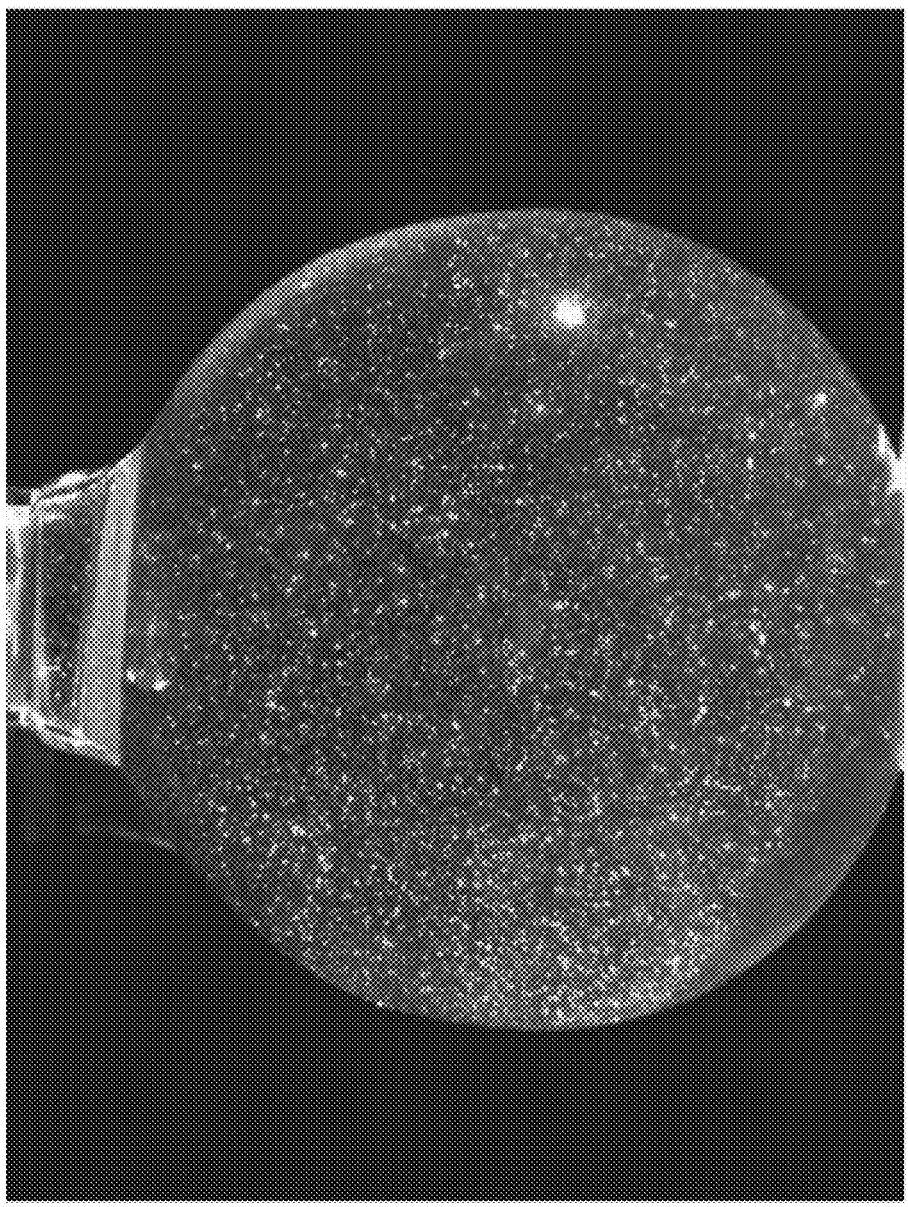
FIG. 36 illustrates a pathline visualization without heat.

Although center (medial) heating is quite effective in driving fluid mixing in majority regions of the chamber, it is not driving the flow in the bottom region as compared to lower heating. Upper heating does not seem to be effective at promoting fluid exchange between upper and lower part of the eye model. In each of processes 3000 through 3600, a total of 6,000 images were taken. And each image shown for each process can be a compilation of 100 images taken between 5 minutes and 5 minutes and 10 seconds. After performing a z-projection, there were 60 slices of 100 images in each slice for every case. Only one slice from each case was selected to be included in this section, and these slices are all captured during 5 mins to 5 mins and 10 second in each experiment. In addition, a slice of 100 images taken before the heating source was applied was also included as a control case (see FIG. 36, which illustrates a visualization pathline without a heat source).

Based on the experiments of process 3000 through 3600, it can be concluded that a greater temperature difference can induce stronger circulations in the eye model. For a person who's standing/sitting in the upright position, heating from the lower position can induce mixing in the entire eye model, whereas center and upper heating can only induce partial mixing in the eye model. For a person who's laying down on the chair with his/her head facing up, placing a heat source on top of his/her eyes doesn't seem to help with mixing, whereas having his/her head facing down instead can possibly induce very aggressive mixings in his/her eyes.

In summary, lower heating for someone in the upright position as well as heating from a heads-down position can be very helpful in achieving our goal to facilitate efficient drug mixing in the eye after an intravitreal injection.

Simulated Pathline Visualization

Figure 37A:
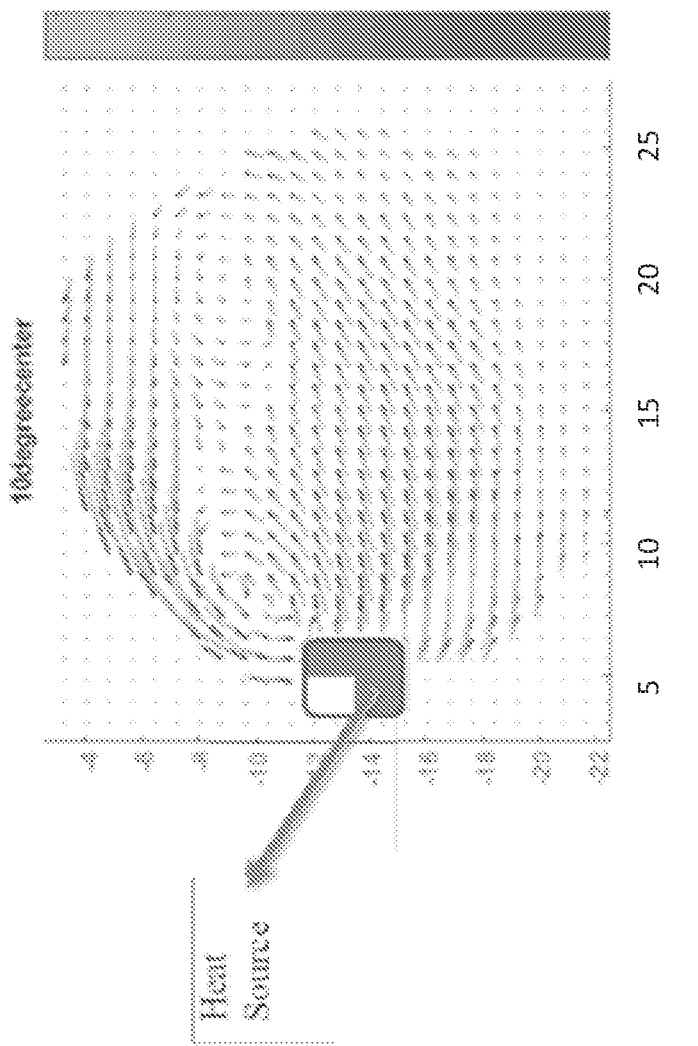
FIG. 37A illustrates an example simulated pathline visualization plot.

Regions of high vorticity magnitude typically correspond to regions of stronger shear or fluid circulation. The sign of the vorticity provides the direction of fluid circulation. The average magnitude of vorticity in each case over the course of 5 seconds (from 5 mins to 5 mins and 5 seconds) is summarized in the vorticity plot below. In comparison, particle pathline tracking for the same duration was generated using a pathline visualization (PV) software such as, but not limited to, MATLAB. FIG. 37 illustrates a simulated pathline visualization chart generated by the PV software.

Figure 37B:
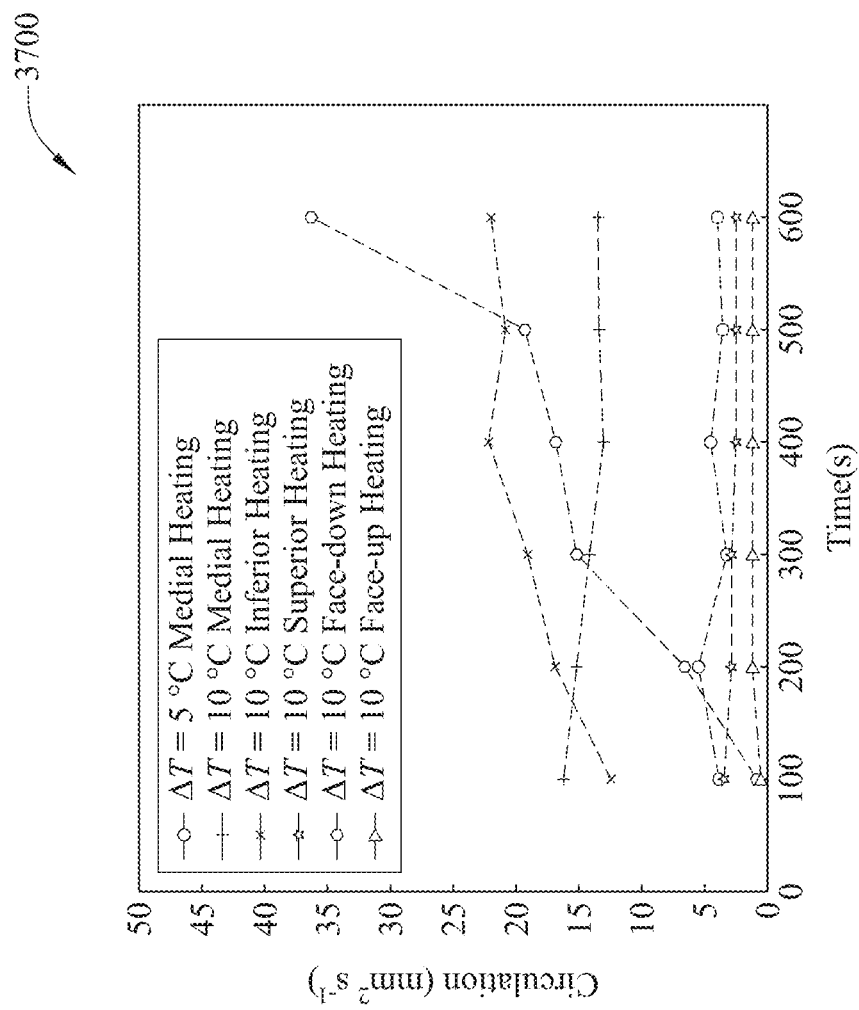
FIG. 37B illustrates the velocity and vorticity fields at different times in accordance with some embodiments of the presentation disclosure.

FIG. 37B is a chart 3700 illustrating the velocity and vorticity fields at different times throughout the heating process in accordance with some embodiments of the present disclosure. Chart 3700 shows the absolute values of the average circulation intensities, calculated from the vorticity across the entire plane of observation, at six different time points throughout the heating process. Based on observations from the LIF visualization study, if the injected drug is heavier and more viscous than the vitreous humor, drug delivery efficiency can be reduced. However, this could be solved by changing the heating location. Because properties of the vitreous vary a lot among individuals, and also change during the aging process, modifying the temperature difference, heating position, or even some of the physical properties of the anti-VEGF drug accordingly can boost the treatment performance for different individuals. In some embodiments, heating at a greater temperature gradient from an inferior position (while seating upright) or from the medial position while face-down can work well for most patients.

A few limitations regarding the experimental design are worth mentioning. First of all, we visualized a 2D plane of a 3D object, which was sufficient for our purpose because the macula is a small spot located near the center of the back of the retina. The visualized 2D plane went directly through this corresponding location on the eye model. To analyze drug trajectories in the entire vitreous chamber, a 3D PIV visualization might be useful.

Secondly, coefficients of thermal conductivity of glass (0.80) and air (0.26) are different from that of ocular tissues (cornea and sclera: 0.58). The well-known Penne's bioheat transfer equation is the standard for calculating temperature distribution in living tissues. It has been widely used to numerically analyze heat effects in the human eye. The equation is written as $$\nabla \cdot k \nabla T + q_p + q_m - W c_b (T - T_a) = \rho c_p \frac{\partial T}{\partial t},$$

where k is the tissue thermal conductivity, T is the local tissue temperature, qp is the external power deposition rate, $q_m$ is metabolism, $T_a$ is the arterial temperature, W is the local tissue-blood perfusion rate, $c_b$ is the blood specific heat, $c_p$ is the tissue specific heat, and ρ is the tissue density.

The model does not describe any convective heat transfer mechanism, but it can offer a basic understanding of what could happen when a heat source is applied to the eye. When the sclera is heated, blood circulation acts as an energy sink (T>$T_a$) and carries away the energy. In our study, the overall temperature increase in the eye model was around 2° C., which is conductive enough for our purpose. However, since air is still less thermally conductive and may not remove energy as efficiently from the system, it could have allowed the mixture in the eye model to heat up more easily. This indicates that for real eye applications, a higher temperature difference is likely to be preferred. A study on the heat tolerance of the sclera by Dewhirst et al. concluded that the threshold temperature for thermal damage is in the range of 59-61° C. when the sclera sample is heated for 10 min.3 A temperature difference of 10° C. as recommended in our study is well below this limit, which offers more flexibility for applications on real eyes.

Additionally, the refractive index is 1.36 for the working fluid (20.2 wt % glycerol) and 1.46 for quartz glass in this study. Immersing the glass globe in a viewing box that is filled with the working fluid can fix the refractive index issue. However, this is difficult to achieve because it is challenging to ensure the controlled local heating when a glass globe is immersed in the fluid. To understand the potential influence, we repeated the experiment with the face-up heating position with and without a fluid-filled viewing box. We learned that the percentage difference is in the range of 12-20% and the general vorticity increasing trend is consistent. This experimental result confirms that the potential error caused by unmatched refractive index will not change our conclusion.

Looking forward, variations on some important parameters remain to be explored. Interesting parameters relevant to both heating techniques (such as temperature difference, heating position, and heating contact area) and the morphology of the human eye (such as vitreous humor properties, which change the Prandtl number, and different geometries of the eye) can be investigated. This would allow us to develop more personalized treatments.

The disclosed thermally induced heating technique and pads can serve as a non-invasive add-on step at the end of the intravitreal injection procedure. Applying a medical-grade heating pad/probe to the desired location of the eye for a short period of time can promote treatment efficacy in a safe way.

To facilitate a better understanding of the impact of varying temperature gradient and heating position on the trajectory of individual particles, data obtained from PIV analysis were analyzed using PIV software. Variables including u, v, x, y, and t were coordinated to track individual particle behavior. Here, three scenarios were compared: ΔT=5° C. center heating, ΔT=10° C. center heating, and ΔT=10° C. lower heating.

Figure 38A:
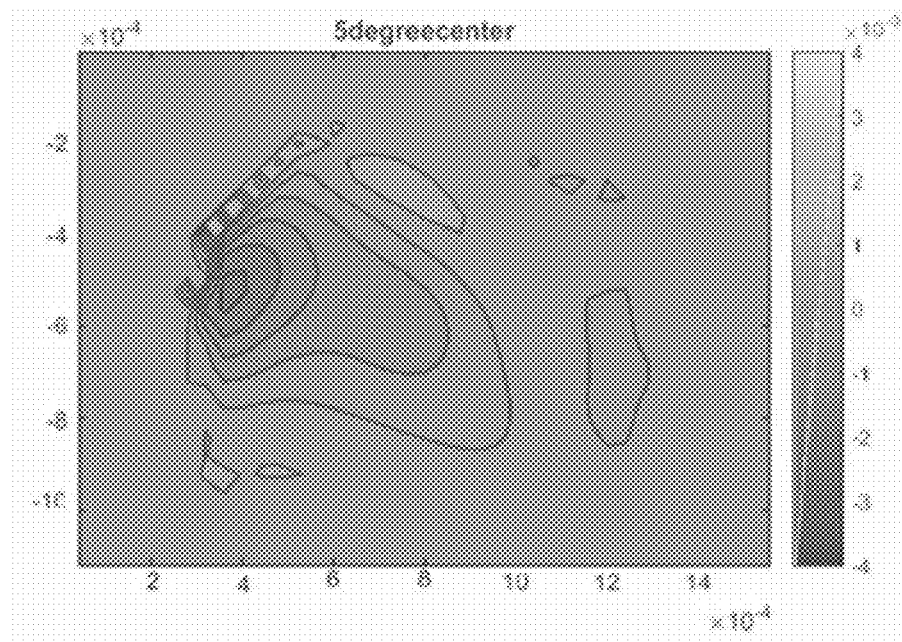
FIG. 38A illustrates an average vorticity plot of a process that uses a 5-Celsius temperature difference and center heating in accordance with some embodiments of the presentation disclosure.
Figure 38B:
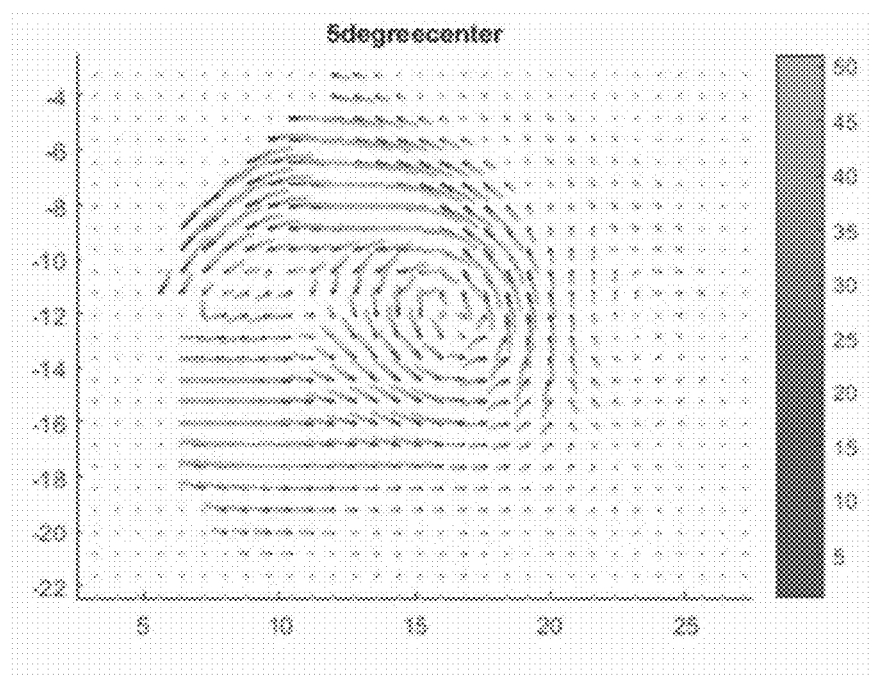
FIG. 38B illustrate a pathline visualization of a process that uses a 5-Celsius temperature difference and center heating in accordance with some embodiments of the presentation disclosure.
Figure 39A:
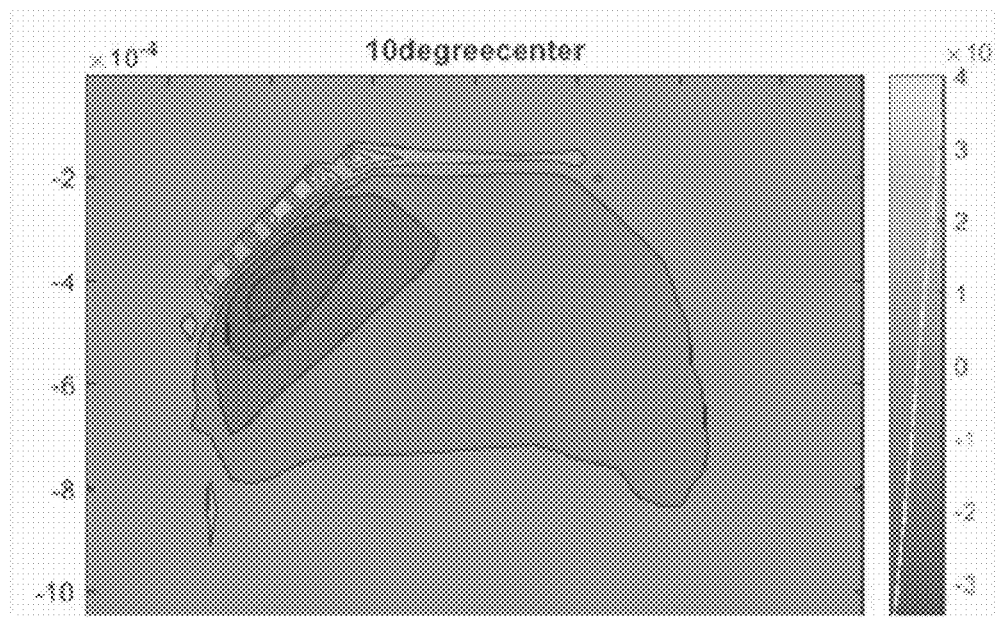
FIG. 39A illustrates an average vorticity plot of a process that uses a 10-Celsius temperature difference and center heating in accordance with some embodiments of the presentation disclosure.
Figure 39B:
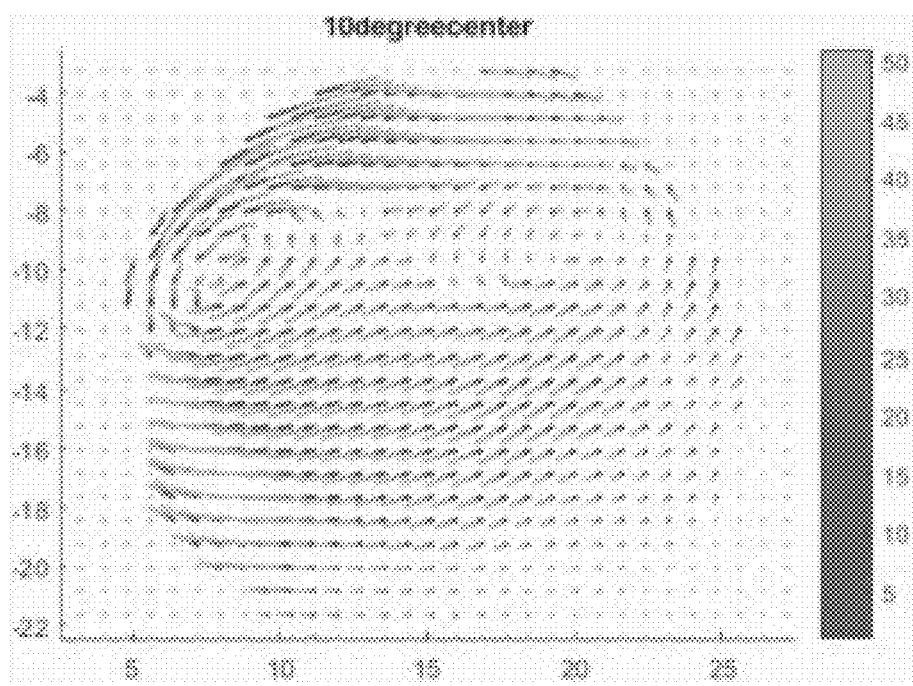
FIG. 39B illustrate a pathline visualization of a process that uses a 10-Celsius temperature difference and center heating in accordance with some embodiments of the presentation disclosure.

FIG. 38A illustrates the resulting vorticity plot of a vitreous humor model with heater 2700 at the center being activated (see FIG. 26) and ΔT=5° C. FIG. 38B illustrates the corresponding pathline visualization of FIG. 38A. FIG. 39A illustrates the resulting vorticity plot of the vitreous humor model with heater 2700 (being activated) at the center and ΔT at 10° C. FIG. 39B illustrates the corresponding pathline visualization of FIG. 39A.

Figure 40A:
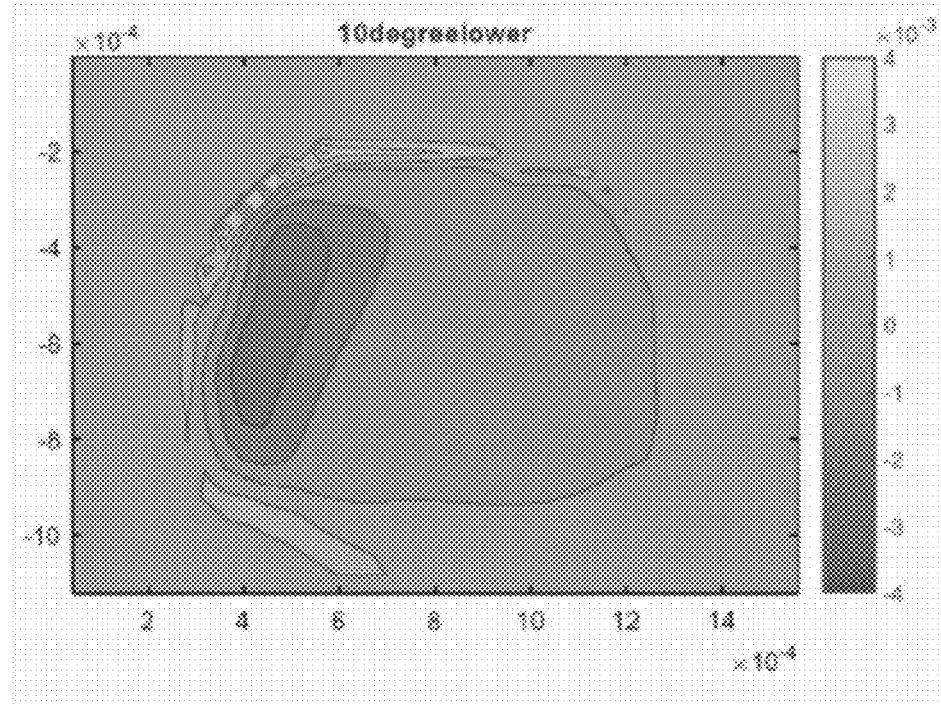
FIG. 40A illustrates an average vorticity plot of a process that uses a 10-Celsius temperature difference and lower heating in accordance with some embodiments of the presentation disclosure.
Figure 40B:
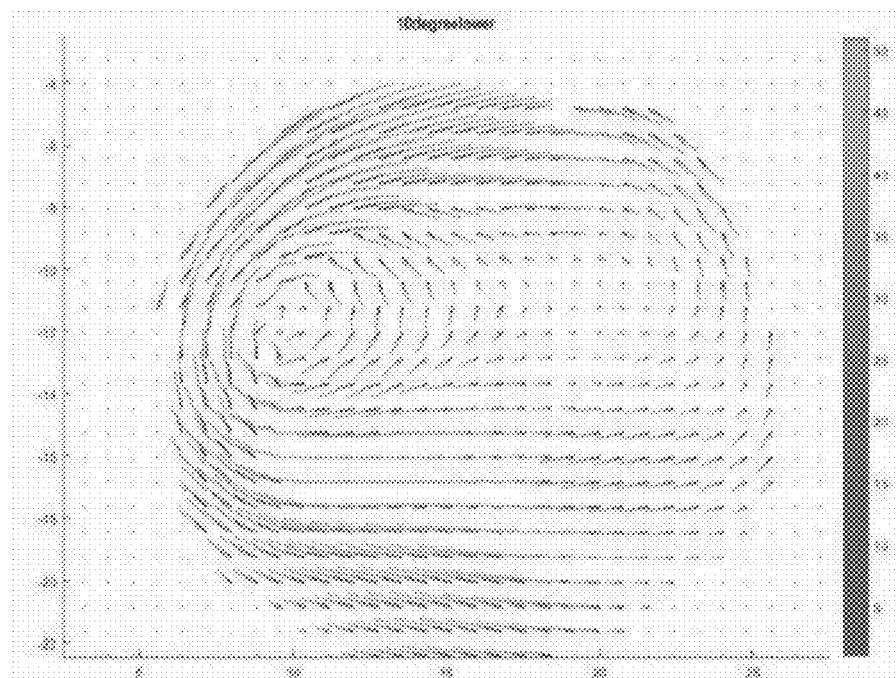
FIG. 40B illustrate a pathline visualization of a process that uses a 10-Celsius temperature difference and lower heating in accordance with some embodiments of the presentation disclosure.
Figure 41A:
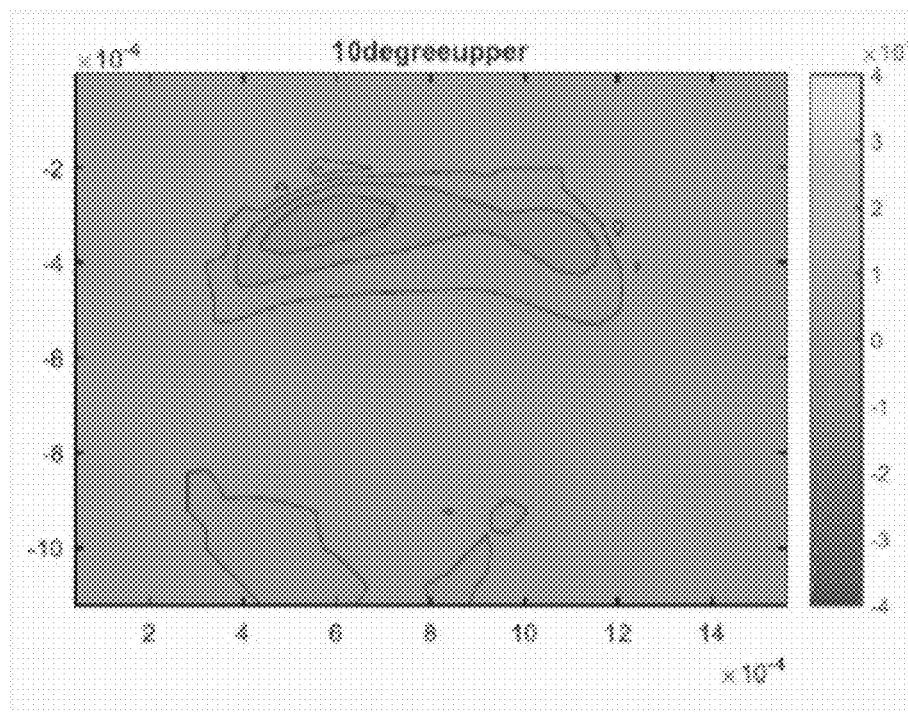
FIG. 41A illustrates an average vorticity plot of a process that uses a 10-Celsius temperature difference and upper heating in accordance with some embodiments of the presentation disclosure.
Figure 41B:
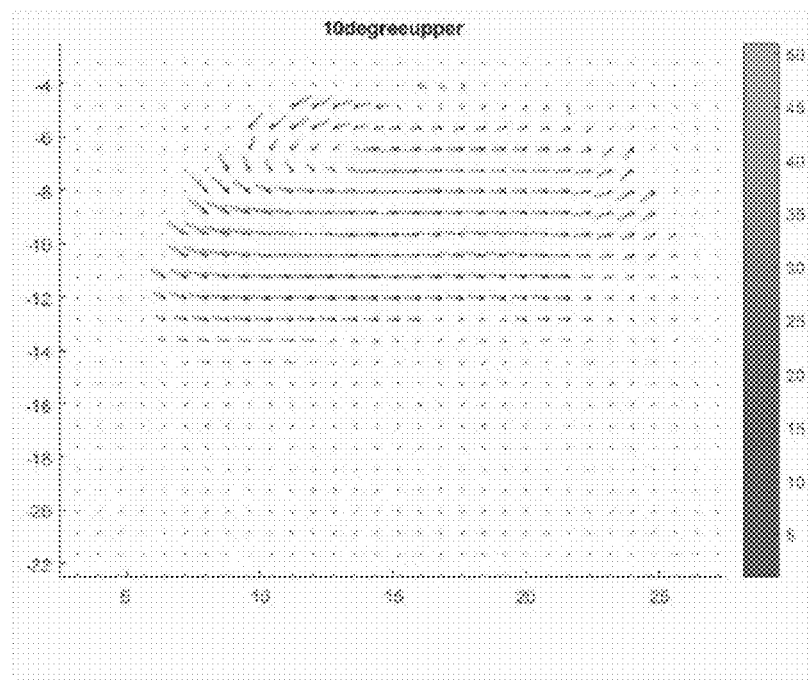
FIG. 41B illustrate a pathline visualization of a process that uses a 10-Celsius temperature difference and upper heating in accordance with some embodiments of the presentation disclosure.

FIG. 40A illustrates the resulting vorticity plot of the simulated vitreous humor with heater 2700 at the lower position and ΔT at 10° C. FIG. 40B illustrates the corresponding pathline visualization of FIG. 40A. Finally, FIG. 41A illustrates the resulting vorticity plot of the simulated vitreous humor with heater 2700 at the upper position and ΔT at 10° C. FIG. 41B illustrates the corresponding pathline visualization of FIG. 41A.

Figure 42A:
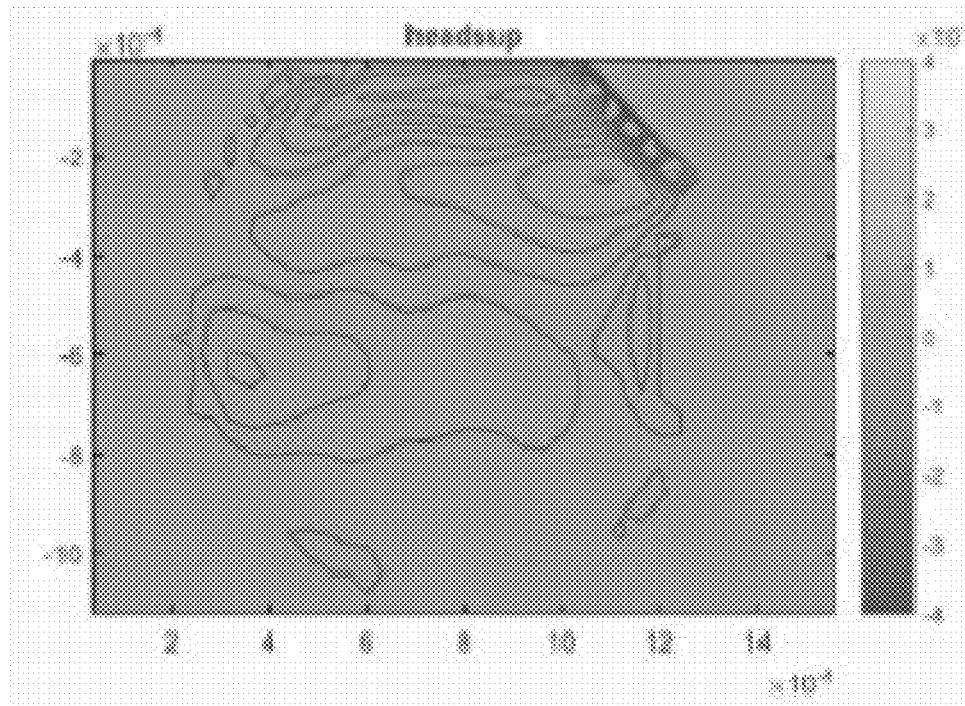
FIG. 42A illustrates an average vorticity plot of a process that uses a 10-Celsius temperature difference and heads-up heating in accordance with some embodiments of the presentation disclosure.
Figure 42B:
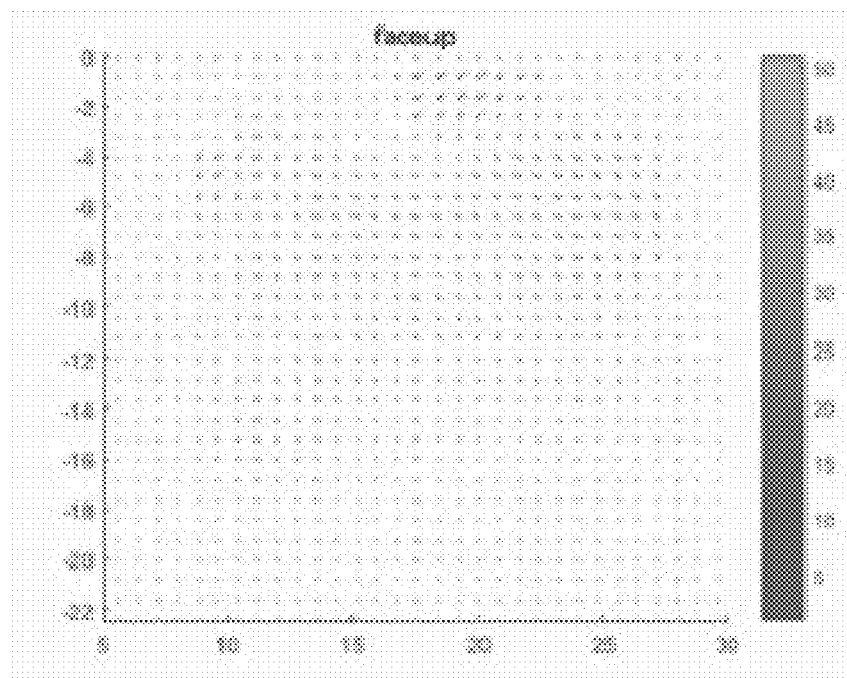
FIG. 42B illustrate a pathline visualization of a process that uses a 10-Celsius temperature difference and heads-up heating in accordance with some embodiments of the presentation disclosure.

FIG. 42A illustrates an average vorticity plot of a vitreous humor model with heater 2700 at the heads-up position and ΔT at 10° C. FIG. 42B illustrates the corresponding pathline visualization of FIG. 42A.

Figure 43A:
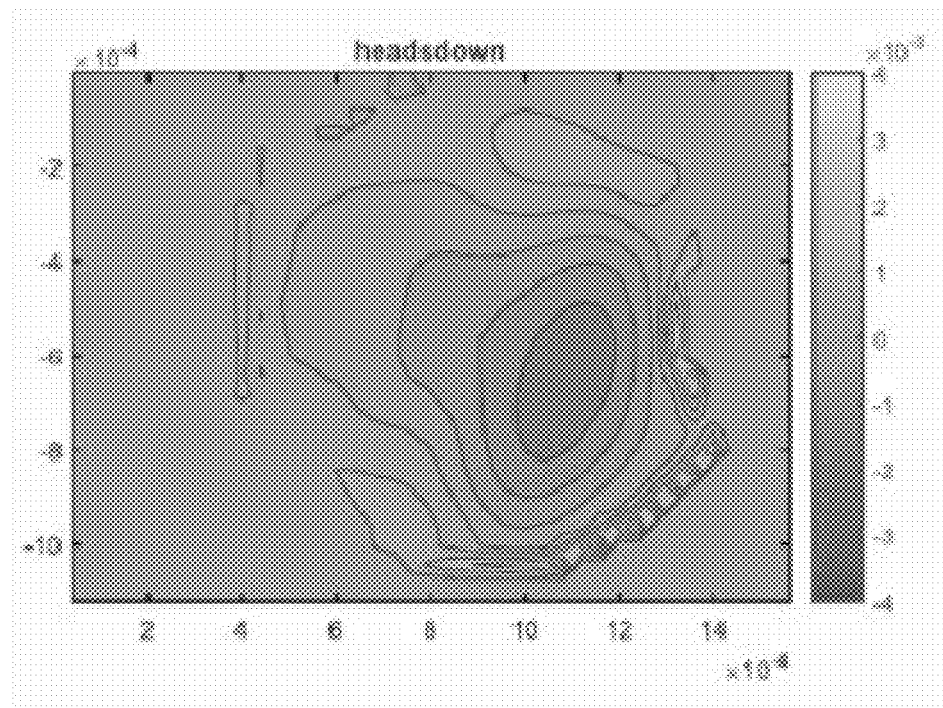
FIG. 43A illustrates an average vorticity plot of a process that uses a 10-Celsius temperature difference and heads-down heating in accordance with some embodiments of the presentation disclosure.
Figure 43B:
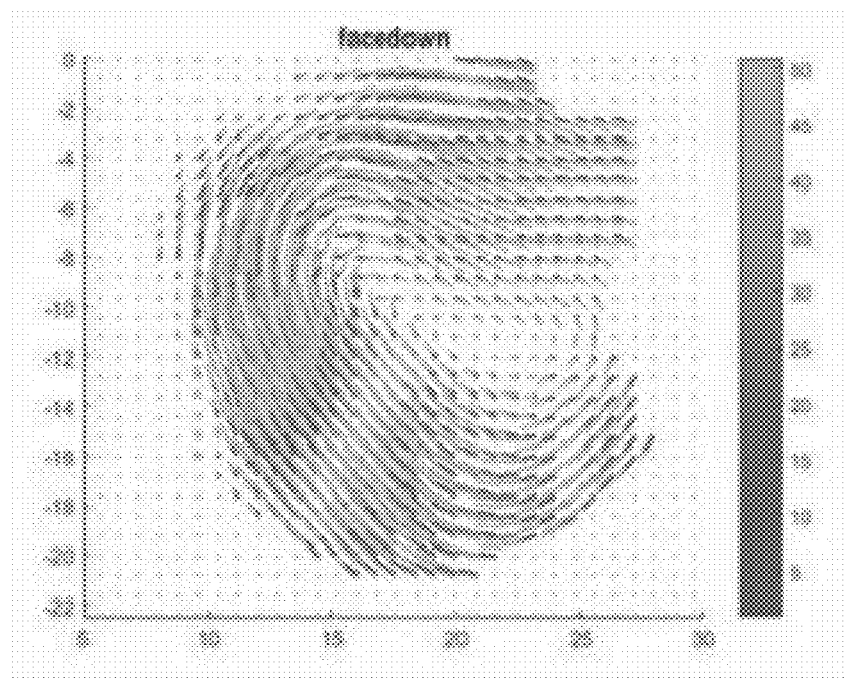
FIG. 43B illustrate a pathline visualization of a process that uses a 10-Celsius temperature difference and heads-down heating in accordance with some embodiments of the presentation disclosure.

FIG. 43A illustrates an average vorticity plot of a vitreous humor model with heater 2700 at the heads-down position and ΔT at 10° C. FIG. 43B illustrates the corresponding pathline visualization of FIG. 43A.

Figure 44:
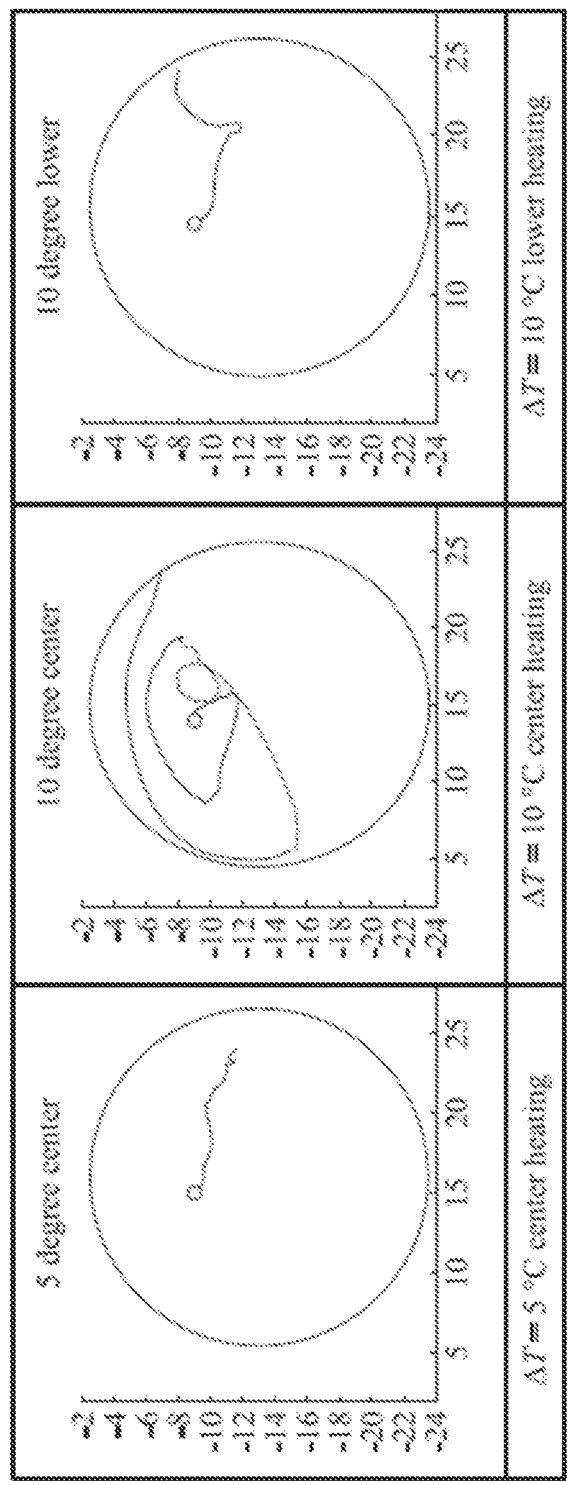
FIG. 44 illustrates graphs showing individual particle tracking for three different scenarios in accordance with some embodiments of the presentation disclosure.

FIG. 44 illustrates the tracking of an individual particle for the three different scenarios above. For a 2D analysis, it was assumed that a disk-shaped drug (radius=0.4 cm) was injected into the center plane of the vitreous chamber (radius=11 cm). The initial position of the drug in all three scenarios were kept the same and the goal was to observe the time duration it took for the particle to reach the back of the eye during the 10 mins heating process. The position of macula is in the back of the eye, which corresponds to the middle section of the right-side boundary of the circular domain. Since particles tend to move along the curvature once they are near the boundary, we claim that the particle delivery is successful as soon as it reaches the boundary on the right.

As it is demonstrated in FIG. 44, heating from a lower position at ΔT=10° C. helped the particle to deliver within the shortest time (less than 200 seconds); heating from the center position (media) at ΔT=10° C. trapped the particle in a flow circulation during the first 400 seconds but the particle could delivery successfully by the end of 600 seconds (10 mins); heating from the center position at ΔT=5° C. was not helpful. The results are consistent with observations from the previous pathline visualizations.

Quantification Results from LIF Visualization

Figure 45A:
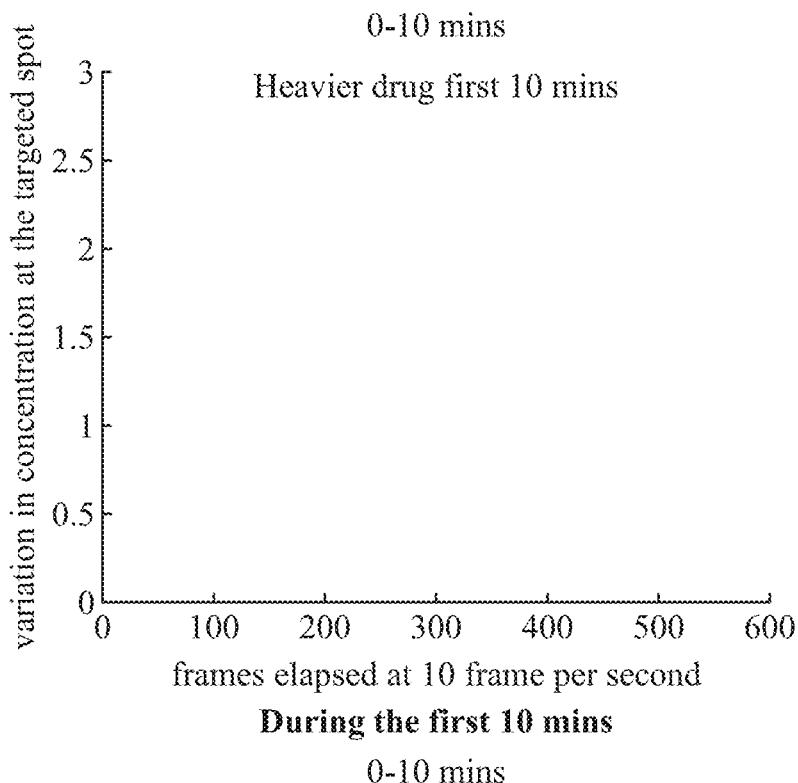
FIGS. 45A-45D illustrate pixel intensity results for various time and drugs in accordance with some embodiments of the presentation disclosure.
Figure 45B:
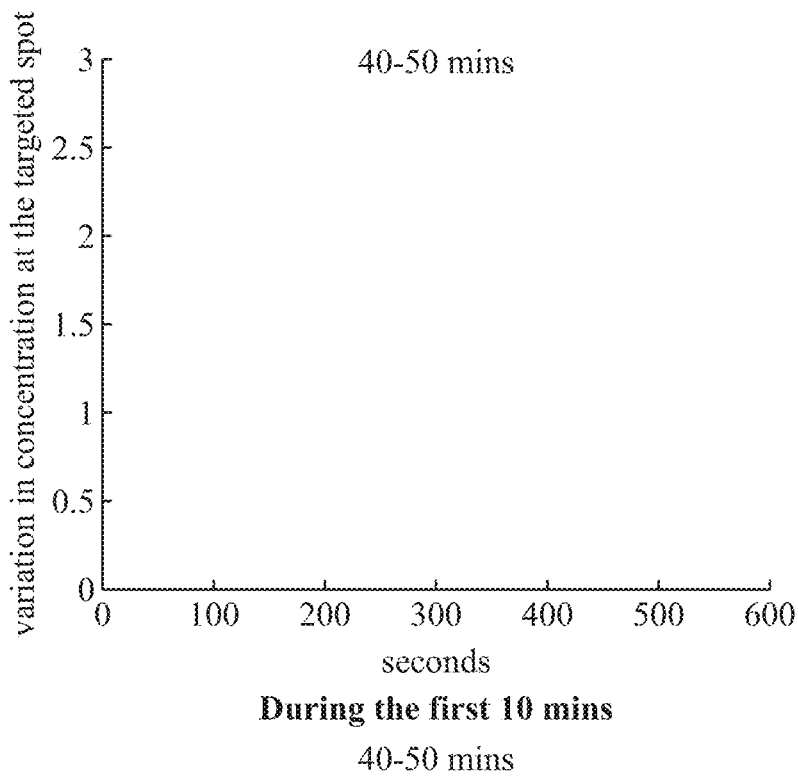
Figure 45C:
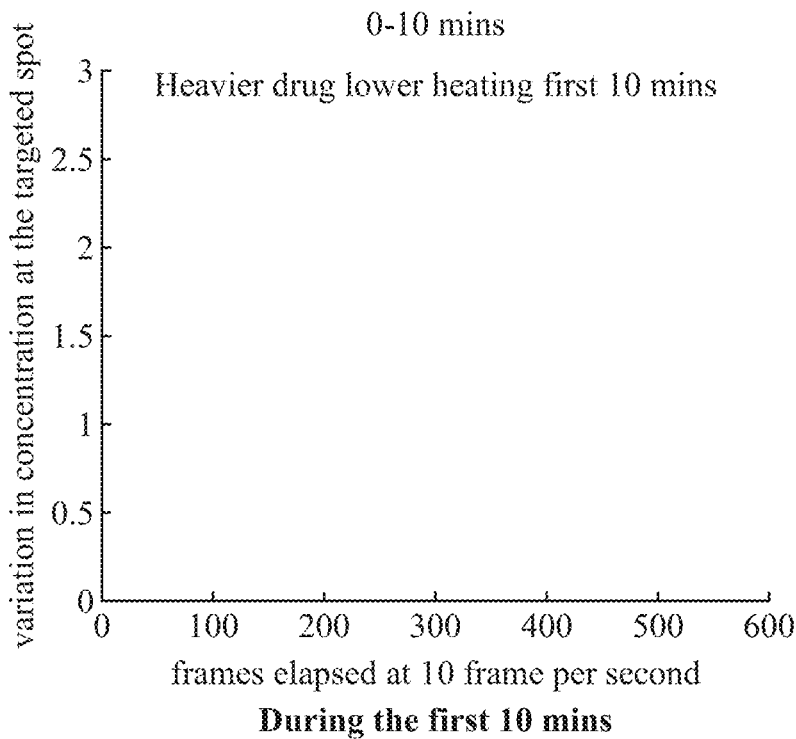
Figure 45D:
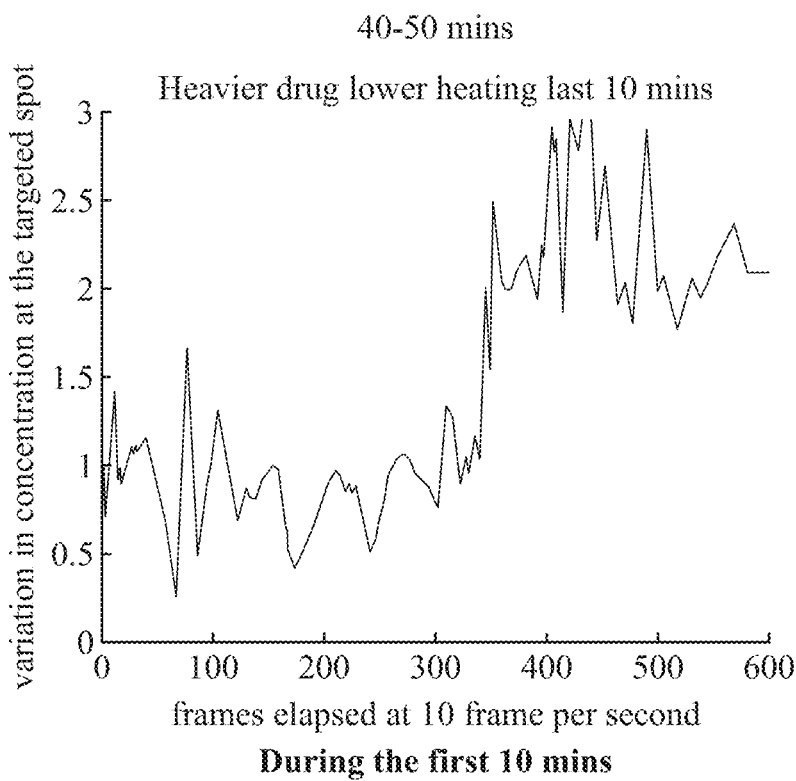
Figure 46A:
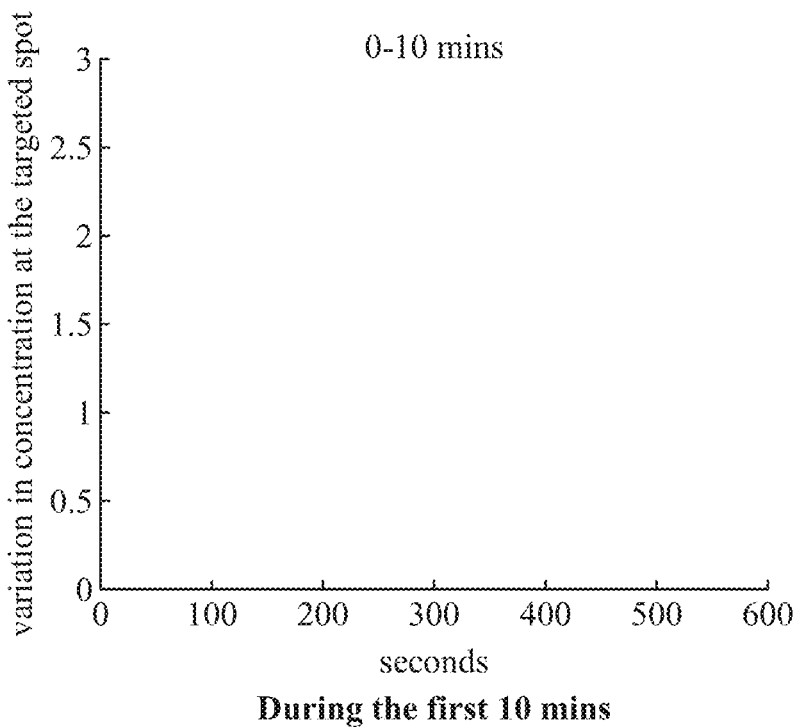
FIGS. 46A-46D illustrate pixel intensity results for various times and drugs in accordance with some embodiments of the presentation disclosure.
Figure 46B:
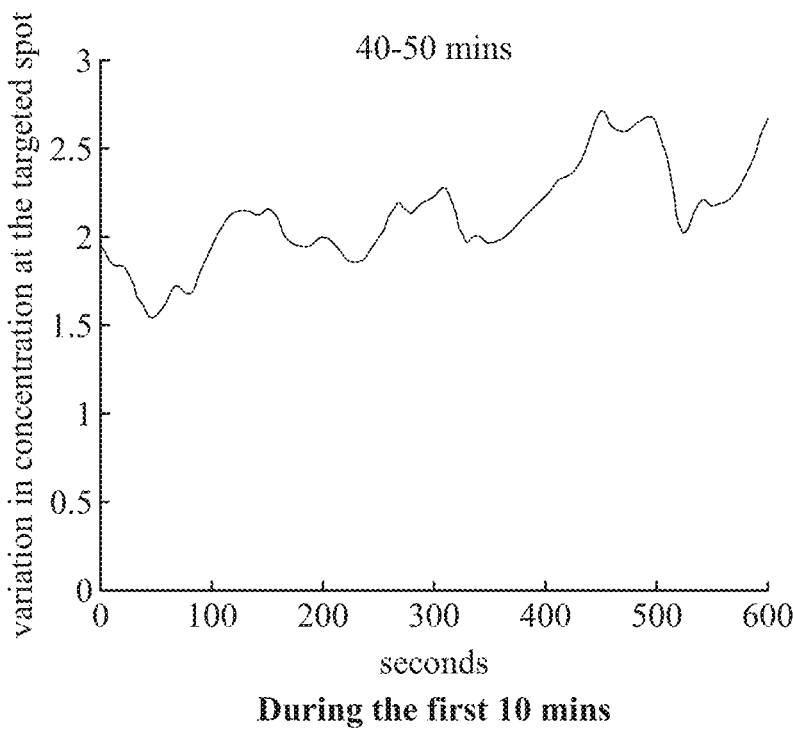
Figure 46C:
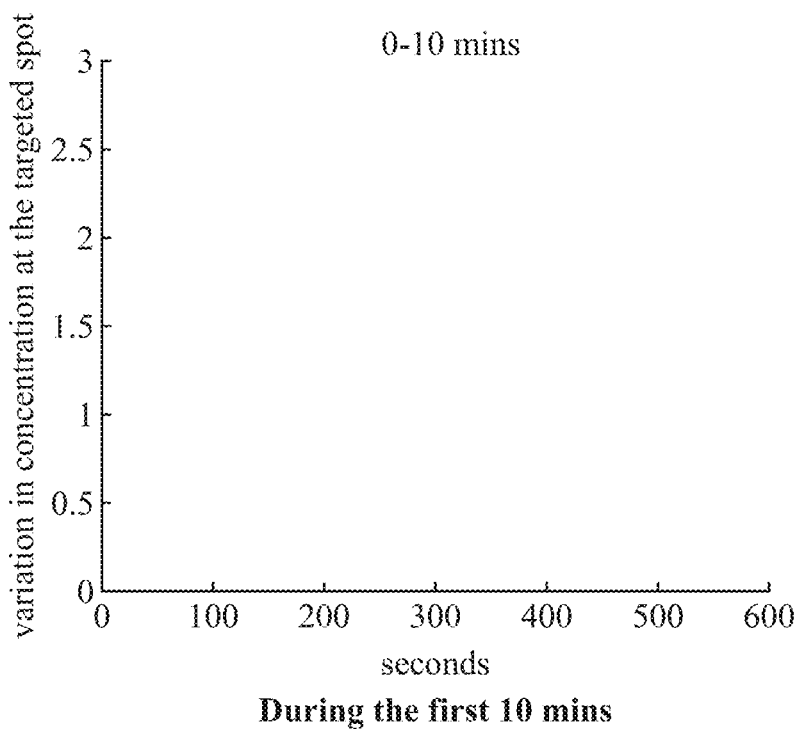
Figure 46D:
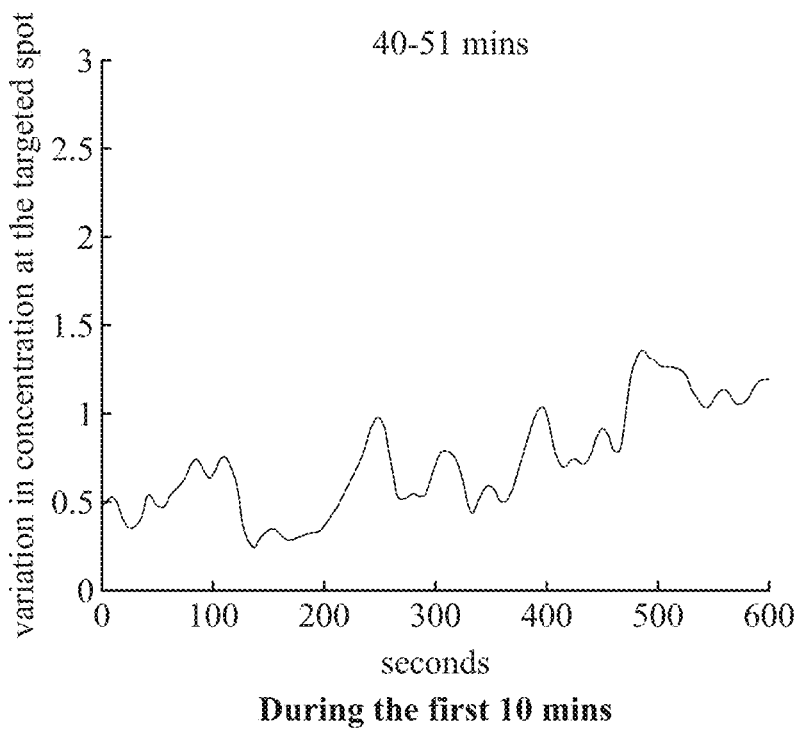

To simulate the actual drug delivery process, LIF visualization was performed on the following four cases:
1) Adding glycerol 33.6 wt % drug mixture into glycerol 20.2 wt % vitreous mixture with center heating (see FIGS. 45A-45B);
2) Adding glycerol 33.6 wt % drug mixture into glycerol 20.2 wt % vitreous mixture with lower heating (see FIGS. 45C-45D);
3) Adding glycerol 11.2 wt % drug mixture into glycerol 20.2 wt % vitreous mixture with center heating (see FIGS. 46A-46B); and
4) adding glycerol 11.2 wt % drug mixture into glycerol 20.2 wt % vitreous mixture with lower heating (see FIGS. 46C-46D).

The maximum pixel intensity reading from each heating method is summarized in Table 9. In summary, when drugs are heavier than the vitreous humor, heating from the center is not so helpful for facilitating drug mixing in the eye. When drugs are lighter than the vitreous humor, both center heating and lower heating are useful and can induce strong drug mixing profiles within an hour. Lower heating can activate strong drug mixing regardless of the density of the drug.

TABLE 9

| Computational Analysis (MATLAB/FEATool Multiphysics) | | |
|---|---|---|
| | Time Interval | |
| Heating Method | 0-10 mins | 40-50 mins |
| Lighter drug, center heating | 0 | In the range of 1.4-2.6 |
| Lighter drug, lower heating | 0 | In the range of 0.4-2.4 |
| Heavier drug, center heating | 0 | 0 |
| Heavier drug, lower heating | 0 | In the range of 0.5-3 |

Figure 47A:
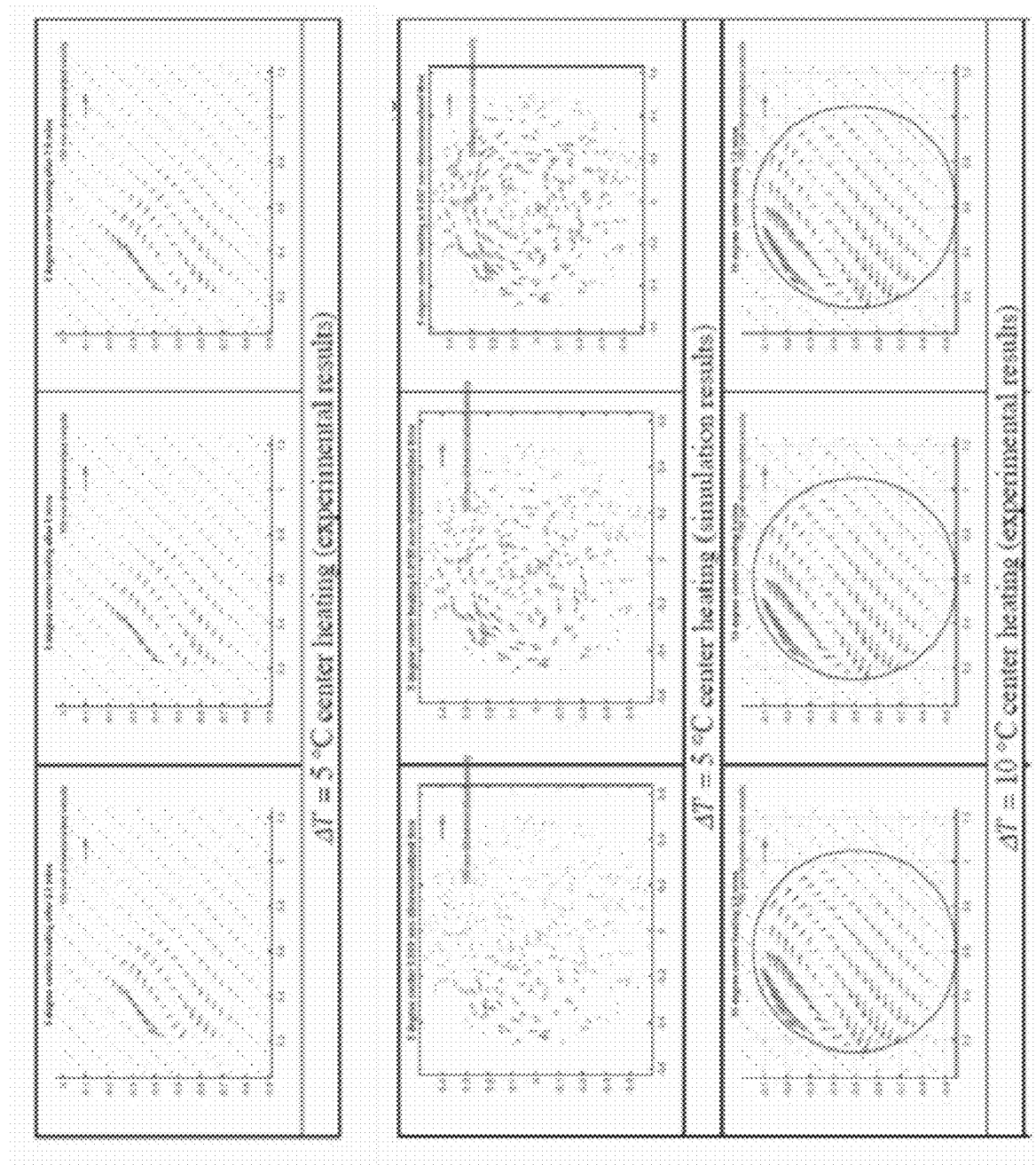
FIGS. 47A-47D illustrate experimental vs simulation velocity profiles for various times and drugs in accordance with some embodiments of the presentation disclosure.
Figure 47B:
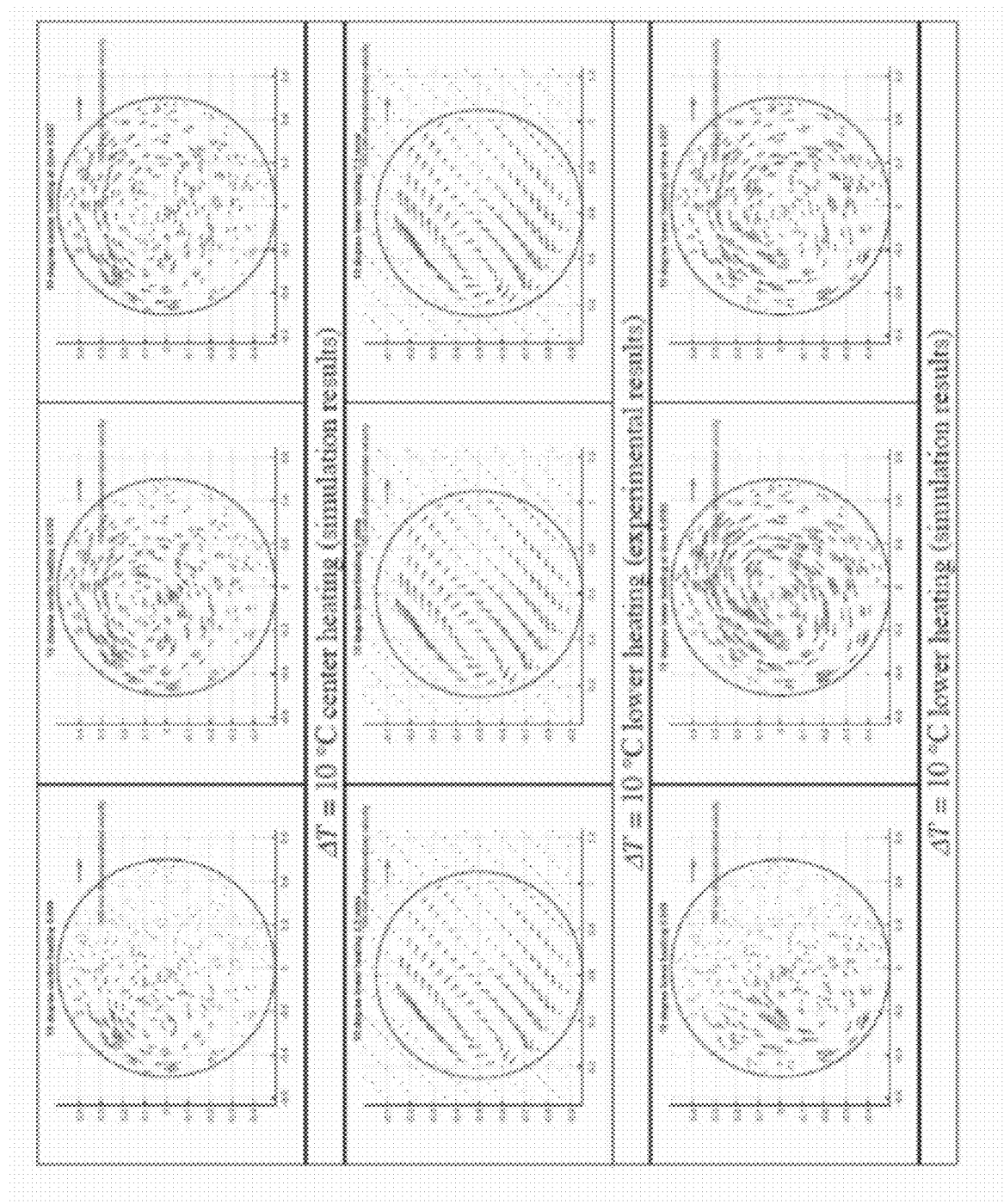
Figure 47C:
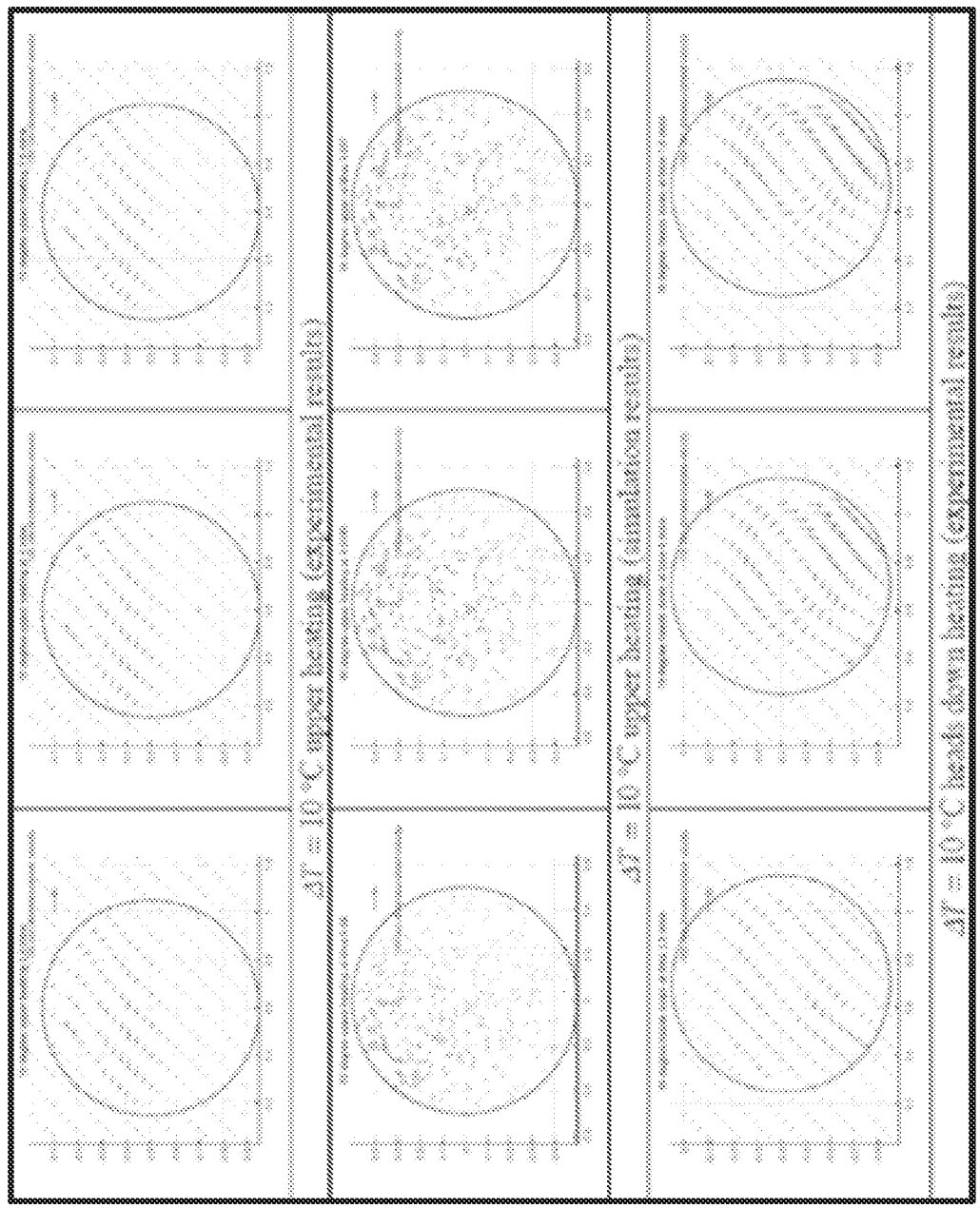
Figure 47D:
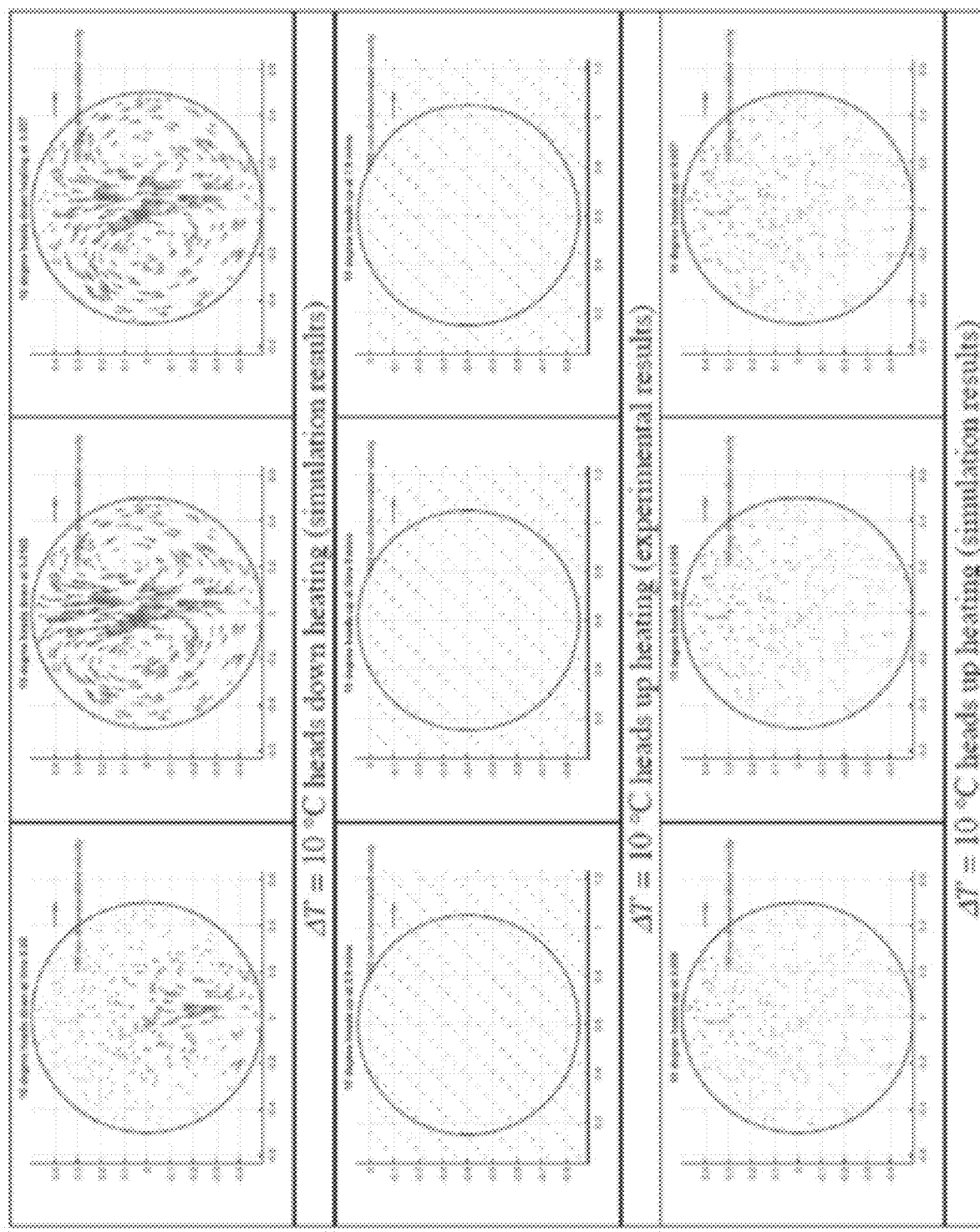
Figure 48:
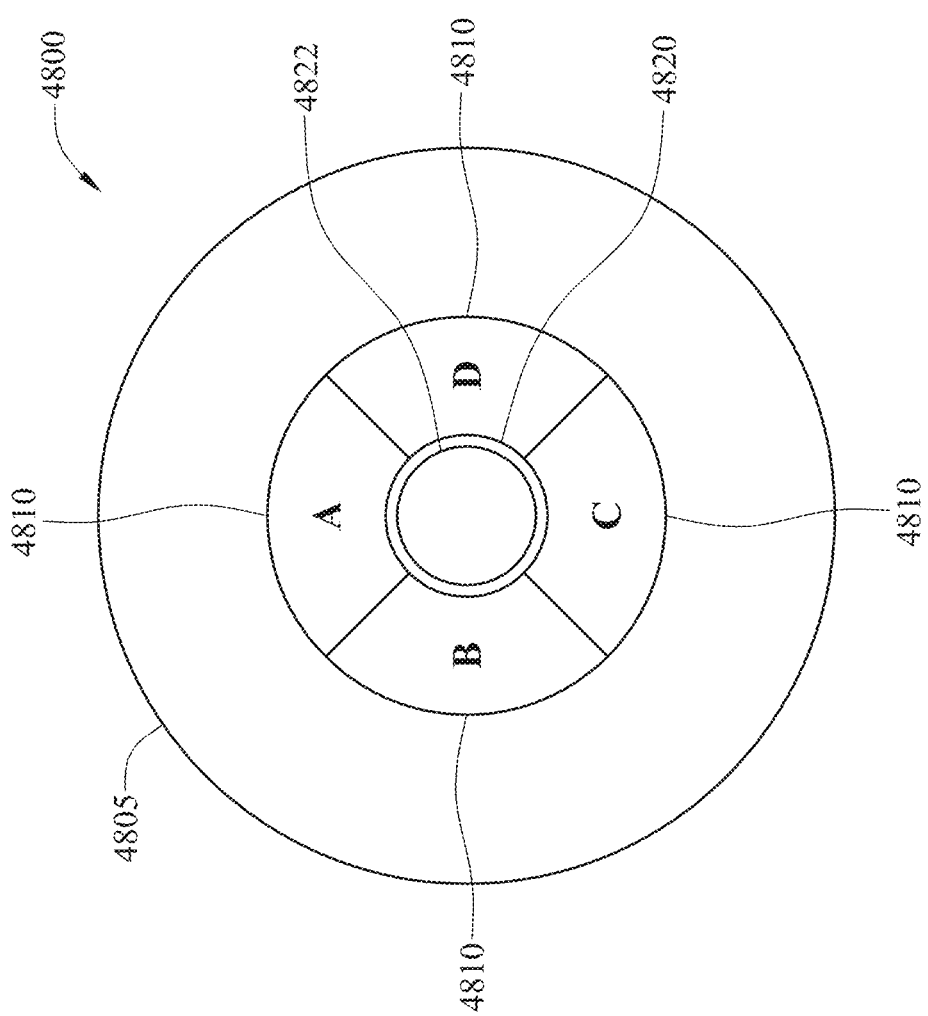
FIGS. 48 and 49 illustrate exemplary heat transfer pads in accordance with some embodiments of the presentation disclosure.
Figure 49:
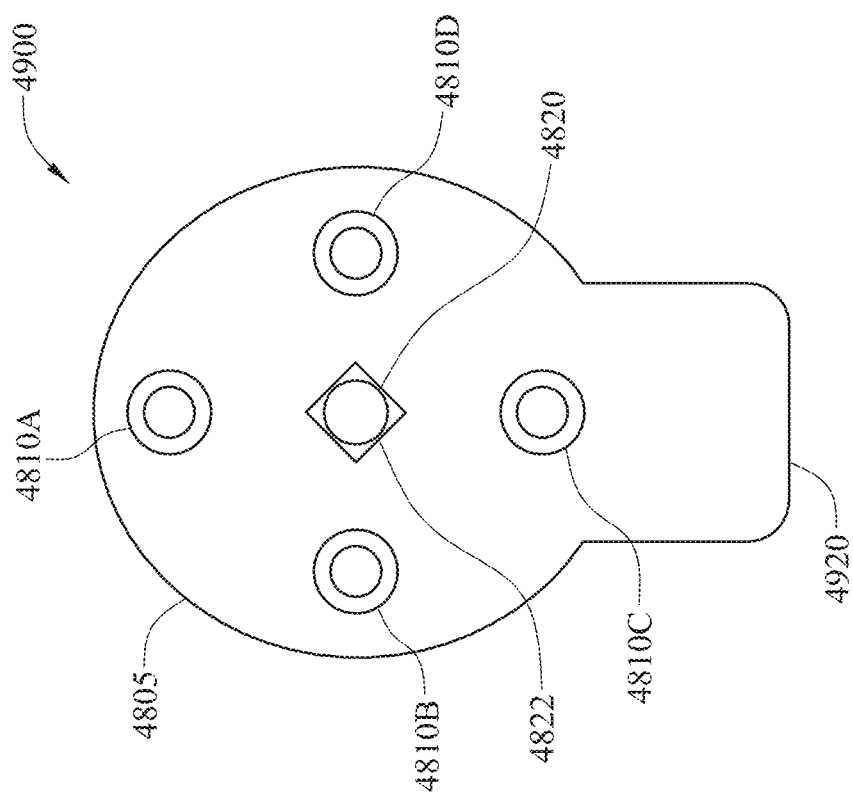

Both velocity profiles from experimental measurements and simulations are summarized in FIGS. 47A, B, C, and D below. Velocity profiles at t=2.5 min, 5 min, and 7.5 min from experimental measurements as well as T=0.009, 0.0185, and 0.037 (equivalent as t=45 s, 1.5 min, and 3 min) from numerical simulations are displayed. All the variables were non-dimensionalized with respect to the parameters described in the material and method section. Clearly, flow profile developed and became stabilized much faster in numerical simulations compared with experiments. This was because the experiments were conducted in 3D and numerical simulations were performed in 2D. However, the results are consistent in either method in terms of the velocity magnitude, flow direction, and movements of the center of the circulation. Therefore, numerical simulation method that was developed in this study could potentially be used in place of experiments for any future studies.

Dimensional Analysis

To understand the physical properties that are relevant, a dimensional analysis was performed. The following parameters are important in describing the physical properties in this experiment and their physical meanings are summarized in Table 10.

$$f(L, g, \beta, \Delta T, \rho, \mu, C_p, U, k) = 0 \tag{9}$$

TABLE 10

| L: characteristic length (diameter of the eyeball, length of heat source, etc) = [L] | g: gravitational acceleration = $[L][T]^{-2}$ |
|---|---|
| β: volumetric thermal expansion coefficient = $[\Theta]^{-1}$ | ΔT: temperature difference = $[\Theta]$ |
| ρ: density = $[M][L]^{-3}$ | μ: viscosity = $[M][L]^{-1}[T]^{-1}$ |
| $C_p$: specific heat = $[L]^2[T]^{-2}[\Theta]^{-1}$ | U: velocity = $[L][T]^{-1}$ |
| k: thermal conductivity = $[M][L][T]^{-3}[\Theta]^{-1}$ | |

{MLTΘ}: fundamental dimensions, [M] for mass, [L] for length, [T] for time. [Θ] for temperature There are nine variables and four fundamental dimensions. According to the Buckingham's Pi Theorem, five dimensionless groups are expected, they are:

Π1, Peclet number, which is a measure of the relative importance of convection versus diffusion:

$$\Pi 1 = \frac{L \rho C_p U}{k} = Pe \tag{10}$$

Π2, thermal expansion with respect to temperature change:

$$\Pi 2 = \Delta T \beta \tag{11}$$

Π3, Rayleigh number, associated with buoyancy-driven flow and can be regarded as a measure of the driving forces of natural convection. The magnitude of Rayleigh number is a good indication as to whether the natural convection boundary layer is laminar or turbulent:

$$\Pi 3 = \frac{C_p \rho^2 g \beta \Delta T L^3}{k \mu} = Ra \tag{12}$$

Π4, Prandtl number, which is a dimensionless quantity that puts the viscosity of a fluid in correlation with the thermal conductivity. It therefore assesses the relation between momentum transport and thermal transport capacity of a fluid (Physical Relationships Between Nanoparticle and Nanofluid Flow, 2015):

$$\Pi 4 = \frac{C_p \mu}{k} = Pr \tag{13}$$

Π5, The Reynolds number is the ratio of inertial forces to viscous forces, it is usually used to determine whether a fluid is in laminar or turbulent flow:

$$\Pi 5 = \frac{\rho U L}{\mu} = Re \tag{14}$$

Since Peclet number, Rayleigh number, and Prandtl number are most relevant to a natural convection problem, the actual values of these number for each of the three types of liquid at 21 Celsius were calculated and summarized in Table 11 below.

TABLE 11

| Solution | Pe | Pr | Ra |
|---|---|---|---|
| Water | 168 | 7.74 | 6,344 |
| Glycerol/Water Mixture (1:5) | 181 | 13.48 | 4,316 |
| Glycerol/Water Mixture (2:5) | 187 | 21.68 | 5,616 |

(Note: L = 5 mm and delta T = 5 for the characteristic length and temperature difference in Rayleigh number calculation)

The Peclet number serves as the Reynolds number counterpart for thermal energy transfer. It represents the ratio of the convection and diffusion fluxes in a flow. In our study, the Peclet number is on the scale of $10^2$, which indicates that convection plays a stronger role compared to diffusion in the heat/fluid transport phenomena. It is also worth noting that the Prandtl number that multiplies the Reynolds number is Peclet number.

The Prandtl number can be derived by introducing the concept of thermal diffusivity ($\alpha$), which describes the rate of temperature spread through a material. It measures the ability of a material to conduct thermal energy relative to its ability to store thermal energy. Thermal diffusivity is calculated from the thermal conductivity and the heat thermal capacity as given below:

$$\alpha = \frac{k}{\rho C_p}$$

where k is thermal conductivity, p is material density, and $C_p$ is specific heat capacity of materials. Therefore, using the idea of thermal diffusivity, the expression for Prandtl number is given below:

$$Pr = \frac{C_p \mu}{k} = v/\alpha$$

where v is kinematic viscosity, which is the ratio of dynamic viscosity to density.

Therefore, Prandtl number measures the significance of diffusion of momentum relative to that of heat transfer. The larger the Prandtl number, the thicker will be the momentum boundary layer compared to the thermal boundary layer. In this study, Prandtl number is in the range of 10-20, indicating the momentum transport plays a stronger role compared with heat transport.

The magnitude of Rayleigh number is a good indication as to whether the natural convection boundary layer is laminar or turbulent. For a Rayleigh number in the range of 103 to 104, the natural convection boundary layer is laminar. Based on the value of Peclet number and Prandtl number, it is possible to deduce that heat is primarily transported via flow convection: fluid that is heated up as the heat source carries heat and transports the heat with the flow. The flow circulation continuously brings colder solution to the heat source. Eventually, the entire solution inside the eye model is heated up, at which point circulation stops.

Baroclinic Torque and Flow Circulation

Flow circulation patterns were observed regardless of heating position or temperature difference. To understand the formation of the flow circulation, it is useful to refer to the concept of baroclinic torque. Baroclinic torque is the source of vorticity, which arises from unequal acceleration as a result of miss-aligned density gradient and pressure gradient, as shown in the equation for the transport of vorticity:

$$\frac{D\omega}{Dt} = -\omega(\nabla \cdot V) + \frac{\nabla \rho \times \nabla p}{\rho^2} + (\omega \cdot \nabla)V + \frac{1}{Re}(\nabla^2 \omega)$$

where term 1 on the right-hand side represents the effects of expansion on the vorticity field, term 2 is the baroclinic torque, term 3 describes vortex stretching, and term 4 describes the effects of viscous diffusion on vorticity distribution. For the flow fields in our study, term 2 is the only reason that vortices are formed. The baroclinic torque is the largest when the pressure gradient is perpendicular to the density gradient. The lighter fluid will be accelerated faster than the heavier fluid, resulting in a shear layer, and thus generating vorticity. In our case, this variation in fluid density is caused by thermal heating, and vorticity is generated as a result of density gradient that is unparalleled with pressure gradient.

Based on the above data observations and PIV observations, the thermal-driven method proved to be successful in distributing/mixing the drug in the vitreous humor. For example, for a person sitting in the upright position, applying a heat source (at least 5 Celsius greater than the eye temperature) to the lower position of his/her eye can active a strong fluid mixing in the entire vitreous chamber. Moreover, this method requires the minimal amount of efforts from patients.

Two methods for inducing drug mixing into the eye after an intravitreal injection were disclosed above. The first method is a motion-driven method, which is based on lateral movements to the eye. The second method is thermal-driven, which relies on the application of heat to the eye at various heating positions. It can be concluded that the thermal-driven method appears to be more effective in agitating fluid mixings in the eye. It is also more flexible in dealing with the density variance among different individuals as well as age groups. In addition, it also provides an alternative to having a cooling pad in place of a heat source. The idea is the same although direction of fluid circulation will be the opposite in the case of using a cooling pad.

Apart from intravitreal injections, the study outcome can also be useful for applications in other eye treatment methods, especially for drug-releasing ocular implants. Since the majority of these ocular implants are designed to provide a sustained release of medication for a long period which ranges from months to years, a well-established fluid mixing profile in the eye can certainly help in making sure that the small amounts of drugs being release can effectively reach the target issue and eventually achieve an optimal treatment efficacy.

Figure 51:
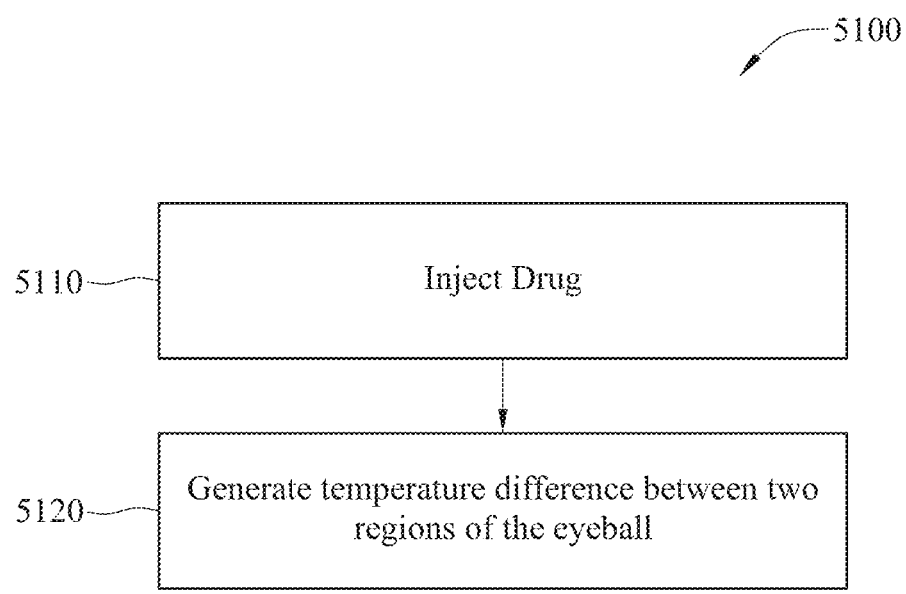
FIG. 51 illustrates a process flow chart for inducing drug mix in accordance with some embodiments of the presentation disclosure.

FIG. 51 illustrates a heat transfer eye patch 4800 for inducing circulation in the vitreous humor. Heat transfer eye patch 4800 can be a pad that introduces heating/cooling effects to increase natural convection within the vitreous humor. In this way, better mixings of drugs injected into the vitreous chamber can be achieved, which leads to improved drug delivery.

In some embodiments, heat transfer eye patch 4800 can include a contact pad 4805, heat transfer elements 4810, a power module 5115, and control circuit (not shown). Contact pad 4805 can be made of a soft material that can conduct heat. In some embodiments, contact pad 4805 can be a silicone based material with heat conducting property. Other flexible biocompatible materials with good contact properties with the eye and skin can also be used. Contact pad 4805 can have a coating of sticky material that helps hold contact pad 4805 to the eye and/or skin. The sticky material can be a biocompatible glue.

Heat transfer elements 4810 can be heating elements disposed at various location on contact pad 4805. In some embodiments, contact pad 4805 can have one or more heat transfer elements 4810. For example, contact pad 4805 can have two, three, four, or six heating elements 4810. In some embodiments, contact pad 4805 has four heating elements. The temperature of each element can be controlled independently using power module 5115 and/or the control circuit (not shown). It should be noted that power module 4820 and the control circuit can be an integrated part, which can be a control module (not shown) that functions both as a power delivery and control unit. Power module 4820 can be coupled to each heat transfer element 4810 such that the temperature of each heat transfer element 4810 can be independently controlled. Heat transfer elements 4810 can be spaced apart or they can be placed adjacent to each other. Heat transfer element 4810 A can be disposed above heat transfer element 4810C. Heat transfer element 4810 B can be disposed on the left of heat transfer element 5510D.

In some embodiments, heat transfer elements 4810B and/or 4810D can be activated for center (medial) heating. In other words, for center heating, only heat transfer element 4810B or 4810D is activated, or both can be activated.

Heat transfer elements 4810 can also be cooling elements that can extract heat away from the eye. In this embodiment, each element 4810 can be coupled to a conduit that delivers cooling fluid to element 4810. In some embodiments, each heat transfer element 4810 can have a combination of heating and cooling elements.

Heat transfer eye patch 4800 can also include an insulated region 4820 that protects the cornea. Insulated region 4820 can protect the cornea from heat transfer elements 4810 and prevents the lens from being over-heated or over-cooled. In some embodiments, power module 4822 can be disposed on region 4820.

Power module 4822 can activate one or more of the heat transfer elements 4810 to generate a temperature difference between a heat transfer element and the area of the eye adjacent to the heat transfer element. The adjacent area can be the area of the eye that is in contact or substantial contact with the heat transfer element. The adjacent area can have a thickness such that it extends into the vitreous humor. The temperature difference between the heat transfer pad and the adjacent area of the eye can also create a temperature difference between the adjacent area and another (e.g., non-adjacent) region of the eye. In this way, the vitreous humor of the eye can have regions of different temperature, which can lead to better internal flow and mixing of the drug. Power module 4820 can control the voltage or amperage delivered to each of the heat transfer elements 4810 in order to control the heating and/or cooling effects (heat transfer characteristic) of each element.

FIG. 52 illustrates a heat transfer eye patch 5200 for inducing circulation in the vitreous humor. Eye patch 5200 can include four heat transfer elements 4810 and a center region 4822, which can also contain power module 4820.

Similar to eye patch 4800, eye patch 5200 can have heat transfer element 4810A at the top of the eye, element 4810B at the far left of the eye, element 4810C at the bottom of the eye, and element 4810D at the far right of the eye. Pad 4805 can be circular and can have a flap 4920 in one of the quadrants, which can house power, cooling, and/or data cable. In some embodiments, power module 4820 can be disposed on flap 4920 instead of center region 4822. Flap 4920 can also have adhesive on the surface facing the patient's skin. In this way, flap 4920 can be adhesively secured to the patient's skin just under the eye. This provides support for eye patch 5200 while it is being attached to the patient's eye. In some embodiments, eye patch 5200 can include two flaps at opposite sides of eye patch 5200. In this way, a top flap (not shown) can be adhesively secured to the top of the eye near or over the eyebrow.

Figure 50B:
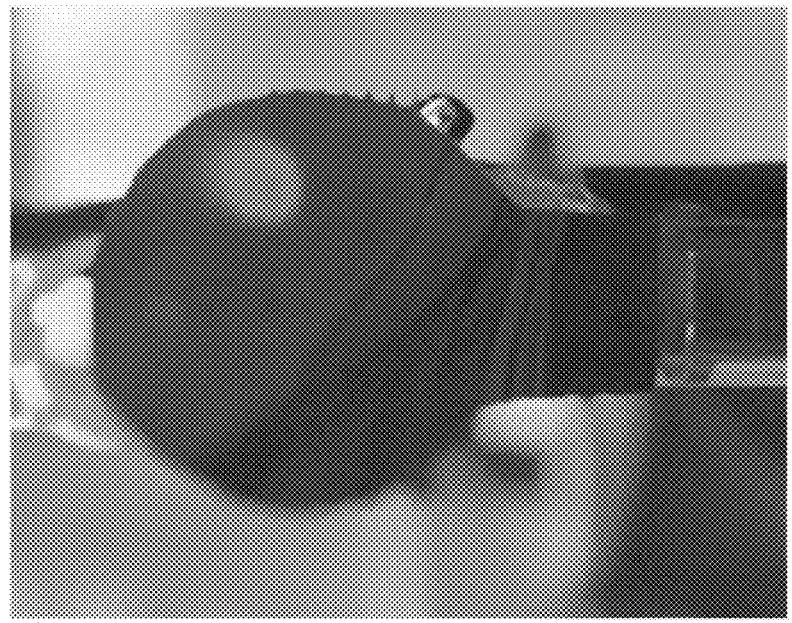
FIGS. 50A and 50B illustrates a heat transfer pad in accordance with some embodiments of the presentation disclosure.
Figure 50A:
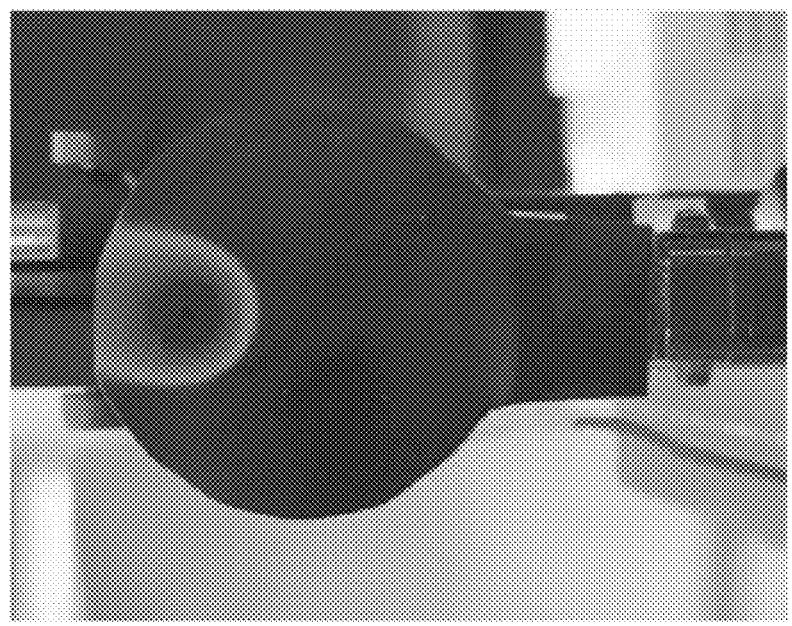

FIGS. 50A and 50B illustrate example heat signature of pads 5200 when one of the heat transfer elements 4810 is activated. In use, eye patch 4800 or 5200 can be placed on the patient's eyeball. In some embodiments, each of the heat transfer elements 4810 can include an integrate power control circuitry (not shown) that can be remotely controlled and/or programmed. In this embodiment, a separate power module is not necessary as each heat transfer element 4810 has its own control circuitry, which can be programmed using various wireless communication protocols such as Bluetooth and NFC (near-field communication).

FIG. 51 illustrates a process 5100 for inducing drug to mix in the vitreous humor of a human patient. Process 5100 starts at box 5110 when a drug is injected into the vitreous humor. At 5120, a temperature difference is generated between one or more heat transfer pads and the adjacent area of the eye at each heat transfer pad. The temperature difference can be generated by applying or removing heat from one or more regions of the eye where the one or more heat transfer pads are located. In some embodiments, the center (when facing down) portion (see FIG. 26) of the eyeball is heated or cooled using a heat transfer pad (e.g., heat transfer pad 4800). In this embodiment, the temperature difference between the one or more heat transfer pads (4810B and/or 4810D) at the center region of the eye and the respective adjacent area can be between 2.5 to 12.5 degrees Celsius.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the following detailed description are presented in terms of algorithms and symbolic representations of operations on data bits within a computer memory. These algorithmic descriptions and representations are the methods used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared or otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following disclosure, it is appreciated that throughout the disclosure terms such as "processing," "computing," "calculating," "determining," "displaying" or the like, refer to the action and processes of a computer system, or similar electronic computing device, that manipulates and transforms data represented as physical (electronic) quantities within the computer system's registers and memories into other data similarly represented as physical quantities within the computer system's memories or registers or other such information storage, transmission or display.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. It will be appreciated that a variety of programming languages may be used to implement the teachings of the invention as described herein.

The figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present invention be limited not by this detailed description, but rather by the claims of this application. As will be understood by those familiar with the art, the present invention may be embodied in other specific forms without departing from the spirit or essential characteristics thereof. Likewise, the particular naming and division of the modules, routines, features, attributes, methodologies and other aspects are not mandatory or significant, and the mechanisms that implement the present invention or its features may have different names, divisions and/or formats.

Furthermore, as will be apparent to one of ordinary skill in the relevant art, the modules, routines, features, attributes, methodologies and other aspects of the present invention can be implemented as software, hardware, firmware or any combination of the three. Also, wherever a component, an example of which is a module, of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming.

Additionally, the present invention is in no way limited to implementation in any specific programming language, or for any specific operating system or environment. Accordingly, the disclosure of the present invention is intended to be illustrative, but not limiting, of the scope of the present invention, which is set forth in the following claims.

The invention claimed is:

1. A medical apparatus to induce drug mixing comprising:
    a flexible contact pad configured to be placed over an eyeball of a patient;
    a plurality of heat transfer elements disposed on the flexible contact pad configured to transfer heat out of or into the flexible pad; and
    a control module electronically coupled to each of the plurality of the heat transfer elements for controlling the temperature of each heat transfer element,
    wherein the flexible contact pad is configured to be placed in direct contact with the eyeball of the patient.

2. The medical apparatus of claim 1, wherein the plurality of heat transfer elements comprises four heat transfer elements.

3. The medical apparatus of claim 2, wherein the four heat transfer elements are disposed at four quadrants of the flexible contact pad.

4. The medical apparatus of claim 1, wherein the flexible contact pad comprises a silicone pad with heat conducting property.

5. The medical apparatus of claim 1, wherein the flexible contact pad comprises one or more flaps extending outward.

6. The medical apparatus of claim 5, wherein the one or more flaps comprise at least a pair of flaps, wherein the pair of flaps are disposed on opposite sides of the flexible pad.

7. The medical apparatus of claim 6, wherein the one or more flaps comprises an adhesive layer on a surface opposite of the plurality of heat transfer elements.

8. The medical apparatus of claim 1, wherein the control module is configured to independently control a heat transfer characteristic of each heat transfer element.

9. The medical apparatus of claim 1, wherein the control module is configured to create a temperature difference between a heat transfer pad and an adjacent area of the eyeball.

10. The medical apparatus of claim 9, wherein the control module is configured to create a temperature difference of 2.5 to 12.5 degrees Celsius between the heat transfer pad and the adjacent area of the eyeball.

11. The medical apparatus of claim 1, wherein the control module is configured to activate only the heat transfer element at a lower quadrant of the flexible pad.

12. An eye patch for inducing drug to mix in a patient's vitreous humor, the eye patch comprising:
    a heat transfer pad configured to transfer heat to or from an eyeball, the heat transfer pad including:
        a flexible contact pad configured to be placed over the eyeball of the patient;
        a plurality of heat transfer elements disposed on the flexible contact pad configured to transfer heat out of or into the flexible pad; and
        a control module electronically coupled to the heat transfer pad for controlling one or more heat transfer elements disposed on the heat transfer pad,
    wherein the eye patch is configured to be placed in direct contact with the eyeball of the patient.

* * * * *